(12) United States Patent
Hoekman et al.

(10) Patent No.: US 11,690,819 B2
(45) Date of Patent: Jul. 4, 2023

(54) RESPIRATORY TRACT DELIVERY OF LEVODOPA AND DOPA DECARBOXYLASE INHIBITOR FOR TREATMENT OF PARKINSON'S DISEASE

(71) Applicant: Impel Pharmaceuticals Inc., Seattle, WA (US)

(72) Inventors: John D. Hoekman, Seattle, WA (US); Kelsey H. Satterly, Seattle, WA (US); Inna Dashevsky, Seattle, WA (US); Aditya R. Das, Foster City, CA (US); Stephen B. Shrewsbury, Fallbrook, CA (US); Gregory J. Davies, Issaquah, WA (US); Bhavin Y. Gajera, Bellevue, WA (US)

(73) Assignee: Impel Pharmaceuticals Inc., Seattle, WA (US)

( * ) Notice: Subject to any disclaimer, the term of this patent is extended or adjusted under 35 U.S.C. 154(b) by 0 days.

(21) Appl. No.: 17/682,033

(22) Filed: Feb. 28, 2022

(65) Prior Publication Data
US 2022/0233486 A1 Jul. 28, 2022

Related U.S. Application Data

(62) Division of application No. 16/517,423, filed on Jul. 19, 2019.

(60) Provisional application No. 62/700,584, filed on Jul. 19, 2018, provisional application No. 62/820,244, filed on Mar. 18, 2019.

(51) Int. Cl.
| | |
|---|---|
| *A61K 31/198* | (2006.01) |
| *A61K 9/00* | (2006.01) |
| *A61K 9/14* | (2006.01) |
| *A61K 9/16* | (2006.01) |
| *A61K 9/48* | (2006.01) |
| *A61K 31/165* | (2006.01) |
| *A61M 11/02* | (2006.01) |
| *A61M 15/00* | (2006.01) |
| *A61M 15/08* | (2006.01) |
| *A61P 25/16* | (2006.01) |

(52) U.S. Cl.
CPC .......... *A61K 31/198* (2013.01); *A61K 9/0043* (2013.01); *A61K 9/0053* (2013.01); *A61K 9/0075* (2013.01); *A61K 9/14* (2013.01); *A61K 9/1623* (2013.01); *A61K 9/1652* (2013.01); *A61K 9/48* (2013.01); *A61K 31/165* (2013.01); *A61M 11/02* (2013.01); *A61M 15/003* (2014.02); *A61M 15/0035* (2014.02); *A61M 15/0036* (2014.02); *A61M 15/08* (2013.01); *A61P 25/16* (2018.01); *A61M 15/009* (2013.01); *A61M 2202/04* (2013.01); *A61M 2202/064* (2013.01); *A61M 2205/8225* (2013.01); *A61M 2206/20* (2013.01)

(58) Field of Classification Search
None
See application file for complete search history.

(56) References Cited

U.S. PATENT DOCUMENTS

| | | |
|---|---|---|
| 2,933,259 A | 4/1960 | Raskin |
| 3,425,414 A | 2/1969 | La Roche |
| 3,888,253 A | 6/1975 | Watt et al. |
| 3,906,950 A | 9/1975 | Cocozza |
| 3,908,654 A | 9/1975 | Lhoest et al. |
| 3,971,377 A | 7/1976 | Damani |
| 4,095,596 A | 6/1978 | Grayson |
| 4,187,985 A | 2/1980 | Goth |
| 4,227,522 A | 10/1980 | Carris |
| 4,353,365 A | 10/1982 | Hallworth et al. |
| 4,412,573 A | 11/1983 | Zdeb |
| 4,620,670 A | 11/1986 | Hughes |
| 4,702,415 A | 10/1987 | Hughes |
| 4,896,832 A | 1/1990 | Howlett |
| 4,995,385 A | 2/1991 | Valentini et al. |
| 5,093,372 A | 3/1992 | Uedo et al. |
| 5,224,471 A | 7/1993 | Marelli et al. |
| 5,307,953 A | 5/1994 | Regan |
| 5,331,954 A | 7/1994 | Rex et al. |
| 5,349,947 A | 9/1994 | Newhouse et al. |
| 5,382,236 A | 1/1995 | Otto et al. |

(Continued)

FOREIGN PATENT DOCUMENTS

| | | |
|---|---|---|
| CN | 103917265 A | 7/2014 |
| CN | 104884046 A | 9/2015 |

(Continued)

OTHER PUBLICATIONS

Agid, Y. et al., "Levadopa in the treatment of parkinsons's disease: a consensus meeting," Movement Disorders: Official Journal of the Movement Disorder Society, 1999, vol. 14, No. 6, pp. 911-913.

(Continued)

*Primary Examiner* — Sin J Lee
(74) *Attorney, Agent, or Firm* — Fenwick & West LLP

(57) ABSTRACT

A dry pharmaceutical composition is provided that is suitable for respiratory tract delivery of levodopa and DDI for treatment of Parkinson's disease or Parkinson syndrome. The dry pharmaceutical composition comprises levodopa, a dopa decarboxylase inhibitor (DDI) and at least one excipient. A unit dosage form of the dry pharmaceutical composition and a method of treating a patient with Parkinson's disease or Parkinson syndrome by administering the dry pharmaceutical composition are also provided.

18 Claims, 41 Drawing Sheets

(56) References Cited

U.S. PATENT DOCUMENTS

| | | |
|---|---|---|
| 5,398,850 A | 3/1995 | Sancoff et al. |
| 5,435,282 A | 7/1995 | Haber et al. |
| 5,505,193 A | 4/1996 | Ballini et al. |
| 5,516,006 A | 5/1996 | Meshberg |
| 5,711,488 A | 1/1998 | Lund |
| 5,715,811 A | 2/1998 | Ohki et al. |
| 5,797,390 A | 8/1998 | McSoley |
| 5,814,020 A | 9/1998 | Gross |
| 5,819,730 A | 10/1998 | Stone et al. |
| 5,823,183 A | 10/1998 | Casper et al. |
| 5,881,719 A | 3/1999 | Gottenauer et al. |
| 5,901,703 A | 5/1999 | Ohki et al. |
| 5,906,198 A | 5/1999 | Flickinger |
| 5,910,301 A | 6/1999 | Farr et al. |
| 5,954,696 A | 9/1999 | Ryan |
| 6,062,213 A | 5/2000 | Fuisz et al. |
| 6,092,522 A | 7/2000 | Calvert et al. |
| 6,145,703 A | 11/2000 | Opperman |
| 6,158,676 A | 12/2000 | Hughes |
| 6,180,603 B1 | 1/2001 | Frey |
| 6,186,141 B1 | 2/2001 | Pike et al. |
| 6,189,739 B1 | 2/2001 | von Schuckmann |
| 6,294,153 B1 | 9/2001 | Modi |
| 6,302,101 B1 | 10/2001 | Py |
| 6,313,093 B1 | 11/2001 | Frey |
| 6,347,789 B1 | 2/2002 | Rock |
| 6,367,471 B1 | 4/2002 | Genosar et al. |
| 6,367,473 B1 | 4/2002 | Käfer |
| 6,382,465 B1 | 5/2002 | Perth |
| 6,410,046 B1 | 6/2002 | Lerner |
| 6,491,940 B1 | 12/2002 | Levin |
| 6,514,482 B1 | 2/2003 | Bartus et al. |
| 6,540,983 B1 | 4/2003 | Adjei et al. |
| 6,569,463 B2 | 5/2003 | Patel et al. |
| 6,585,172 B2 | 7/2003 | Arghyris |
| 6,585,957 B1 | 7/2003 | Adjei et al. |
| 6,585,958 B1 | 7/2003 | Keller et al. |
| 6,595,202 B2 | 7/2003 | Calvo |
| 6,622,721 B2 | 9/2003 | Vedrine et al. |
| 6,644,305 B2 | 11/2003 | MacRae et al. |
| 6,644,309 B2 | 11/2003 | Casper et al. |
| 6,647,980 B1 | 11/2003 | Gizurarson |
| 6,681,767 B1 | 1/2004 | Patton et al. |
| 6,684,879 B1 | 2/2004 | Coffee et al. |
| 6,701,916 B2 | 3/2004 | Mezzoli |
| 6,715,485 B1 | 4/2004 | Djupesland |
| 6,734,162 B2 | 5/2004 | Van Antwerp et al. |
| 6,810,872 B1 | 11/2004 | Ohki et al. |
| 6,923,988 B2 | 8/2005 | Patel et al. |
| 7,033,598 B2 | 4/2006 | Lerner |
| 7,051,734 B2 | 5/2006 | Casper et al. |
| 7,163,013 B2 | 1/2007 | Harrison |
| 7,182,277 B2 | 2/2007 | Vedrine et al. |
| 7,200,432 B2 | 4/2007 | Lerner et al. |
| 7,214,209 B2 | 5/2007 | Mazzoni |
| 7,231,919 B2 | 6/2007 | Giroux |
| 7,258,119 B2 | 8/2007 | Mazzoni |
| 7,296,566 B2 | 11/2007 | Alchas |
| 7,347,201 B2 | 3/2008 | Djupesland |
| 7,377,901 B2 | 5/2008 | Djupesland et al. |
| 7,476,689 B2 | 1/2009 | Santus et al. |
| 7,481,218 B2 | 1/2009 | Djupesland |
| 7,543,581 B2 | 6/2009 | Djupesland |
| 7,655,619 B2 | 2/2010 | During et al. |
| 7,740,014 B2 | 6/2010 | Djupesland |
| 7,784,460 B2 | 8/2010 | Djupesland et al. |
| 7,799,337 B2 | 9/2010 | Levin |
| 7,832,394 B2 | 11/2010 | Schechter et al. |
| 7,841,337 B2 | 11/2010 | Djupesland |
| 7,841,338 B2 | 11/2010 | Dunne et al. |
| 7,854,227 B2 | 12/2010 | Djupesland |
| 7,866,316 B2 | 1/2011 | Giroux |
| 7,905,229 B2 | 3/2011 | Giroux et al. |
| 7,934,503 B2 | 5/2011 | Djupesland et al. |
| 7,975,690 B2 | 7/2011 | Djupesland |
| 7,994,197 B2 | 8/2011 | Cook et al. |
| 8,001,963 B2 | 8/2011 | Giroux |
| 8,047,202 B2 | 11/2011 | Djupesland |
| 8,119,639 B2 | 2/2012 | Cook et al. |
| 8,122,881 B2 | 2/2012 | Giroux |
| 8,146,589 B2 | 4/2012 | Djupesland |
| 8,171,929 B2 | 5/2012 | Djupesland et al. |
| 8,327,844 B2 | 12/2012 | Djupesland |
| 8,404,276 B2 | 3/2013 | Jackson et al. |
| 8,408,427 B2 | 4/2013 | Wong |
| 8,448,637 B2 | 5/2013 | Giroux |
| 8,511,303 B2 | 8/2013 | Djupesland |
| 8,517,026 B2 | 8/2013 | Amon |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,596,278 B2 | 12/2013 | Djupesland |
| 8,733,342 B2 | 5/2014 | Giroux et al. |
| 8,757,146 B2 | 6/2014 | Hoekman et al. |
| 8,800,555 B2 | 8/2014 | Djupesland |
| 8,839,790 B2 | 9/2014 | Beck Arnon |
| 8,875,794 B2 | 11/2014 | Carlsen et al. |
| 8,899,229 B2 | 12/2014 | Djupesland et al. |
| 8,899,230 B2 | 12/2014 | Immel |
| 8,910,629 B2 | 12/2014 | Djupesland et al. |
| 8,925,544 B2 | 1/2015 | Flickinger |
| 8,978,647 B2 | 3/2015 | Djupesland et al. |
| 8,987,199 B2 | 3/2015 | Abdel Maksoud et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,101,539 B2 | 8/2015 | Nagata et al. |
| 9,119,932 B2 | 9/2015 | Djupesland |
| 9,180,264 B2 | 11/2015 | Young et al. |
| 9,272,104 B2 | 3/2016 | Djupesland |
| 9,446,207 B2 | 9/2016 | Jung |
| 9,550,036 B2 | 1/2017 | Hoekman et al. |
| 2002/0006443 A1 | 1/2002 | Curatolo et al. |
| 2002/0017294 A1 | 2/2002 | Py |
| 2002/0054856 A1 | 5/2002 | Jones |
| 2002/0092520 A1 | 7/2002 | Casper et al. |
| 2003/0017119 A1 | 1/2003 | Rabinowitz et al. |
| 2003/0158527 A1 | 8/2003 | Mezzoli |
| 2003/0217748 A1 | 11/2003 | Giroux |
| 2004/0068222 A1 | 4/2004 | Brian |
| 2004/0238574 A1 | 12/2004 | Merk et al. |
| 2005/0023376 A1 | 2/2005 | Anderson |
| 2005/0028812 A1 | 2/2005 | Djupesland |
| 2005/0036985 A1 | 2/2005 | Ensoli |
| 2005/0070608 A1 | 3/2005 | Remenar et al. |
| 2005/0098172 A1 | 5/2005 | Anderson |
| 2005/0142072 A1 | 6/2005 | Birch et al. |
| 2005/0274378 A1 | 12/2005 | Bonney et al. |
| 2006/0107957 A1 | 5/2006 | Djupesland |
| 2006/0219813 A1 | 10/2006 | Morrison |
| 2006/0240092 A1 | 10/2006 | Breitenkamp et al. |
| 2007/0056585 A1 | 3/2007 | Davies et al. |
| 2007/0068514 A1 | 3/2007 | Giroux |
| 2007/0074722 A1 | 4/2007 | Giroux et al. |
| 2007/0119451 A1 | 5/2007 | Wang et al. |
| 2007/0131224 A1 | 6/2007 | Giroux |
| 2007/0172517 A1 | 7/2007 | Sasson et al. |
| 2007/0202051 A1 | 8/2007 | Schuschnig |
| 2007/0298010 A1 | 12/2007 | Maggio |
| 2008/0054099 A1 | 3/2008 | Giroux et al. |
| 2008/0163874 A1 | 7/2008 | Djupesland |
| 2008/0178871 A1 | 7/2008 | Genova et al. |
| 2008/0233163 A1 | 9/2008 | Assaf |
| 2008/0305077 A1 | 12/2008 | Frey et al. |
| 2009/0028938 A1 | 1/2009 | Berndl et al. |
| 2009/0320832 A1 | 12/2009 | Djupestand |
| 2010/0298268 A1 | 11/2010 | Hsu et al. |
| 2011/0053859 A1 | 3/2011 | Deadwyler et al. |
| 2011/0151008 A1 | 6/2011 | Jackson et al. |
| 2011/0301150 A1 | 12/2011 | Park et al. |
| 2012/0195959 A1 | 8/2012 | Ishii |
| 2013/0331399 A1 | 12/2013 | Leahy et al. |

(56) References Cited

U.S. PATENT DOCUMENTS

| | | |
|---|---|---|
| 2014/0083424 A1 | 3/2014 | Hoekman et al. |
| 2014/0170220 A1 | 6/2014 | Cartt et al. |
| 2014/0343494 A1 | 11/2014 | Hoekman et al. |
| 2015/0057287 A1 | 2/2015 | Cook et al. |
| 2015/0216823 A1 | 8/2015 | Chatterjee |
| 2015/0258178 A1 | 9/2015 | Gong |
| 2015/0335712 A1 | 11/2015 | Brown et al. |
| 2016/0101245 A1 | 4/2016 | Hoekman et al. |
| 2016/0228433 A1 | 8/2016 | Haruta et al. |
| 2016/0296591 A1 | 10/2016 | Franklin |
| 2018/0200186 A1 | 7/2018 | Chen et al. |
| 2018/0243250 A1* | 8/2018 | Bolsöy .............. G01N 33/9413 |

FOREIGN PATENT DOCUMENTS

| | | |
|---|---|---|
| CN | 106659685 A | 5/2017 |
| DE | 19518580 A1 | 11/1996 |
| DE | 102013100473 A1 | 7/2014 |
| EP | 1165044 A2 | 1/2002 |
| GB | 806284 A | 12/1958 |
| GB | 1517642 A | 7/1978 |
| JP | H08322934 A | 12/1996 |
| RU | 2545734 C1 | 4/2015 |
| WO | WO 1986/001731 A1 | 3/1986 |
| WO | WO 1999/013930 A1 | 3/1999 |
| WO | WO 2000/054887 A1 | 9/2000 |
| WO | WO 2001/036033 A2 | 5/2001 |
| WO | WO 2002/009707 A1 | 2/2002 |
| WO | WO 2007/012853 A1 | 2/2007 |
| WO | WO 2008/059385 A2 | 5/2008 |
| WO | WO 2011/143721 A1 | 5/2010 |
| WO | WO 2011/047412 A1 | 4/2011 |
| WO | WO 2012/066319 A1 | 5/2012 |
| WO | WO 2015/163840 A1 | 10/2015 |
| WO | WO 2017/176652 A2 | 10/2017 |

OTHER PUBLICATIONS

Anderson, B.M. et al., "Oral delivery of [D-Leu-4]-OB3 and MA-[D-Leu-4]-OB3, synthetic peptide leptin mimetics: Immunofluorescent localization in the mouse hypothalamus," Brain Research, 2017, vol. 1664, pp. 1-8.

Andreu, N. et al., "L-dopa-induced sedation: A double-blind crossover controlled study versus triazolam and placebo inhealthy volunteers," Clinical Neuropharmacology, 1999, vol. 22, No. 1, pp. 5-23.

Anonymous. "History of Changes for Study: NCT03541356: Therapeutic Potential for Intranasal Levodopa in Parkinson's Disease—Off Rehearsal (THOR201)." ClinicalTrials.gov, Sponsor: Impel NeuroPharma Inc., May 17, 2018, pp. 1-11.

Apokyn Apomorphine hydrochloride injection, US Food and Drug Administration Product Information, Mar. 2017, [Online][Retrieved Mar. 13, 2019], Retrieved from the internet: <URL: https://www.accessdata.fda.gov/drugsatfda_docs/label/2017/021264s014lbl.pdf>.

Apomine Solution for Infusion Product Information, Therapeutic Goods Administration, Australia, Aug. 2016, [Online][Retrieved Mar. 2019], Retrieved from the internet: <URL: https://www.ebs.tga.gov.au/ebs/picmi/picmirepository.nsf/pdf?OpenAgent&id=CP-2016-PI-02544-1>, 15 pages.

Appasaheb, et al., "Review on Intranasal Drug Delilvery System", Journal of Advanced Pharmacy Education and Research, vol. 3, Issue 4, Oct. 2013, 14 pages.

Baron, "Orally Inhaled Dihydroergotamine; Reviving and Improving a Classic", Future Neurology, May 2011, 11 pages.

Barthelmebs, M. et al., "Renal dopamine in healthy volunteers after oral ingestion of l-Dopa," Fundamental & Clinical Pharmacology, 1993, vol. 7, No. 1, pp. 11-16.

Bartos, C. et al. "Formulation of Levodopa Containing Dry Powder for Nasal Delivery Applying the Quality-by-Design Approach." European Journal of Pharmaceutical Science, vol. 123, No. 1, Oct. 15, 2018, pp. 475-483.

Bowen, P. "Particle Size Distribution Measurement from Millimeters to Nanometers and from Rods to Platelets." Journal of Dispersion Science and Technology, vol. 23, No. 5, Jan. 1, 2002, pp. 631-662.

Bredberg, E. et al., "Pharmacokinetics of L-dopa and carbidopa in rats following different routes of administration," Pharmaceutical Research, 1994, vol. 11, No. 4, pp. 549-555.

Brime, B. et al., "Preparation and in vitro characterization of gelatin microspheres containing Levodopa for nasal administration," Journal of Microencapsulation, 2000, vol. 17, No. 6, pp. 777-784.

Burch, D. et al. "Parkinsons disease," Lancet, 2005, vol. 365, No. 9459, pp. 622-627.

Chandrakala, V. et al. "Optimization and Characterisation of Nasal Microparticles for Levodopa Delivery to CNS." Research Journal of Pharmaceutical, Biological and Chemical Sciences, vol. 4, No. 2, Apr.-Jun. 2013, pp. 882-898.

Chao, O.Y., "Intranasally applied L-dopa alleviates parkinsonian symptoms in rats with unilateral nigro-striatal 6-OHDA lesions," Brain Research Bulletin, 2012, vol. 87, No. 2-3, pp. 340-345.

Chao, S. "Preparation of Levodopa CMS-Na Microspheres Used in Nasal." Master's Thesis of Yanbian University, May 20, 2010, pp. 1, 14, and 23.

Chinese Patent Office, Office Action, Chinese Patent Application No. 201980016881.7, dated Jan. 19, 2022, 15 pages.

Chun, K. et al., "Design and Evaluation of Levodopa Methyl Ester Intranasal Delivery Systems," Journal of Parkinson's Disease, 2011, vol. 11, pp. 101-107.

Clinical Trials.gov. "Therapeutic Potential for Intranasal Levodopa in Parkinson's Disease—Off Reversal." Trial Record for: NCT03541356, Sponsor: Impel NeuroPharma Inc., May 30, 2018, pp. 1-12.

Constantino, et al., "Intranasal administration of acetylcholinesterase inhibitors", BMC Neuroscience, Dec. 10, 2008, 3 pages.

Da Prada, M. et al., "The pharmacology of Parkinson's disease: basic aspects and recent advances," Experientia, 1984, vol. 40, No. 11, pp. 1165-1304.

De Rijk, M.C.D., et al., "Prevalence of parkinsonism and Parkinson's disease in Europe: The Europarkinson collaborative study," Journal of Neurology, Neurosurgery and Psychiatry, 1997, vol. 62, No. 1, pp. 10-15.

Delong, M. et al., "Dose Delivery Characteristics of the AIR Pulmonary Delivery System Over a Range of Inspiratory Flow Rates," Journal of Aerosol Medicine, 2005, vol. 18, No. 4, pp. 452-459.

Devries, M.H. et al., "Decarboxylation of L-dopa in the rat isolated vascularly perfused small intestine: contribution to systemic elimination and dose-dependent first pass effect," Journal of Pharmacy and Pharmacology, 1992, vol. 44, No. 4, pp. 311-314.

EP Office Action for 14727320.5, dated Nov. 9, 2016, 6 pages.

EP Search Report for 09707800.0 dated Jul. 1, 2015, 12 pages.

EP Search Report for 11818832.5 dated Sep. 24, 2014, 6 pages.

European Medicines Agency, "EPAR Scientific Discussion for the approval of Stalevo," 2004, [Online][Retrieved Mar. 13, 2019], Retrieved from the internet: <URL:http://www.ema.europa.eu/docs/en_GB/document_library/EPAR_Scientific_Discussion/human/000511/WC500057480.pdf>.

European Patent Office, Extended European Search Report, European Patent Application No. 19838654.2, dated Mar. 4, 2022, 10 pages.

European Patent Office, Extended European Search Report, European Patent Application No. 19735763.5, dated Sep. 2, 2021, 16 pages.

FDA Inactive Ingredient Search for Approved Drug Products Database, "Inactive Ingredient Search for Approved Drug Products," [Online][Retrieved Mar. 11, 2019], Retrieved from the internet: <https://www.accessdata.fda.gov/scripts/cder/iig/index.cfm>.

FDA Select Committee on GRAS substances (SCOGS) Opinion: Cellulose, microcrystalline cellulose. SCOGS Report No. 25. Year of report 1973. https://www.fda.gov/Food/IngredientsPackagingLabeling/GRAS/SCOGS/ucm261287.htm.

FDA Select Committee on GRAS substances (SCOGS) Opinion: hydroxypropylmethyl cellulose. SCOGS Report No. 25. Year of report 1973.

(56) References Cited

OTHER PUBLICATIONS

Ghodke, D. S. et al. "Preparation, Characterization and In Vitro Evaluation of Stable Mucoadhesive Intranasal Microsphere of L-Dopa." Latin American Journal of Pharmacy, vol. 30, No. 7, Jun. 4, 2011, pp. 1414-1422.

Gizurarson, S., "Anatomical and histological factors affecting intranasal drug and vaccine delivery," Current Drug Delivery, 2012, vol. 9, No. 6, pp. 566-582.

Glatt, H. et al., "Endogenous mutagens derived from amino acids," Mutation Research/Reviews in Genetic Toxicology, 1990, vol. 238, No. 3, pp. 235-243.

Gordon, M.M. et al., "Intravenous Levodopa administration in humans based on a two-compartment kinetic model," Journal of Neuroscience Methods, 2007, vol. 159, No. 2, pp. 300-307.

Grahnen, A. et al., "Comparative multiple-dose pharmacokinetics of controlled-release Levadopa products," European Neurology, 1992, vol. 32, No. 6, pp. 343-348.

Grange, S. et al., "A Pharmacokinetic model to predict the PK interaction of L-dopa and benserazide in rats," Pharmaceutical Research, 2001, vol. 18, No. 8, pp. 1174-1184.

GRAS Notification—Citrus Fiber (CitriTexR Citrus Fiber), Dow Chemical Company Submission of GRAS Notification for hydroxypropyl methylcellulose to US FDA. Tox Strategies, Sep. 2006, 139 pages.

Gross, E.A. et al., "Comparative morphometry of the nasal cavity in rats and mice," Journal of Anatomy, 1982, vol. 135, No. 1, pp. 83-88.

Hanson, et al., "Intranasal delivery of growth differentiation factor 5 to the central nervous system", Drug Delivery, 19(3):149-54, Feb. 2012, 7 pages.

Hardie, R.J. et al., "The pharmacokinetics of intravenous and oral L-dopa in patients with Parkinson's disease who exhibit ON-OFF fluctuations," British Journal of Clinical Pharmacology, 1986, vol. 22, No. 4, pp. 429-436.

Harris, A.J. et al., "Determination of surface areas, volumes, and lengths of cynomolgus monkey nasal cavities by ex vivo magnetic resonance imaging," Journal of Aerosol Medicine, 2003, vol. 16, No. 2, pp. 99-105.

Hinz, M. et al., "Parkinson's disease: carbidopa, nausea and dyskinesia," Clinical Pharmacology: Advances and Applications, 2014, vol. 6, pp. 189-194.

Hoekman, J.D., "The Impact of Enhanced Olfactory Deposition and Retention on Direct Nose-to-Brain Drug Delivery", UMI Dissertation Publishing, Apr. 11, 2011, 181 pages.

Hoffmann-La Roche Limited, "Prolopa Product Monograph," Health Canada, L-dopa and benserazide combination capsules, Mar. 2016, [Online][Retrieved Mar. 14, 2019], Retrieved from <URL https://pdf.hres.ca/dpd_pm/00034100.PDF>.

Impel Neuropharma, "POD Technology," Dec. 13, 2017, [Online], Retrieved on Feb. 14, 2019, Retrieved from the internet: <URL: http://web.archive.org/web/20171213054754/http:/limpetno.com/pod-technology>, 3 pages.

International Search Report for PCT/US/2009/033468 dated Dec. 2, 2009, 5 pages.

Iwawaki, H.M. et al., "Effects of L-ascorbic acid on the clastogenicity of catecholamines," Mutation Research, 1988, vol. 203, pp. 374-379.

Juncos, J.L., "Levodopa: Pharmacology, pharmacokinetics and pharmacodynamics," Neurologic clinics, 1992, vol. 10, No. 2, pp. 487-509.

Kammermeier, M. et al., "Cardiotoxicity of catecholamines after application of L-dopa in wistar-kyoto (WKY) and spontaneously hypertensive rats (SHR)," Hypertension Research, 1995, 18, no. Supplement1, pp. S165-S168.

Kim, T.K et al., "Pharmacokinetic evaluation and modeling of formulated levodopa intranasal delivery systems," European Journal of Pharmaceutical Sciences, 2009, vol. 39, pp. 525-532.

Kimber, T.E., et al., "An update on Parkinson's disease.," Modern Medicine of Australia, 1998, vol. 41, No. 9, pp. 22-32.

Kitamura, J. et al., "Genetic toxicity of several antihypertensive drugs possessing a hydrazine group," Research Communications in Chemical Pathology and Pharmacology, 1985, vol. 49, No. 3, pp. 415-422.

Kordower, J.H. et al., "The first miracle in neurodegenerative disease: The discovery of oral levadopa," Brain Research Bulletin, 1999, vol. 5, No. 50, pp. 377-378.

Kumar, et al., "Nasal Drug Delivery: A Potential Route for Brain Targeting" The Pharma Innovation Journal, vol. 2, No. 1, Mar. 2013. 9 pages.

Lechuga, D. et al., "Advances in Respiratory and Nasal Drug Delivery," Molecular Pharmaceutics, Aug. 3, 2015, Special Issue: Advances in Respiratory and Nasal Drug Delivery, vol. 12, pp. 2561.

Lee, J.J, "Changes in endogenous monoamines in aged rats," Clinical and Experimental Pharmacology and Physiology, 2001, vol. 28, No. 4, pp. 285-289.

Lee, Y.H. et al., "Pharmacokinetic evaluation of formulated levodopa methyl ester nasal delivery systems," Eur J Drug Metab Pharmacokinet, 2014, vol. 39, pp. 237-242.

Lewitt, P.A. et al. "Inhaled levodopa (CVT-301, 84 mg dose) significantly improves motor function during OFF periods in Parkinson's disease subjects: A Phase 3 study [SPAN-PD™]," 21st International Congress of Parkinson's Disease and Movement Disorders, Jun. 2017, Vancouver, Canada, 2 pages.

Lewitt, P.A. et al., "A randomized trial of inhaled L-dopa (CVT-301) for motor fluctuations in Parkinson's disease," Movement Disorders, 2016, vol. 31, No. 9, pp. 1356-1365.

Lewitt, P.A. et al., "Safety and efficacy of CVT-301 (levodopa inhalation powder) on motor function during off periods in patients with Parkinson's disease: a randomized, double-blind, placebo-controlled phase 3 trial," The Lancet, Feb. 2019, vol. 18, pp. 145-154.

Lipp, M.M. et al., "Preclinical and clinical assessment of inhaled levodopa for OFF episodes in Parkinson's disease," Science Translational Medicine, 2016, vol. 8, pp. 1-10.

Lochhead, J.J et al., "Intranasal delivery of biologies to the central nervous system," Advanced Drug Delivery Reviews, 2012, vol. 64, No. 7, pp.

Luinstra, M et al., "Can Patients with Parkinson's Disease Use Dry Powder Inhalers during Off Periods?," PLoS One, Jul. 14, 2015, vol. 10, No. 7, 12 pages.

Luinstra, M. et al., "A levodopa dry powder inhaler for the treatment of Parkinson's disease patients in off periods," European Journal of Pharmaceutics and Biopharmaceutics, 2015, vol. 97, pp. 22-29.

Maggio, E.T. et al., "Absorption enhancement: Highly bioavailable nasal calcitonin—Potential for expanded use in analgesia," Drug Delivery Technology, 2010, vol. 10, No. 1, 5 pages.

Maggio, E.T., "Absorption enhancing excipients in systemic nasal drug delivery," Journal of Excipients and Food Chemistry, 2014, vol. 5, No. 2, pp. 1-13.

McGregor, D.B. et al., "Reactivity of catecholamines and related substances in the mouse lymphoma L5178Y cell assay for mutagens," Environmental and Molecular Mutagenesis, 1988, vol. 11, No. 4, pp. 523-544.

Mearrick, P.T. et al., "The role of the liver in the clearance of L-dopa from plasma," Journal of Pharmacokinetics and Biopharmaceutics, 1975, vol. 3, No. 1, pp. 13-23.

Melamed, E., "Early-morning dystonia. A late side effect of long-term L-dopa therapy in parkinsons's disease," Archives of Neurology, 1979, vol. 36, No. 5, pp. 308-310.

Movapo, "Movapo® Apomorphine hydrochloride," Therapeutic Goods Administration, Australia, Product Information, Oct. 2017, [Online][Retrieved Mar. 14, 2019], Retrieved from <URL: https://www.ebs.tga.gov.au/ebs/picmi/picmirepository.nsf/pdf?OpenAgent&id=CP-2015-PI-02955-1>.

Muangpaisan, W. et al., "A systematic review of the worldwide prevalence and incidence of parkinson's disease," Journal of the Medical Association of Thailand, 2011, vol. 94, No. 6, pp. 749-755.

Munjal, S, et al., "A randomized trail comparing the pharmacokinetics, safety and tolerability of DFN-02 and intranasal sumatriptan spray containing a permeation enhancer, with intranasal and sub-

(56) References Cited

OTHER PUBLICATIONS cutaneous sumatriptan in healthy adults," Headache: The Journal of Head and Face Pain, 2016, vol. 56, No. 9, pp. 1455-1465.
Nivakovic, Z.M. et al., "Myristic acid conjugation of [D-Leu-4]-OB3, a biologically active leptin-related synthetic peptide amide, significantly improves its pharmacokinetic profile and efficacy," Peptides, 2014, vol. 62, pp. 176-182.
Novartis, "Stalevo (L-dopa, carbidopa, entacapone)," Food and Drug Administration Product Information, Last updated Feb. 2016, [Online][Retrieved Mar. 14, 2019], Retrieved from: <URL: https://www.accessdata.fda.gov/drugsatfda_docs/label/2016/021485s033lbl.pdf>.
Nutt, J.G. et al., "Pharmacokinetics of Levadopa," Clinical Neuropharmacology, 1984, vol. 7, No. 1, pp. 35-49.
Obeso, J.A. et al., "Levodopa motor complications in Parkinson's disease," Trends in Neuroscience, 2000, vol. 23, pp. S2-S7.
Ozsoy, et al., "Nasal Delivery of High Molecular Weight Drugs", Molecules Journal, Sep. 23, 2009, 26 pages.
Pappert, E.J. et al., "Treatment of OFF episodes in Parkinson's disease: An evaluation of physician practices," [abstract], Movement Disorder, 2016, vol. 31, No. Suppl 2, 1 page, [Online][Retrieved Mar. 14, 2019], Retrieved from <http://www.mdsabstracts.org/abstract/treatment-of-off-episodes-in-parkinsons-disease-an-evaluation-of-physician-practices/.>.
Parvathi, "Intranasal Drug Delivery to Brain: An Overview," published in the International Journal of Research in Pharmacy and Chemistry 2012, 2(3), 7 pages.
PCT International Search Report and Written Opinion, PCT Application No. PCT/US2019/42689, dated Oct. 24, 2019, 14 pages.
PCT Search Report and Written Opinion dated Mar. 27, 2012 for PCT application No. PCT/US2011/048435, 14 pages.
Pellegrini, C. et al., "Effects of L-dopa/benserazide co-treatment on colonic excitatory cholinergic motility and enteric inflammation following dopaminergic nigrostriatal neurodegeneration," Neuropharmacology, 2017, vol. 123, pp. 22-33.
Renner, et al., "Intranasal delivery of growth differentiation factor 5 to the central nervous system," Drug Delivery, Feb. 2012, 7 pages.
Roche, "Madopar (levodopa and benserazide)," Therapeutic Goods Administration Product Information, Dec. 2016, [Online][Retrieved Mar. 14, 2019], Retrieved from: <URL: https://www.ebs.tga.gov.au/ebs/picmi/picmirepository.nsf/pdf?OpenAgent&id=CP-2010-PI-02391-3&d=20171102161114622483>.
Rose, S.P. et al., "Peripheral pharmacokinetic handling and metabolism of L-dopa in the rat: the effect of route of administration and carbidopa pretreatment," Journal of Pharmacy and Pharmacology, 1991, vol. 43, No. 5, pp. 325-330.
Samii, A. et al. "Parkinson's disease," The Lancet, 2004, vol. 363, No. 9423, pp. 1783-1793.
Saral, A. M. et al. "Bootstrap Confidence Interval Approach to Compare Bioavailability of Nasal Levodopa Microspheres vs Intranasal Levodopa Carbidopa Formulation in Brain." J. Indian Chem. Soc., vol. 92, Apr. 2015, pp. 514-517.
Sato, S. et al., "Pharmacokinetic and pharmacodynamic studies of L-dopa in rats. I. Pharmacokinetic analysis of L-dopa in rat plasma and striatum," Biological and Pharmaceutical Bulletin, 1994, vol. 17, No. 12, pp. 1616-1621.
Schapira, A.H.V. et al., "Present and future drug treatment for Parkinson's disease," Journal of Neurology, Neurosurgery and Psychiatry, 2005, vol. 76, No. 11, pp. 1472-1478.
Sharma, S. et al., "Formulation and characterization of intranasal mucoadhesive nanoparticulates and thermos-reversible gel of levodopa for brain delivery," Drug Development and Industrial Pharmacy, 2014, vol. 40, No. 7, pp. 869-878.
Sinemet CR Sustained-Release Tablets, Mylan Pharmaceuticals, Inc., Jul. 2014, 12 pages.
Stacy, M. et al., "Apomorphine for the acute treatment of OFF episodes in Parkinson's disease," Parkinsonism and Related Disorders, 2008, vol. 14, No. 2, 8 pages.
Stevens, et al., "Systemic and Direct Nose-to-Brain Transport Pharmacokinetic Model for Remoxipride after Intravenous and Intranasal Administration", in "Drug Metabolism and Disposition", The American Society for Pharmacology and Experimental Therapeutics, 2011, vol. 39, No. 12, 8 pages.
Submission of GRAS Notification for Alkyl Polyglycoside Surfactants, Cognis Corporation to US FDA, Nov. 2007, 81 pages.
Suter, W. et al., "Genotoxicity of apomorphine and various catecholamines in the *Salmonella* mutagenicity test (Ames test) and in tests for primary DNA damage using DNA repair-deficient B. subtilis strains (Rec assay)," Mutation research, 1984, vol. 137, No. 1, pp. 17-28.
Talegaonkar, et al., "Intranasal delivery: an approach to bypass the blook brain barrier", Indian J Pharmacol, Jun. 2004, vol. 36, Issue 3, 8 pages.
Tolosa, E. et al., "History of levodopa and dopamine agonists in Parkinson's disease treatment," Neurology, 1998, vol. 50, No. 6 Suppl 6, pp. S2-S10.
US FDA, "Sinemet (carbidopa, L-dopa)," US Food and Drug Administration Product Information, Jul. 2014, [Online][Retrieved Mar. 14, 2019], Retrieved from <URL: https://www.accessdata.fda.gov/drugsatfda_docs/label/2014/017555s056s068s071lbl.pdf>.
Vasa, D. M. et al. "Improved Flux of Levodopa via Direct Deposition of Solid Microparticles on Nasal Tissue." AAPS PharmSciTech, vol. 18, No. 3, Apr. 2017, pp. 904-912.
Von Campenhausen, S. et al., "Prevalence and incidence of parkinsons's disease in Europe," European Neuropsychopharmacology, 2005, vol. 15, No. 4, pp. 473-490.
Weber, N. et al., "Metabolism of orally administered alkyl β-glycosides in the mouse," The Journal of Nutrition, 1984, vol. 114, No. 2, pp. 247-254.
Westin et al, "Direct Nose to Brain Transfer of Morphine After Nasal Administration to Rats", Pharmaceutical Research, vol. 23, No. 3, Mar. 2006, 8 pgs.
Westin, "Olfactory Tranfser of Analgesic Drugs After Nasal Administration", Digital Comprehensive Summaries of Uppsala Dissertations from the Faculty of Pharmacy 55, May 11, 2007, 66 pages.
Wood-Kaczmar, A. et al., "Understanding the molecular causes of Parkinson's disease," Trends in Molecular Medicine, 2006, vol. 12, No. 11, pp. 521-528.
World Health Organization. "Safety evaluation of certain food additives and contaminants," Microcrystalline cellulose WHO Food Additives Series 40. Performed at the forty-ninth meeting of the Joint FAO/WHO Expert Committee on Food Additives, WHO, Geneva, 1998. [Online][Retrieved Mar. 14, 2019], Retrieved from <URL:http://www.inchem.org/documents/jecfa/jecmono/v040je03.htm>.
Xadago Prescribing Information, US WorldMeds, LLC, 2017, 24 pages.
Yamada, et al., "Nose-to-brain delivery of TS-002, prostaglandin D2 analogue", Journal of Drug Targeting, Jan. 2007, 9 pages.
Yaylagul, E.O. et al., "In vivo protective effect of uridine, a pyrimidine nucleoside, on genotoxicity induced by Levodopa/carbidopa in mice," Food and Chemical Toxicology, 2015, vol. 82, pp. 36-41.
Yimam, et al., "Effects of lipid association on lomustine (CCNU) administered intracerebrally to syngeneic 36B-10 rat brain tumors", Cancer Letters 244(2), Dec. 2006, 9 pages.
Ying, "The nose may help the brain: intranasal drug delivery for treating neurological diseases" Future Medecine, 3(1), Jan. 2008, 4 pages.
Zhang, et al, "The brain targeting efficiency following nasally applied MPEG-PLA nanoparticles in rats", Journal of Drug Targeting, Jun. 2006, 11 pages.
Zwickey, R.E. et al., "Preclinical toxicological studies of carbidopa and combinations of carbidopa and L-dopa," Toxicology and Applied Pharmacology, 1974, vol. 29, No. 2, pp. 181-195.

\* cited by examiner

SECTION A-A

RESPIRATORY TRACT DELIVERY OF LEVODOPA AND DOPA DECARBOXYLASE INHIBITOR FOR TREATMENT OF PARKINSON'S DISEASE

1. CROSS-REFERENCE TO RELATED APPLICATIONS

This application is a division of co-pending U.S. application Ser. No. 16/517,423, filed Jul. 19, 2019, which claims priority to U.S. Provisional Application Nos. 62/700,584, filed Jul. 19, 2018, and 62/820,244, filed Mar. 18, 2019, each of which is incorporated herein by reference in its entirety.

2. BACKGROUND

Parkinson's Disease (PD) is a neurodegenerative disorder marked by loss of dopaminergic neurons in the substantia nigra. Patients present early in the course of the disease with motor symptoms, including tremor or shaking, rigidity, slowness of movement, and difficulty in walking. The motor symptoms are collectively called Parkinson syndrome. Although Parkinson's disease is the most common cause of Parkinson syndrome, Parkinson syndrome can also result from various toxic insults.

Oral treatment with L-DOPA ("levodopa") in combination with a peripherally acting DOPA decarboxylase inhibitor ("DDI") is the cornerstone of treatment during the early stages of PD and treatment of Parkinson syndrome. However, absorption after oral administration is highly variable, leading to variations in plasma and brain levels. Fluctuations in brain concentration are believed to contribute to fluctuations in motor function, termed ON periods when the motor symptoms of the disease are well controlled and OFF episodes when the motor symptoms of the disease are poorly controlled, and to contribute to the development of disabling dyskinesias. In addition, as motor function deteriorates with disease progression, PD patients can experience dysphagia; in these patients, difficulty in swallowing makes oral ingestion of levodopa increasingly difficult. There is, therefore, a need for alternative routes of levodopa administration.

There are emerging alternatives for parenteral administration of levodopa. For example, pulmonary delivery of levodopa by oral inhalation has recently been approved (Inbrija, Acorda), and there have been various investigations of intranasal levodopa administration (INP103, Impel Neuropharma). In each case, however, levodopa absorption has required concomitant oral administration of a peripherally active DOPA decarboxylase inhibitor, and these approaches have therefore focused on parenteral administration of levodopa for treatment of OFF episodes as an adjunct to baseline treatment with oral levodopa/DDI. There is, therefore, a continuing need for methods of parenteral administration of levodopa that do not require adjunctive treatment with an oral DDI.

3. SUMMARY

We have demonstrated in 2 animal species that DOPA decarboxylase inhibitors can be delivered to the respiratory tract in amounts effective to permit rapid and reproducible absorption of therapeutic amounts of levodopa administered in combination, for the first time obviating the need for adjunctive administration of oral DDI during intranasal and pulmonary administration of levodopa.

Accordingly, in a first aspect, a dry pharmaceutical composition is provided that is suitable for respiratory tract delivery of levodopa and DDI for treatment of Parkinson's disease or Parkinson syndrome. The dry pharmaceutical composition comprises levodopa, a dopa decarboxylase inhibitor (DDI), and at least one excipient.

Respiratory tract delivery can be affected by intranasal administration or administration by oral inhalation. Oral inhalation is used synonymously herein with pulmonary administration.

In some embodiments, levodopa and DDI form a plurality of particles in the powder, wherein each of the plurality of particles comprises levodopa, DDI, or both.

In some embodiments, the median diameter of the plurality of particles (D50) is 1 μm-500 μm, 1 μm-250 μm, 1 μm-100 μm, 1 μm-75 μm, 1 μm-50 μm, 1 μm-40 μm, 1 μm 1 μm-3 μm, 10 μm-40 μm, 10 μm-30 μm, 20 μm-40 μm, or 15 μm-35 μm.

In some embodiments, the plurality of particles are in a crystalline or amorphous form. In some embodiments, the plurality of particles are in amorphous form. In some embodiments, the plurality of particles are obtained by spray-drying. In some embodiments, the plurality of particles are in a partially crystalline and partially amorphous form.

In typical embodiments, the dry pharmaceutical composition comprises no more than 95 wt % levodopa. In some embodiments, the dry pharmaceutical composition comprises no more than 80 wt % levodopa. In some embodiments, the composition comprises 50-80 wt % levodopa, 50-70 wt % levodopa, or 65-70 wt % levodopa.

In typical embodiments, the DDI is carbidopa or benserazide. In some embodiments, the DDI is carbidopa. In some embodiments, the DDI is benserazide.

In typical embodiments, the dry pharmaceutical composition comprises no more than 30 wt % DDI. In some embodiments, the composition comprises 5-30 wt % DDI. In some embodiments, the composition comprises 5-20 wt % DDI. In some embodiments, the composition comprises 8-25 wt % DDI. In some embodiments, the composition comprises 5-15 wt % DDI.

The weight ratio between levodopa and the DDI in the dry pharmaceutical composition can be between 1:1 and 12:1. In some embodiments, the weight ratio between levodopa and the DDI is between 1:1 and 2:1, 2:1 or 1:1. In some embodiments, the weight ratio between levodopa and the DDI is between 3:1 and 12:1. In some embodiments, the weight ratio between levodopa and the DDI is between 4:1 and 11:1, 10:1 or 4:1.

In some embodiments, the dry pharmaceutical composition further comprises a nonionic surfactant. The nonionic surfactant can be an alkyl maltoside. The alkyl maltoside can be n-dodecyl β-D-maltoside. The nonionic surfactant can be present at 0.1-10 wt %, 1-5 wt %, 0.8-5 wt %, 0.9-1 wt %, or 1 wt %.

In some embodiments, the dry pharmaceutical composition further comprises HPMC. In some embodiments, the dry pharmaceutical composition further comprises DSPC. In some embodiments, the dry pharmaceutical composition further comprises a salt of a monovalent inorganic cation. In a preferred embodiment, the salt is NaCl. In some embodiments, the dry pharmaceutical composition comprises 1-5 wt % NaCl, 1-3 wt % NaCl, or 2-4 wt % NaCl.

In some embodiments, the dry pharmaceutical composition comprises 68 wt % levodopa, 2 wt % NaCl, 7 wt % benserazide, 16 wt % HPMC, and 7 wt % DSPC. In some embodiments, the dry pharmaceutical composition comprises 68 wt % levodopa, 2 wt % NaCl, 6.8 wt % carbidopa, 22.2 wt % HPMC, and 1% n-dodecyl β-D-maltoside. In some embodiments, the dry pharmaceutical composition comprises 63.35 wt % levodopa, 1.86 wt % NaCl, 6.34 wt % carbidopa, 27.02 wt % HPMC, and 0.93% n-dodecyl β-D-maltoside. In some embodiments, the dry pharmaceutical composition is a spray dried composition.

In some embodiments, the delivery to the respiratory tract is effected by intranasal administration. In some embodiments, delivery is to the upper respiratory tract, lower respiratory tract, or both.

In some embodiments, the dry pharmaceutical composition is in a container for a delivery device. The container can be a capsule encapsulating the dry pharmaceutical composition. The delivery device can be an intranasal administration device or an oral inhaler. In some embodiments, the delivery device is a handheld, manually actuated, metered-dose administration device. In some embodiments, the delivery device is a manually actuated, propellant-driven, metered-dose administration device. In some embodiments, the delivery device is a breath-actuated inhaler.

In another aspect, a unit dosage for containing the dry pharmaceutical composition is provided. In some embodiments, the unit dosage form contains 25-150 mg of levodopa, 35-140 mg of levodopa, 35 mg of levodopa, 50 mg of levodopa, 70 mg of levodopa, 100 mg of levodopa, or 140 mg of levodopa. In some embodiments, the unit dosage is individually encapsulated in a capsule.

In yet another aspect, a method of treating a patient with Parkinson's disease (PD) or a Parkinson syndrome is provided. The method comprises the step of delivering an effective amount of the dry pharmaceutical composition via the patient's respiratory tract.

The step of delivering can comprise intranasal administration or oral inhalation.

The patient can have PD, or a Parkinson syndrome, selected from post-encephalitic parkinsonism, symptomatic parkinsonism following carbon monoxide intoxication, or symptomatic parkinsonism following manganese intoxication.

In some embodiments, the patient is also being treated with an oral DDI. In some embodiments, the patient is also being treated with an oral DDI and oral levodopa. In some embodiments, the patient is not being treated with an oral DDI and oral levodopa.

In some embodiments, the step of delivering is performed when the patient is experiencing an OFF episode.

In some embodiments, the effective dose is a dose of levodopa effective to reverse the OFF episode within 60 minutes. The effective dose can be sufficient to provide, following administration, (a) a mean peak plasma levodopa concentration ($C_{max}$) of at least 200-400 ng/mL, with (b) a mean time to $C_{max}$ ($T_{max}$) of levodopa of less than 60 minutes.

In some embodiments, the effective dose is 25-150 mg levodopa, 35-140 mg levodopa, 35 mg levodopa, 50 mg levodopa, 70 mg levodopa, 100 mg levodopa, or 140 mg levodopa.

In some embodiments, the effective dose is administered as a single undivided dose. In some embodiments, the effective dose is administered as a plurality of equally divided sub-doses.

The step of delivering can be performed using a delivery device, wherein the delivery device is an intranasal administration device or an oral inhalation administration device. In some embodiments, the delivery device is a handheld, manually actuated, metered-dose administration device. In some embodiments, the delivery device is a manually actu-ated, propellant-driven, metered-dose administration device. In some embodiments, the delivery device is a breath-actuated inhaler.

Other features and advantages of the present disclosure will become apparent from the following detailed description, including the drawings. It should be understood, however, that the detailed description and the specific examples are provided for illustration only, because various changes and modifications within the spirit and scope of the invention will become apparent to those skilled in the art from the detailed description.

4. BRIEF DESCRIPTION OF THE DRAWINGS

FIG. 1 shows mean Plasma Concentration-Time Curves following intranasal administration of the indicated amounts of L-DOPA powder delivered by the nonhuman primate Precision Olfactory Delivery ("nhpPOD") Device. The data were obtained in study number 2037-003, described in Example 1 below.

FIG. 2 shows mean Plasma Concentration-Time Curves following intranasal administration of 20 mg L-DOPA (various formulations) delivered by nhpPOD Device in monkeys pre-dosed orally with the DOPA decarboxylase inhibitor, benserazide. The data were obtained in study 2037-004, described in Example 1 below. The 20 mg bulk L-DOPA (black line) data are drawn from prior Study 2037-003 and are shown for comparison of the measured plasma levels in the absence of oral benserazide.

FIGS. 3A and 3B show mean Plasma Concentration-Time Curves following intranasal administration 20 mg L-DOPA (various formulations) delivered intranasally by the nhpPOD Device in monkeys pre-dosed with oral benserazide. The data were obtained in study 2037-006, as described in Example 1, with FIG. 3A plotting results without error bars, for clarity, and FIG. 3B including error bars. The orange line is bulk sifted L-DOPA with particles having diameters in the range of 20-40 μm (data from study 2037-004). The black line is bulk L-DOPA (data from study 2037-003). FIG. 3C shows mean Plasma Concentration-Time Curves following intranasal administration of 20 mg L-DOPA (curve with circles, data from Group 3 in study 2037-006) and in a combination formulation with a DDI (curve with rectangles, data from Group 5 in study 2037-006). Monkeys treated with the L-DOPA alone formulation were pre-dosed with oral benserazide at t=−24, −16, −8 and −0.75 hr; monkeys treated with the L-DOPA and DDI combination formulation were not pre-dosed with oral benserazide at t=−0.75 hr.

FIGS. 4A-4C show mean Plasma Concentration-Time Curves following intranasal administration of 20 mg L-DOPA (various formulations) delivered by the nhpPOD Device in monkeys pre-dosed with oral benserazide, from data obtained in study 2037-007 (Group 1-5 in Table 10), as described in Example 1, with FIG. 4A plotting results with error bars for all the PK time points (0-600 mins); FIG. 4B plotting results without error bars for clarity, for shorter PK time points (0-150 mins); and FIG. 4C plotting results without error bars, for even shorter PK time points (0-45 mins). FIGS. 4A-4C also include data from previous studies for comparison: (i) 52F (Group 4 in study 2037-006) (from Table 9); (ii) Bulk Sifted 20-40 μm Crystalline L-Dopa (Group 2 in study 2037-004) (from Table 7); (iii) 70A (Group 1 in study 2037-006) (L-Dopa:NaCl:HPMC:DSPC 68:2:16:14) (from Table 9); and (iv) 70B (Group 2 in study 2037-006) (L-Dopa:NaCl:HPMC:DSPC 68:2:23:7) (from Table 9).

FIGS. 5A-5E show Plasma Concentration-Time Curves for individual animals following 20 mg L-DOPA (various formulations) delivered by the nhpPOD Device in monkeys pre-dosed with oral benserazide, from data obtained in study 2037-007, as described in Example 1. FIG. 5A plots data for four individual animals in Group 1 (male 1001, male 1002, female 1501, female 1502); FIG. 5B plots data for four individual animals in Group 2 (male 2001, male 2002, female 2501, female 2502); FIG. 5C plots data for four individual animals in Group 3 (male 3001, male 3002, female 3501, female 3502); and FIG. 5D plots data for four individual animals in Group 4 (male 4001, male 4002, female 4501, female 4502). Animals in each group were administered L-DOPA as provided in Table 10.

FIG. 6 shows mean Plasma Concentration-Time Curves following 2.5 mg L-DOPA formulations delivered by the rPOD Device in rats with pretreatment with oral benserazide (HQ00001) or without pretreatment with oral benserazide (BG54-126). The data were obtained in study PBI-18-057, as described in Example 2. BG54-126 and HQ00001 formulations contain similar compositions except that BG54-126 has carbidopa integrated into the formulation.

Figure 10:
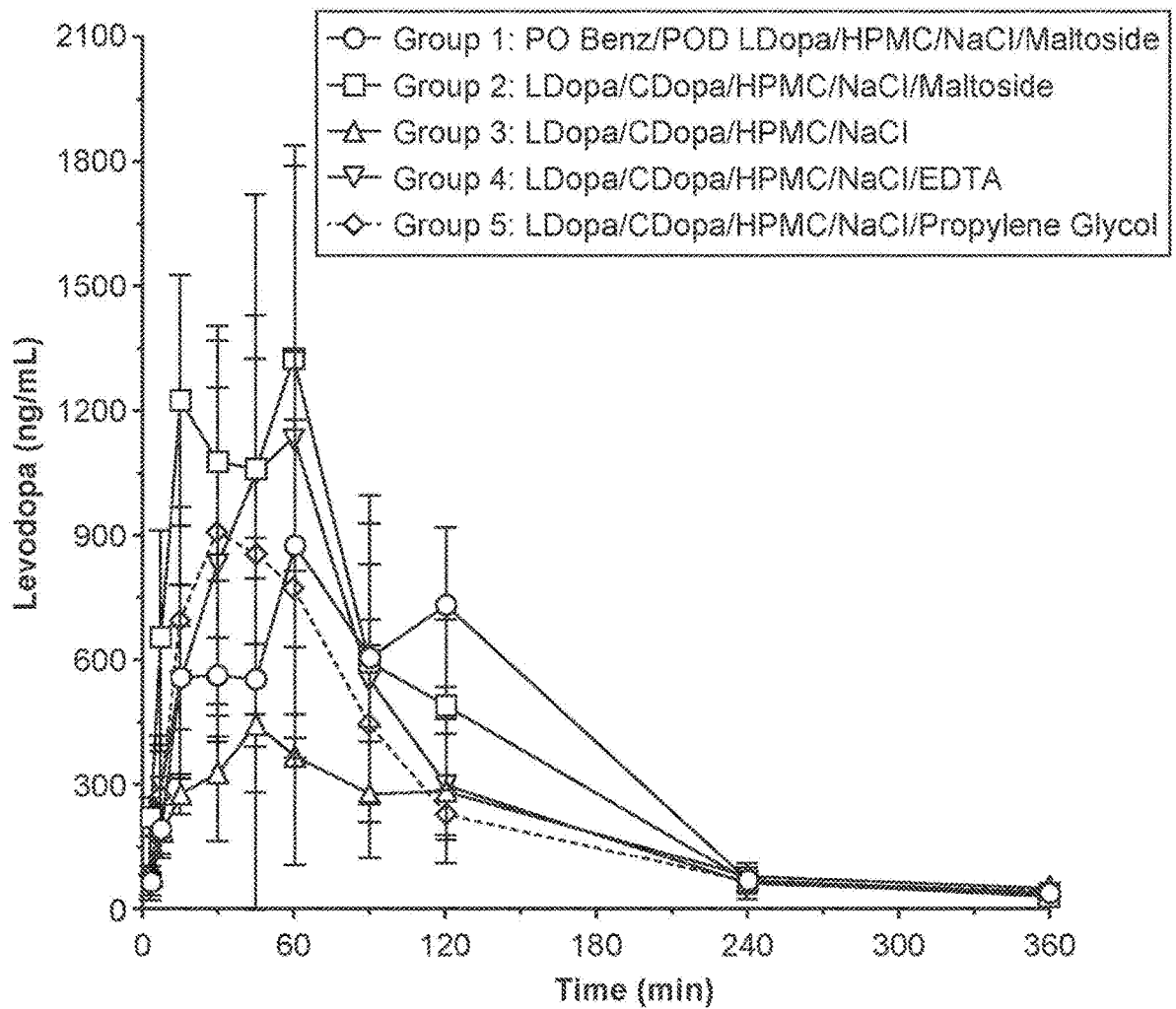

FIG. 10 shows mean Plasma Concentration-Time Curves following intranasal administration of 20 mg L-DOPA in various formulations delivered by the nhpPOD Device in monkeys. The data were obtained in study 2037-017, as described in Example 1. Group 1 was pretreated with oral benserazide prior to administration of L-DOPA. Groups 2-5 were not pretreated with a DDI, but administered with an L-DOPA formulation additionally containing carbidopa with or without a permeation enhancer (maltoside, EDTA, or propylene glycol).

Figure 11:
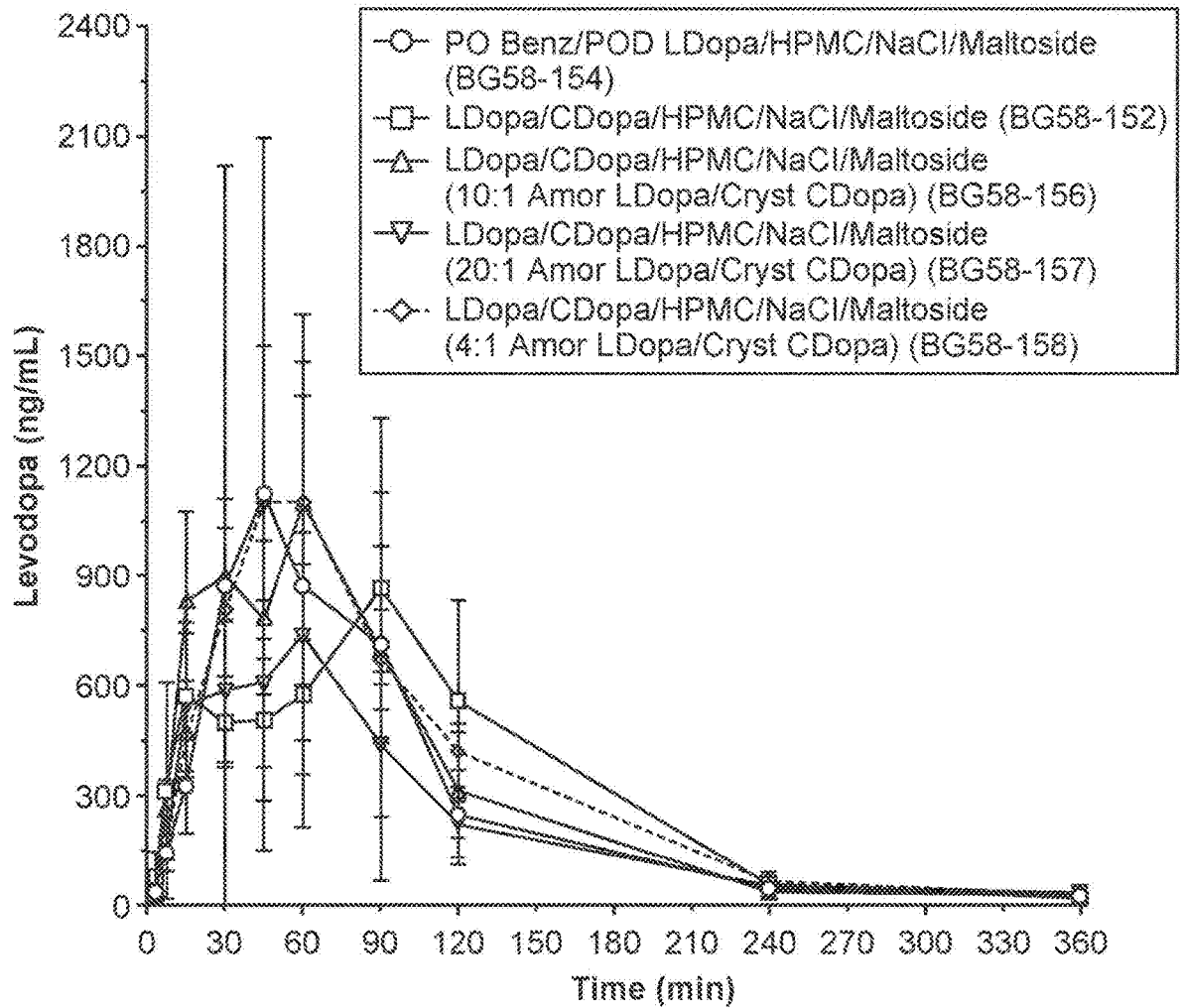

FIG. 11 shows mean Plasma Concentration-Time Curves following intranasal administration of 20 mg L-DOPA in various formulations delivered by the nhpPOD Device in monkeys. The data were obtained in study 2037-019, as described in Example 1. Group 1 was pretreated with oral benserazide prior to administration of L-DOPA. Groups 2-5 were not pretreated with a DDI, but administered with L-DOPA formulations additionally containing carbidopa at different ratios, 10:1, 20:1, or 4:1 ratios of L-DOPA:carbidopa.

Figure 12:
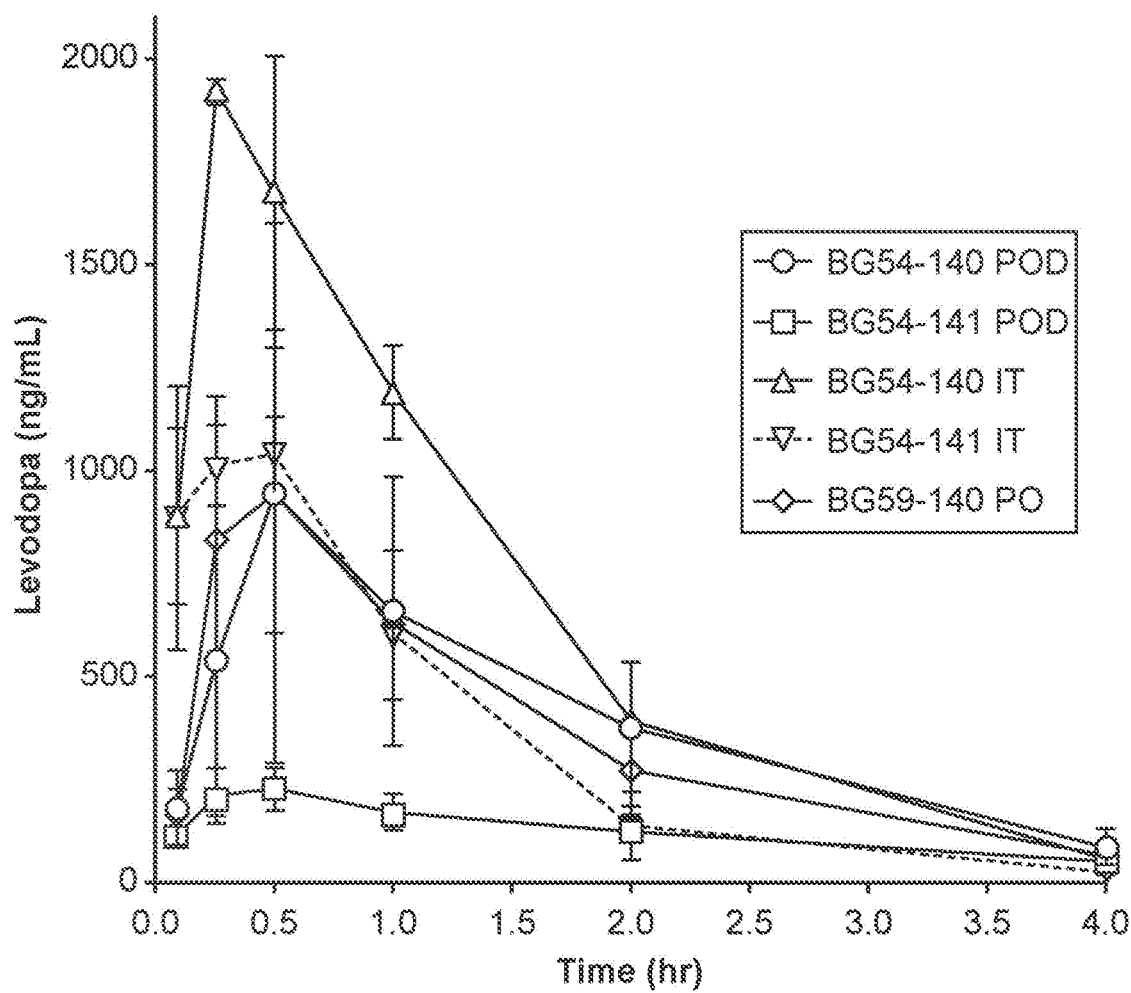

FIG. 12 show mean Plasma Concentration-Time Curves following administration of the BG54-140 or BG54-141 intranasally using an Impel rat Precision Olfactory Delivery Device ("rPOD") ("POD"), intratracheally (i.t.) using an Impel IT Device ("IT"), or oral gavage ("PO"). BG54-140 and BG54-141 formulations contain similar compositions except that BG54-140 has carbidopa integrated into the formulation at 10:1 ratio of L-DOPA:carbidopa. The data were obtained in study PBI-19-056, as described in Example 2.

Figure 13:
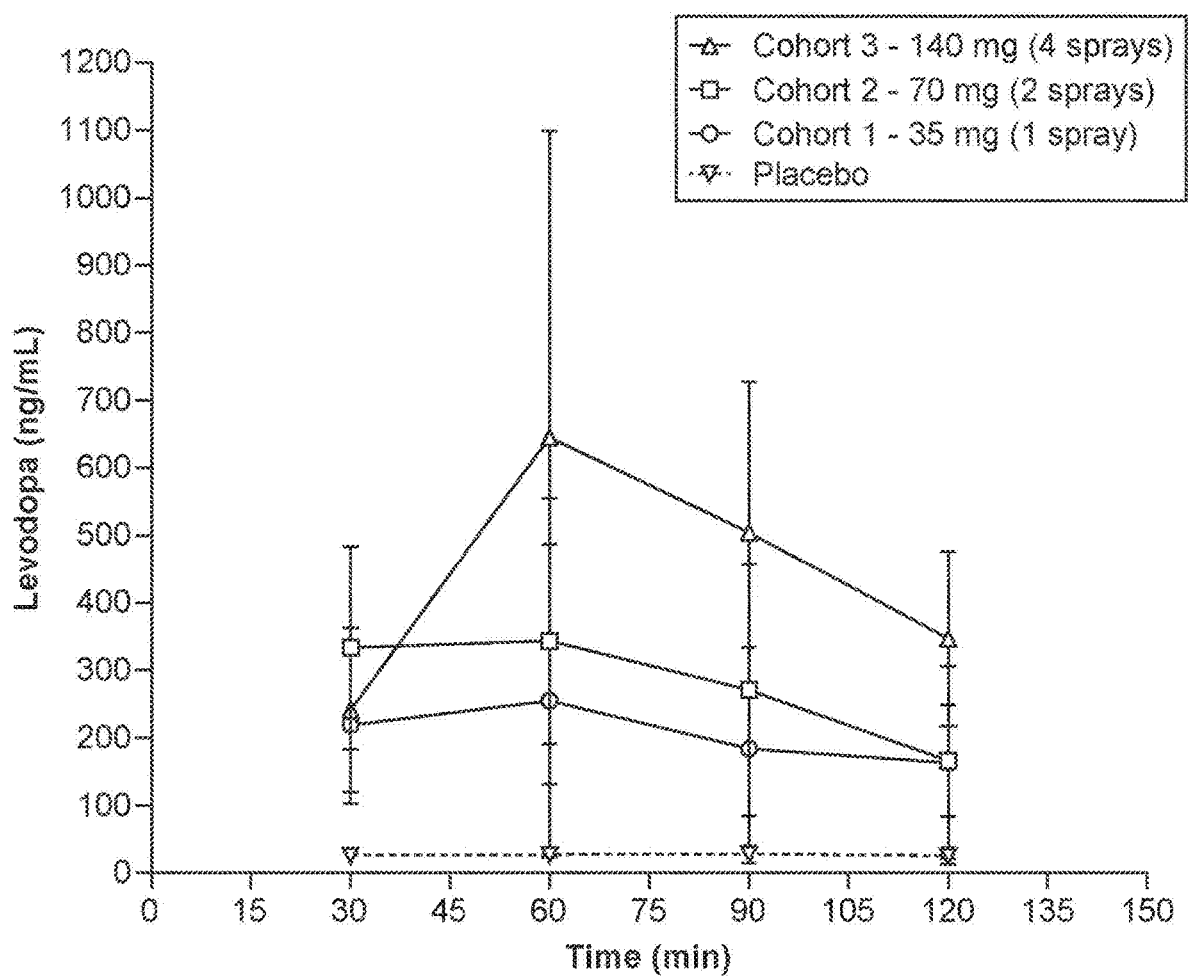

FIG. 13 shows mean Plasma Concentration-Time Curves following intranasal administration of 35 mg (Cohort 1), 70 mg (Cohort 2), or 140 mg L-DOPA (Cohort 3) using I231 POD device with pretreatment with oral benserazide 60 minutes prior to levodopa administration. The data were obtained in the Phase IIa human clinical study described in Example 3.

Figure 14:
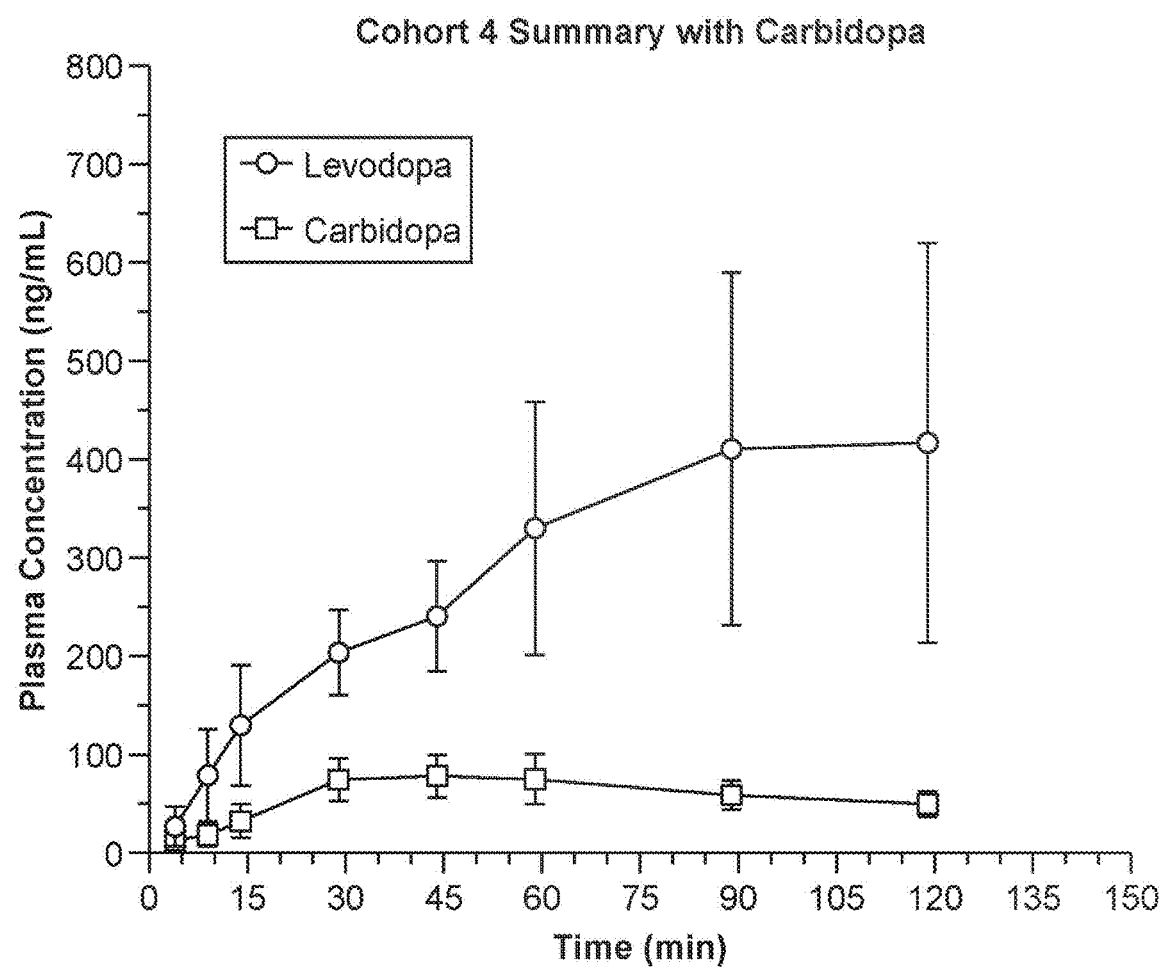

FIG. 14 shows mean Plasma Concentration-Time Curves for L-DOPA and carbidopa following intranasal administration of the formulation containing 10:1 ratio of L-DOPA:carbidopa using the I231 POD device without pretreatment with oral carbidopa (Cohort 4). The data were obtained in the Phase IIa, human clinical study described in Example 3.

5. DETAILED DESCRIPTION

5.1. Definitions

Unless defined otherwise, all technical and scientific terms used herein have the meaning commonly understood by a person skilled in the art to which this invention belongs.

An "OFF" episode is defined as a period during which a patient with Parkinson Disease (PD) or a Parkinson syndrome who is receiving an anti-Parkinson treatment has a UPDRS III motor score ≥30.

"Maltoside" refers to N-Dodecyl-β-D-maltopyranoside (n-dodecyl β-D-maltoside).

A pharmaceutical composition is "dry" if it has a residual moisture content of no more than 10%.

Intranasal administration of levodopa or administration of levodopa by oral inhalation is "adjunctive to" an oral treatment with a decarboxylase inhibitor when levodopa is administered by intranasal administration or oral inhalation, respectively, in sufficient temporal proximity to a prior oral administration of decarboxylase inhibitor that the plasma $C_{max}$ of the intranasally administered levodopa is increased.

5.1. Other Interpretational Conventions

Particle sizes are sizes as reported by a Mastersizer 3000 laser diffraction particle size analyzer device (Malvern Panalytical).

Ranges: throughout this disclosure, various aspects of the invention are presented in a range format. Ranges include the recited endpoints. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Unless specifically stated or otherwise apparent from context, as used herein the term "or" is understood to be inclusive.

Unless specifically stated or otherwise apparent from context, as used herein, the terms "a", "an", and "the" are understood to be singular or plural. That is, the articles "a" and "an" are used herein to refer to one or to more than one (i.e., to at least one) of the grammatical object of the article. By way of example, "an element" means one element or more than one element.

In this disclosure, "comprises," "comprising," "containing," "having," "includes," "including," and linguistic variants thereof have the meaning ascribed to them in U.S. Patent law, permitting the presence of additional components beyond those explicitly recited.

Unless specifically stated or otherwise apparent from context, as used herein the term "about" is understood as within a range of normal tolerance in the art, for example within 2 standard deviations of the mean.

5.2. Summary of Experimental Observations

We conducted single dose PK studies in cynomolgus monkeys and rats to examine the pharmacokinetics ("PK") following intranasal administration of various powder formulations of levodopa (L-DOPA), with and without predosing with oral DDI. The formulations examined included an unmodified crystalline powder (median particle size 50 µm), a sifted formulation containing crystalline L-DOPA particles with size range of 20-40 µm, spray dried formulations of L-DOPA with various excipient mixtures, and spray dried formulations of L-DOPA in combination with a DDI.

We found that intranasal administration of several spray-dried L-DOPA formulations led to rapid rise in blood levels of levodopa, above the level known to be correlated with improving OFF episodes in human patients, but only in animals pre-treated with an oral DDI. We also demonstrated that intranasal administration of comparable L-DOPA formulations further containing a DDI rapidly increased blood levels of levodopa, even without pre-treatment with oral DDI. The results demonstrate that DOPA decarboxylase inhibitors can be delivered to the respiratory tract in amounts effective to permit rapid and reproducible absorption of therapeutic amounts of levodopa administered in combination, for the first time obviating the need for adjunctive administration of oral DDI during respiratory tract delivery of levodopa by intranasal administration or oral inhalation.

We then tested intranasal delivery of levodopa to human patients in a Phase 11a, randomized, double blind, placebo controlled, single ascending dose, safety and pharmacokinetic/pharmacodynamic study. In Cohorts 1-3, patients were pretreated with oral benserazide, a DDI, and then administered levodopa intranasally. In cohort 4, patients were not pretreated with oral DDI. Instead, a dry formulation that included both levodopa and DDI was administered intranasally.

In cohorts 1-3 (oral benserazide pretreatment), L-DOPA concentration reached therapeutic blood levels to treat daytime OFF episode by the first blood draw of 30 mins. In many individuals in Cohorts 1-3, peak plasma concentrations were achieved at or before 30 mins. Less than dose-proportional PK was observed in Cohorts 1-3, which may be partially due to the total amount of powder delivered to the nasal surface area.

In Cohort 4 (BG54-140 without oral benserazide pretreatment), L-DOPA concentration reached therapeutic blood levels to treat daytime OFF episode at 45-90 minutes, and stayed high until 120 mins after administration, with lower variability of L-DOPA concentrations. $C_{max}$ of levodopa after intranasal administration of 7 mg carbidopa by the POD was similar to $C_{max}$ measured after oral administration of 50 mg carbidopa, and $T_{max}$ was approximately 4-fold faster than oral.

5.3. Dry Pharmaceutical Composition

Accordingly, in a first aspect, dry pharmaceutical compositions are provided. The compositions comprise levodopa, a dopa decarboxylase inhibitor (DDI), and at least one excipient, and are suitable for delivery to the respiratory tract.

In some embodiments, the dry pharmaceutical composition is a powder suitable for intranasal administration. In some embodiments, the dry pharmaceutical composition is a powder suitable for administration by oral inhalation (i.e., pulmonary administration).

In certain embodiments, the powder comprises a plurality of separate levodopa and DDI particles. In particular embodiments, levodopa and DDI are individually spray-dried, and particles containing levodopa and particles containing DDI are mixed to provide a dry pharmaceutical composition containing both levodopa and DDI. In certain embodiments, the powder comprises particles that include both levodopa and DDI. In particular embodiments, a liquid formulation comprising both levodopa and DDI is spray dried to produce particles that include both levodopa and DDI. In certain embodiments, the powder comprises separate particles of levodopa and DDI as well as particles that include both levodopa and DDI.

Particle size distributions are known to be important for efficient delivery of the particles to specific anatomic locations within the respiratory tract. Optimal particle size distributions for delivery to a desired anatomic location within the respiratory tract can be determined by testing absorption (one or more of plasma $C_{max}$, AUC, $T_{max}$) of various size ranges. Optimal size distributions for pulmonary administration were previously identified and described, for example, in Lipp et al. Science Translational Medicine, 8, 360ra136 (2016); Luinstra et al., European Journal of Pharmaceutics and Biopharmaceutics, 97 (2015) 22-29; and DeLong et al., Journal of Aerosol Medicine, 18 (2005) 452-59, incorporated herein by reference in their entireties. Optimal size distributions for nasal administration were described, for example, in Wang et al. Journal of Pharmaceutical Sciences 101:31-47 (2012); and Garmise et. al. AAPS PharmSciTech, 7 (1) Article 10 (2006), incorporated herein by reference in their entireties.

In some embodiments, the median diameter of the plurality of particles (D50) is 1 μm-500 μm, 1 μm-250 μm, 1 μm-100 μm, 1 μm-75 μm, 1 μm-50 μm, 1 μm-40 μm, 1 μm-5 μm, 1 μm-3 μm, 10 μm-40 μm, 10 μm-30 μm, 20 μm-40 μm, or 15 μm-35 μm. In some embodiments, the median diameter of the levodopa particle size distribution (D50) in the powder is 1 μm-500 μm, 1 μm-250 μm, 1 μm-100 μm, 1 μm-75 μm, 1 μm-50 μm, 1 μm-40 μm, 1 μm-5 μm, 1 μm-3 μm, 10 μm-40 μm, 10 μm-30 μm, 20 μm-40 μm, or 15 μm-35 μm. In some embodiments, the median diameter of the DDI particle size distribution (D50) in the powder is 1 μm-500 μm, 1 μm-250 μm, 1 μm-100 μm, 1 μm-75 μm, 1 μm-50 μm, 1 μm-40 μm, 1 μm-5 μm, 1 μm-3 μm, 10 μm-40 μm, 10 μm-30 μm, 20 μm-40 μm, or 15 μm-35 μm.

In some embodiments, the median diameter of the plurality of particles (D50) is 10 μm-500 μm, 10 μm-400 μm, 10 μm-300 μm, 10 μm-200 μm, 20 μm-200 μm, 20 μm-150 μm, 30 μm-150 μm, 40 μm-150 μm, 30 μm-100 μm, 40 μm-100 μm, 40 μm-80 μm, 40 μm-70 μm, 40 μm-60 μm, or 40 μm-50 μm. In some embodiments, the median diameter of the levodopa particle size distribution (D50) in the powder is 10 μm-500 μm, 10 μm-400 μm, 10 μm-300 μm, 10 μm-200 μm, 20 μm-200 μm, 20 μm-150 μm, 30 μm-150 μm, 40 μm-150 μm, 30 μm-100 μm, 40 μm-100 μm, 40 μm-80 μm, 40 μm-70 μm, 40 μm-60 μm, or 40 μm-50 μm. In some embodiments, the median diameter of the DDI particle size distribution (D50) in the powder is 10 μm-500 μm, 10 μm-400 μm, 10 μm-300 μm, 10 μm-200 μm, 20 μm-200 μm, 20 μm-150 μm, 30 μm-150 μm, 40 μm-150 μm, 30 μm-100 μm, 40 μm-100 μm, 40 μm-80 μm, 40 μm-70 μm, 40 μm-60 μm, or 40 μm-50 μm.

In some embodiments, the median diameter of the plurality of particles (D50) is 0.5 μm-20 μm, 1 μm-20 μm, 1 μm-15 μm, 1 μm-10 μm, 1 μm-8 μm, 1 μm-6 μm, 1 μm-5 μm, 1 μm-4 μm, 2 μm-5 μm, 3 μm-5 μm, or 4 μm-5 μm. In some embodiments, the median diameter of the levodopa particle size distribution (D50) in the powder is 0.5 μm-20 μm, 1 μm-20 μm, 1 μm-15 μm, 1 μm-10 μm, 1 μm-8 μm, 1 μm-6 μm, 1 μm-5 μm, 1 μm-4 μm, 2 μm-5 μm, 3 μm-5 μm, or 4 μm-5 μm. In some embodiments, the median diameter of the DDI particle size distribution (D50) in the powder is 0.5 μm-20 μm, 1 μm-20 μm, 1 μm-15 μm, 1 μm-10 μm, 1 μm-8 μm, 1 μm-6 μm, 1 μm-5 μm, 1 μm-4 μm, 2 μm-5 μm, 3 μm-5 μm, or 4 μm-5 μm.

In various embodiments, the composition comprises levodopa in crystalline form. In some embodiments, the composition comprises levodopa in amorphous form. In certain embodiments, the amorphous levodopa is obtained by spray-drying. In some embodiments, the composition comprises levodopa in a crystalline form and an amorphous form. In some embodiments, the composition comprises levodopa in a partially crystalline and partially amorphous form.

In various embodiments, the dry pharmaceutical composition comprises no more than 95 wt % levodopa, no more than 90 wt % levodopa, no more than 85 wt % levodopa, or no more than 80 wt % levodopa. In certain embodiments, the composition comprises 50-80 wt % levodopa, 50-70 wt % levodopa, or 65-70 wt % levodopa.

In typical embodiments, the DDI in the dry pharmaceutical composition is carbidopa or benserazide. In some embodiments, the DDI is carbidopa. In some embodiments, the DDI is benserazide.

In typical embodiments, the dry pharmaceutical composition comprises no more than 30 wt % DDI. In some embodiments, the composition comprises 5-30 wt % DDI, or 8-25 wt % DDI.

In some embodiments, the weight ratio between levodopa and the DDI is between 1:1 and 12:1. In some embodiments, the weight ratio between levodopa and the DDI is between 1:1 and 2:1, 2:1 or 1:1. In some embodiments, the weight ratio between levodopa and the DDI is between 3:1 and 12:1. In some embodiments, the weight ratio between levodopa and the DDI is between 4:1 and 11:1, 10:1 or 4:1.

In typical embodiments, the dry pharmaceutical composition further comprises a nonionic surfactant. In some embodiments, the nonionic surfactant is an alkyl maltoside, and in currently preferred embodiments, the alkyl maltoside is n-dodecyl β-D-maltoside.

In some embodiments, the nonionic surfactant is present at 0.1-10 wt %, more preferably, 1-5 wt %. In particular embodiments, the nonionic surfactant is present at 1 wt %.

In various embodiments, the dry pharmaceutical composition further comprises hydroxypropyl methyl cellulose (HPMC).

In some embodiments, the dry pharmaceutical composition further comprises 1,2-Distearoyl-sn-glycero-3-phosphocholine (DSPC).

In various embodiments, the dry pharmaceutical composition further comprises a salt of a monovalent inorganic cation. In typical embodiments, the salt is NaCl. In certain embodiments, the composition comprises 1-5 wt % NaCl or, more preferably, 2-4 wt % NaCl.

In some embodiments, the dry pharmaceutical composition comprises 68 wt % levodopa, 2 wt % NaCl, 7 wt % benserazide, 16 wt % HPMC, and 7 wt % DSPC. In some embodiments, the dry pharmaceutical composition comprises 68 wt % levodopa, 2 wt % NaCl, 6.8 wt % carbidopa, 22.2 wt % HPMC, and 1 wt % n-dodecyl β-D-maltoside. In particularly preferred embodiments, the composition is a spray dried composition that comprises levodopa in amorphous form.

In some embodiments, L-DOPA is spray dried in the presence of DDI, HPMC and/or maltoside. In other embodiments, DDI, HPMC and/or maltoside is added after spray drying of L-DOPA.

In some embodiments, the dry pharmaceutical composition comprises less than 10%, less than 9%, less than 8%, less than 7%, less than 6%, less than 5%, less than 4%, less than 3%, less than 2%, or less than 1% of residual moisture.

5.4. Unit Dosage Form

In another aspect, unit dosage forms are provided. The unit dosage form contains a dry pharmaceutical composition as described in Section 4.3 above.

In typical embodiments, the unit dosage form contains 25-150 mg of levodopa. In certain embodiments, the unit dosage form contains 35-140 mg of levodopa. In particular embodiments, contains 35 mg of levodopa, 50 mg of levodopa, 70 mg of levodopa, or 100 mg of levodopa.

In typical embodiments, the unit dosage form is a capsule that encapsulates the dry pharmaceutical composition. In currently preferred embodiments, the capsule is a hard capsule. In some embodiments, the hard capsule is an HPMC hard capsule.

Figure 9A:
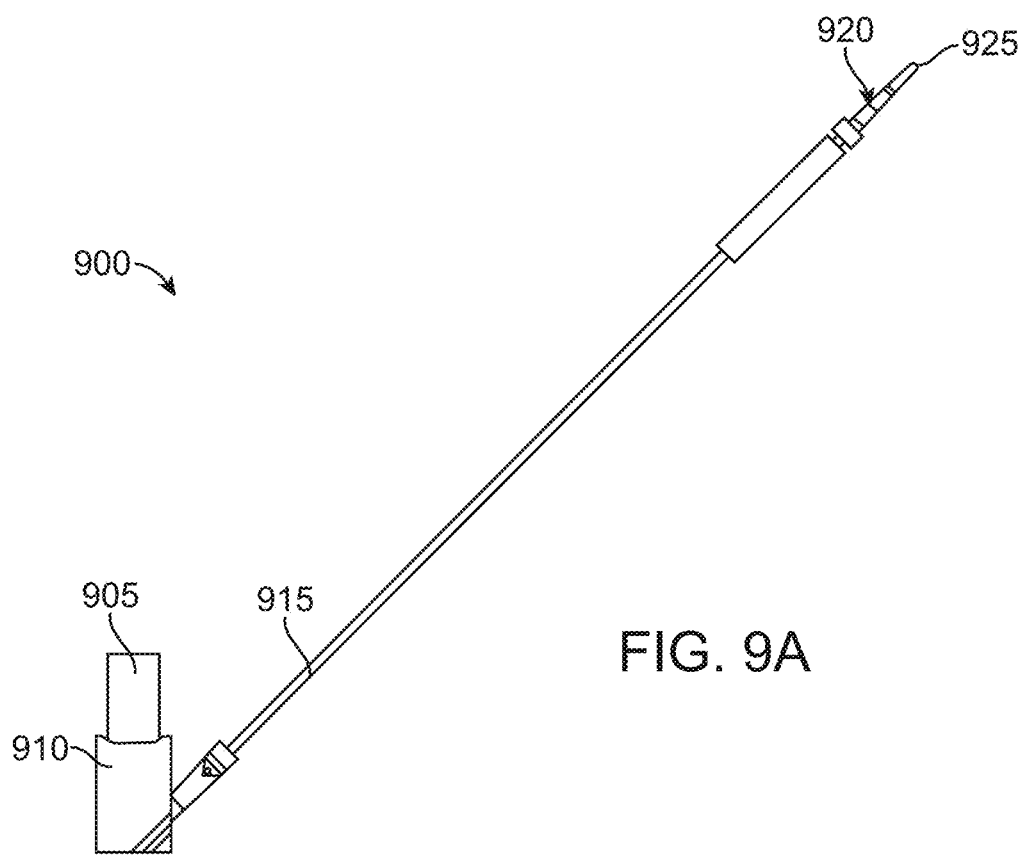
FIG. 9A illustrates the non-human primate precision olfactory delivery device used in studies 2037-003, 2037-004, 2037-006, 2037-007 described in Example 1.
Figure 9B:
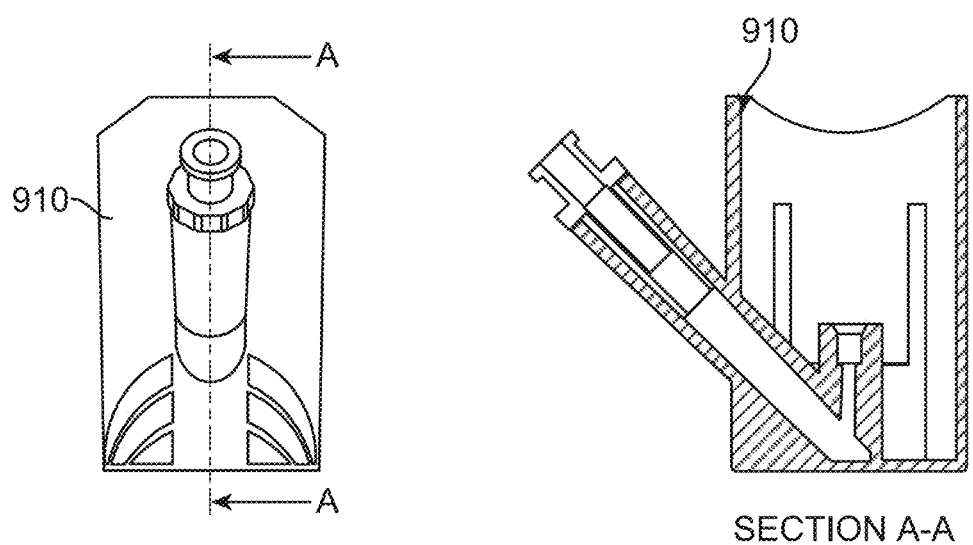
FIG. 9B illustrates a side view and a cross-sectional view of an actuator body of the intranasal device of FIG. 9A.

In some embodiments, the dry pharmaceutical composition is loaded directly into a tip of an intranasal device (i.e, without a capsule). In one embodiment, the dry pharmaceutical composition is loaded into a tip between a nozzle and a diffuser in the tip of an intranasal device, such as is illustrated in FIG. 9E.

In some embodiments, the unit dose form is adapted to cooperate with an administration device. The administration device can be an intranasal administration device or an oral inhaler. The administration device can be a handheld, manually actuated, metered dose administration device. The administration device can be a manually actuated, propellant drive, metered dose administration device. In some embodiments, the administration device is a breath actuated inhaler.

In some embodiments, one unit dosage form is individually encapsulated in a capsule. In some embodiments, more than one unit dosages are encapsulated in a capsule.

5.5. Methods of Treating Parkinson's Disease

In another aspect, methods are provided for treating a patient with Parkinson's disease or a Parkinson syndrome. The methods comprise delivering an effective amount of a dry pharmaceutical composition comprising levodopa (L-DOPA) and a dopa decarboxylase inhibitor (DDI) to the patient's respiratory tract. In some embodiments, the dry pharmaceutical composition is administered by intranasal administration. In some embodiments, the dry pharmaceutical composition is administered by oral inhalation.

5.5.1. Patients

Patients who can be treated with the methods provided herein have Parkinson's disease or a Parkinson syndrome, which includes, but not limited to, post-encephalitic parkinsonism, symptomatic parkinsonism following carbon monoxide intoxication, or symptomatic parkinsonism following manganese intoxication.

In some embodiments, the patient is not being treated with an oral DDI. In certain of these embodiments, the patient is not being treated with oral DDI or oral levodopa. In certain embodiments, the patients are not being treated with any dopaminergic treatment, including levodopa or dopamine agonist.

In some embodiments, the patient is also being treated with an oral DDI. In certain of these embodiments, the patient is also being treated with an oral DDI and oral levodopa. In some embodiments, the dry pharmaceutical composition is administered when the patient is experiencing an OFF episode. For example, the dry pharmaceutical composition can be used to treat OFF episodes that occur despite oral administration of an anti-Parkinson treatment.

In some embodiments, the patient discontinued a different anti-Parkinson treatment more than 12 hours, more than 24 hours, more than 48 hours, or more than a week before being treated with the dry pharmaceutical composition.

In some embodiments, the dry pharmaceutical composition is used as a primary therapy of Parkinson's disease or a Parkinson syndrome. In some cases, the dry pharmaceutical composition is used as an adjunct therapy of Parkinson's disease or a Parkinson syndrome.

5.5.2. Effective Dose

In some embodiments, the effective dose is a dose of levodopa effective to reverse a symptom associated with Parkinson's disease or a Parkinson syndrome.

In some embodiments, the effective dose is a dose of levodopa effective to reverse an OFF episode within 60 minutes. In some embodiments, the effective dose is a dose sufficient to provide, following administration, (a) a mean peak plasma levodopa concentration (Cmax) of at least 200-400 ng/mL, with (b) a mean time to Cmax (Tmax) of levodopa of less than 60 minutes.

In some embodiments, the effective dose of levodopa is 25-150 mg or 35-140 mg. In certain embodiments, the effective dose of levodopa is 35 mg, 50 mg, 70 mg, 100 mg, 105 mg, or 140 mg.

In some embodiments, the effective dose is administered as a single undivided dose. In some embodiments, the effective dose is administered as a plurality of equally divided sub-doses.

5.5.3. Device

In the methods described herein, the pharmaceutical composition is delivered to the respiratory tract using a delivery device. The delivery device can be an intranasal administration device or an oral inhalation administration device.

In currently preferred embodiments, the device is a handheld, manually actuated, metered-dose intranasal administration device. In certain embodiments, the device is manually actuated, propellant-driven metered-dose intranasal administration device.

In some embodiments, the device is a device for administration by oral inhalation. In particular embodiments, the device is a breath-actuated inhaler.

5.5.3.1. Nasal Drug Delivery Device

In various embodiments, the intranasal administration device is a nasal drug delivery device as described in U.S. Pat. No. 9,550,036, the disclosure of which is incorporated herein by reference in its entirety.

In various embodiments, the intranasal administration device is a non-human primate precision olfactory delivery ("nhpPOD") device described in FIGS. 9A-E, also described in U.S. Pat. No. 9,550,036 incorporated by reference in its entirety herein. In one embodiment, the intranasal device is one of the embodiments of FIGS. 1, 2, and 9 of U.S. Pat. No. 9,550,036. In these embodiments, the drug compound is loaded directly into the compound chamber.

Figure 8:
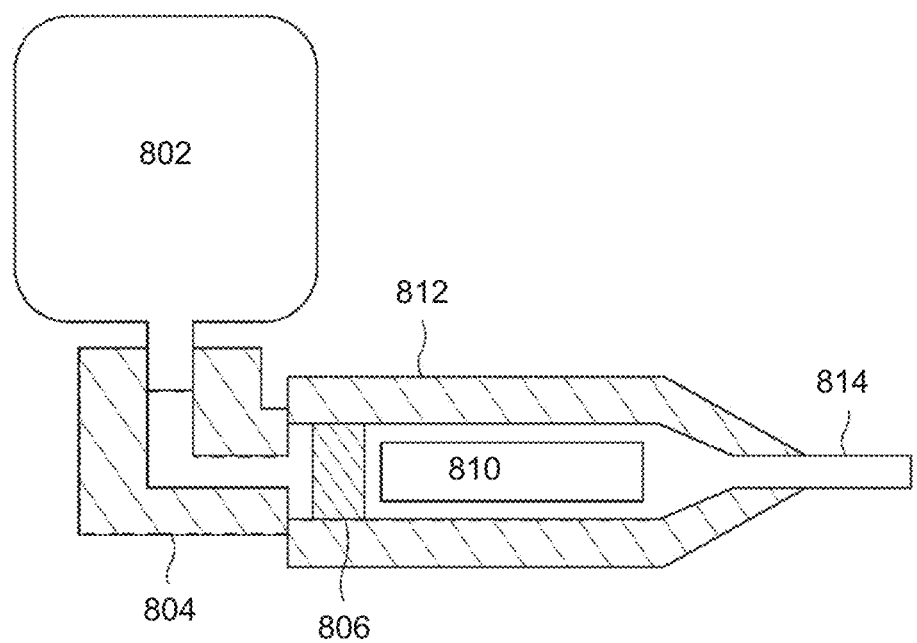
FIG. 8 illustrates an exemplary non-human primate precision olfactory delivery device.

The example nhpPOD device of FIG. 8 is described in the following paragraph. A meter dose inhaler (MDI) can 1700 dispensing 25 µl hydrofluoroalkane 227 is attached to the plastic actuator 1702. The actuator is in gas communication with a polytetrafluoroethylene frit 1704 which had a 50 µm pore size. The frit 1704 is in communication with the dose holding cylinder 1706 which is placed inside the body 1708 of the POD in order to create an aerosolized flow. On actuation the HFA propellant 1700 is converted to a gas by passing through the frit material 1704 and then it mixes with the dose 1706 and the dose and propellant mixture exits from the 23 gauge stainless steel tubing nozzle 1710 which is covered with a fluorinated ethylene-propylene liner that was placed over the outside of the metal tip in order to protect the nasal epithelia from being damaged by the nozzle 1710 during use. In one embodiment, the dose 1706 is loaded directly into the body 1708 without a holding cylinder.

5.5.3.2. Medical Unit Dose Container

In various embodiments, the intranasal administration device is a medical unit dose container as described in US 2016/0101245 A1, the disclosure of which is incorporated herein by reference in its entirety.

5.5.3.3. Intranasal Device with Inlet Interface

In various embodiments, the intranasal administration device is a medical unit dose container as described in U.S. provisional application No. 62/589,326, filed Nov. 21, 2017, the disclosure of which is incorporated herein by reference in its entirety, and repeated below for completeness.

Figure 7A:
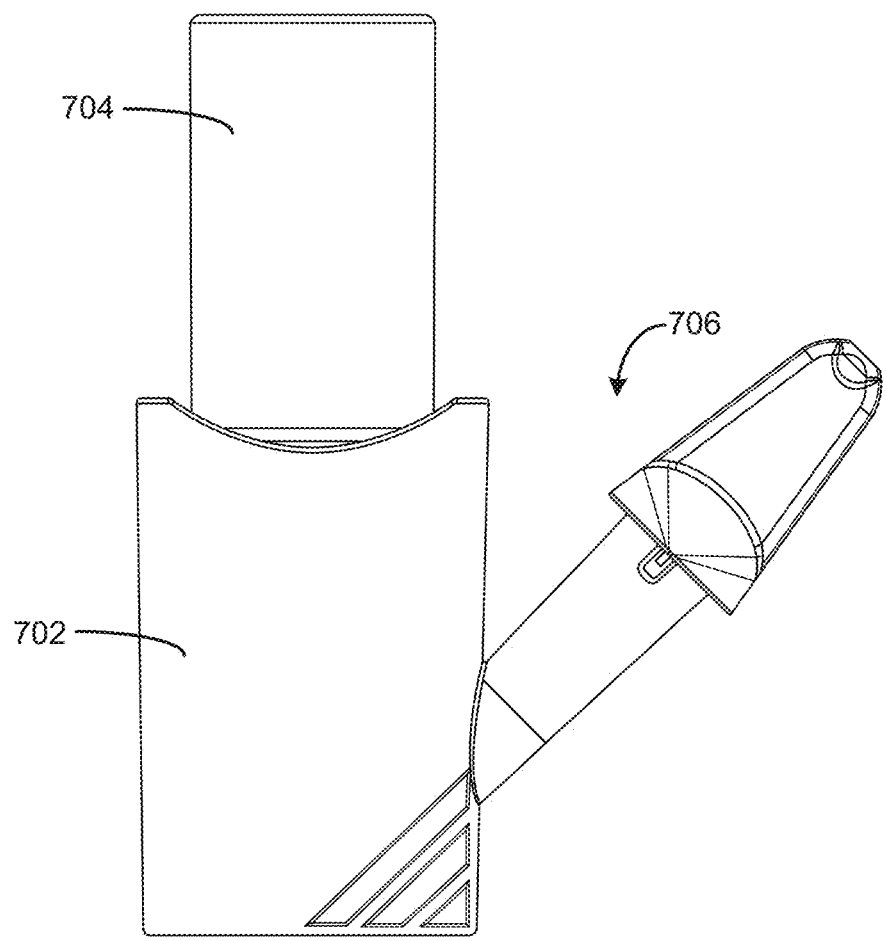
FIG. 7A is one embodiment of a device for intranasal administration of levodopa powder formulations into the nasal cavity of a patient.
Figure 7B:
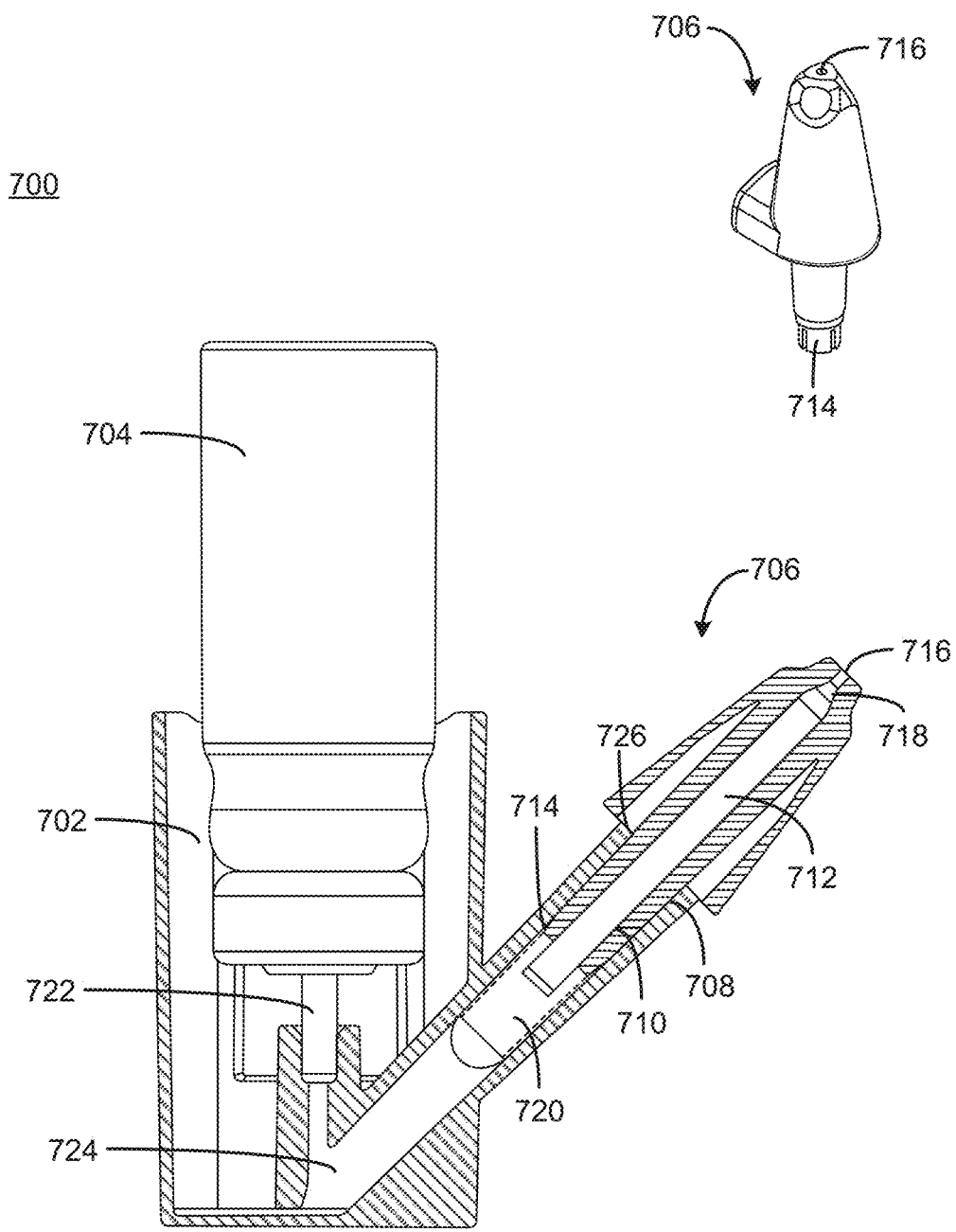
FIG. 7B is a partial cross section of one embodiment of the device.

As shown in FIGS. 7A and 7B, the intranasal device 700 with an inlet interface 714 is designed to deliver a consistent mass of compound (for example but not limited to an intranasal formulation) into the nasal cavity. The device 700 targets a specific region of the nasal cavity utilizing a narrow, targeted delivery plume. The device 700 provides compound to the upper one third of the nasal cavity, in one example, the olfactory region. The device 700 is also designed to simplify clinician loading and use.

As shown in FIG. 7B, a device 700 for delivering a compound intranasally is disclosed and described. The device 700 includes an actuator body 702, a propellant canister 704, and a tip 706. The tip 706 includes an outer wall 708 and an inner wall 710, an exit channel 712, an inlet interface 714 (for example but not limited to a collar, ring, band, port or strap) in fluid communication with the propellant canister 704, a compound container 720, the inlet interface 714 associated with the compound container 720, an exit opening 716 to the compound container 720, an exit channel 712 congruent with the exit opening 716 of the compound container 720, and a nozzle 718 congruent with the exit channel 712, the compound and propellant exiting the device 700 through the nozzle 718. The compound contained in the compound container 720 may be a liquid or a powder.

Figure 7C:
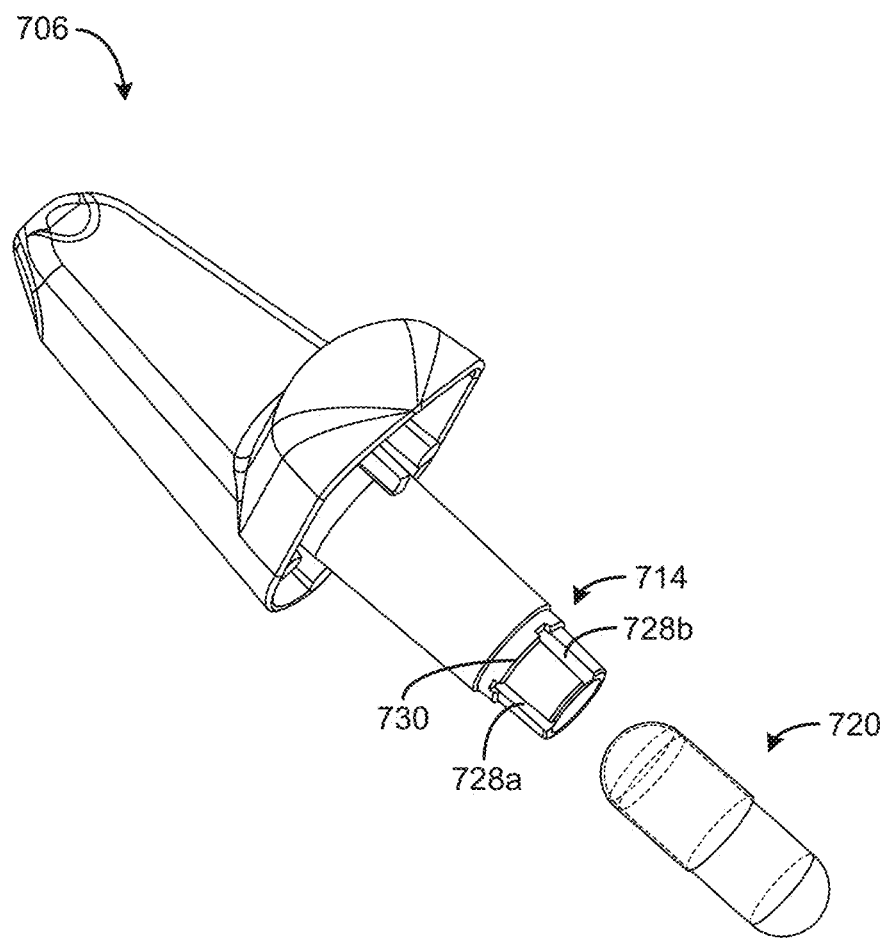
FIG. 7C is a partial exploded view.

As shown in FIG. 7B, in a first embodiment of the intranasal device 700, the device 700 includes a propellant canister 704. The propellant canister 704 is in fluid communication with an inlet interface 714 associated with the compound container 720 so that propellant from the propellant canister 704 can be introduced into the compound container 720. In this embodiment, as shown in FIG. 7C, the compound container 720 is a capsule. The capsule may be comprised of two portions fitted together. When separated, a portion of a capsule as shown in FIGS. 7E, 7F, and 7G, for example but not limited to a half capsule, may be associated with the device 700. In use, the capsule may contain a compound within the capsule. In one example, the compound is a powder. As shown in FIG. 7E, the opening of the capsule, for example the mouth of the half capsule, comprises the exit opening 732 to the compound container 720. As shown in FIG. 7G, in one example, the exit channel 712 is formed by a bore or lumen through the tip 706 of the device 700. In some cases, the tip 706 of the device 700 can have a different form, for example, as provided in FIG. 9E. As shown in FIG. 7H, the exit channel 712 has an inner wall 710 and an outer wall 708. The exit opening 732 fits snuggly with the outer wall 708 of the exit channel 712 in fluid communication with the nozzle 718 of the device 700.

Figure 7D:
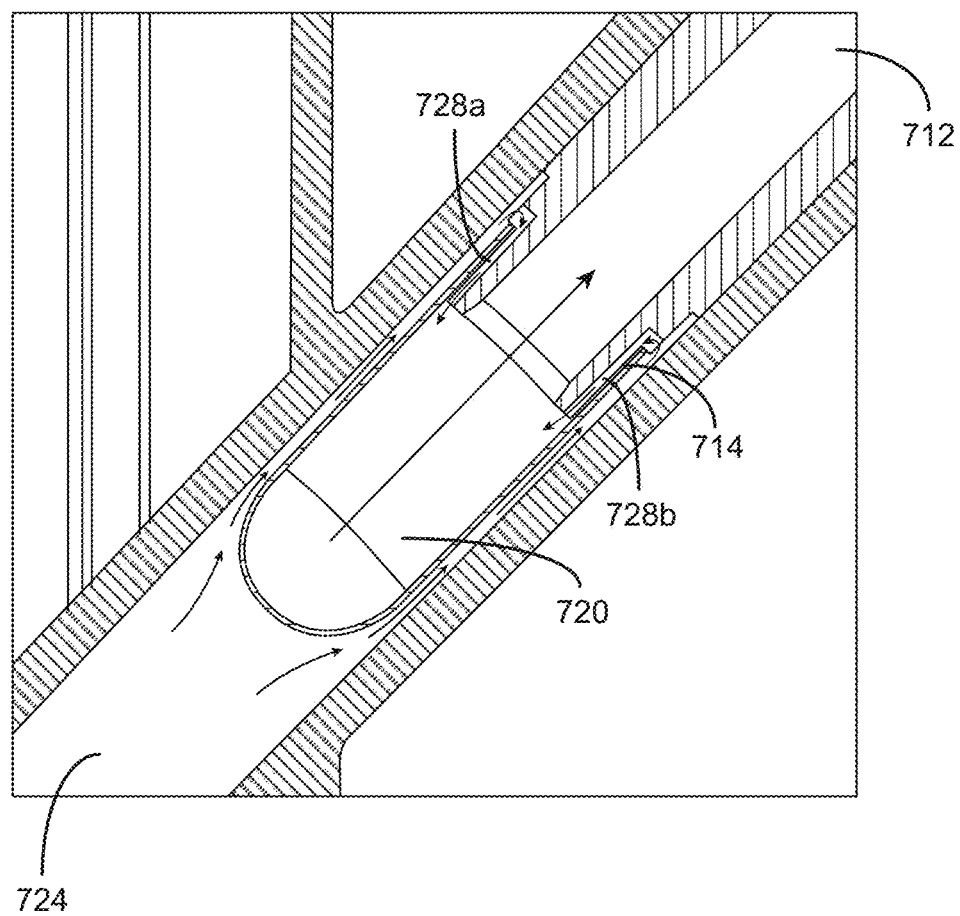
FIG. 7D is a cross section of one embodiment of the device.
Figure 7E:
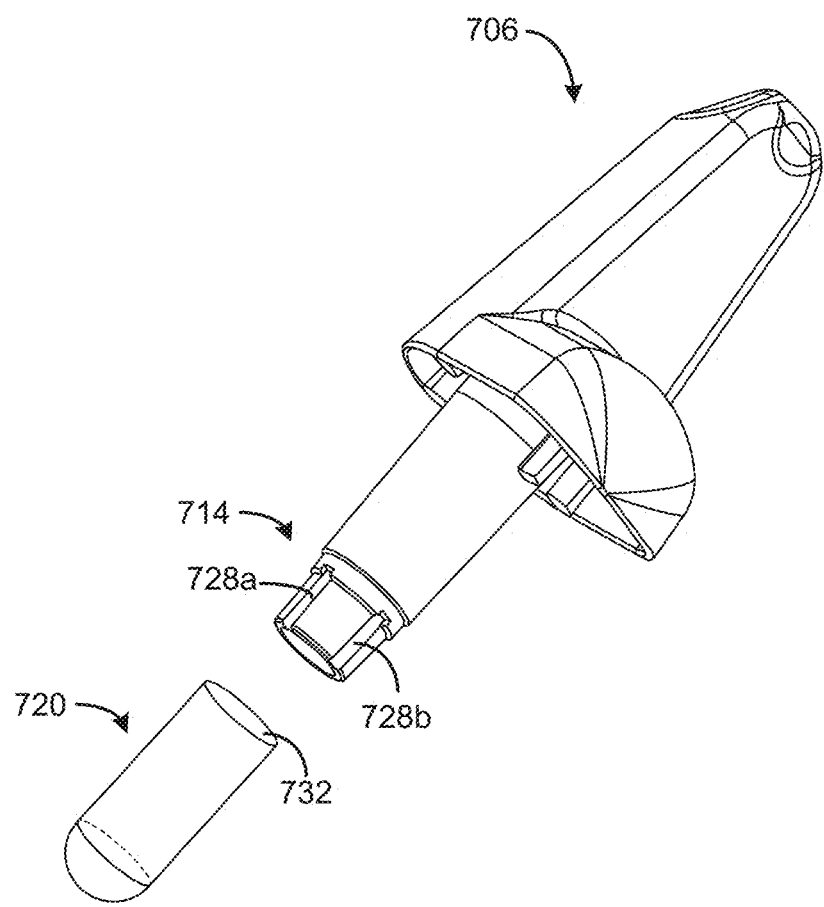
FIG. 7E is an exploded view.
Figures 7F, 7G:
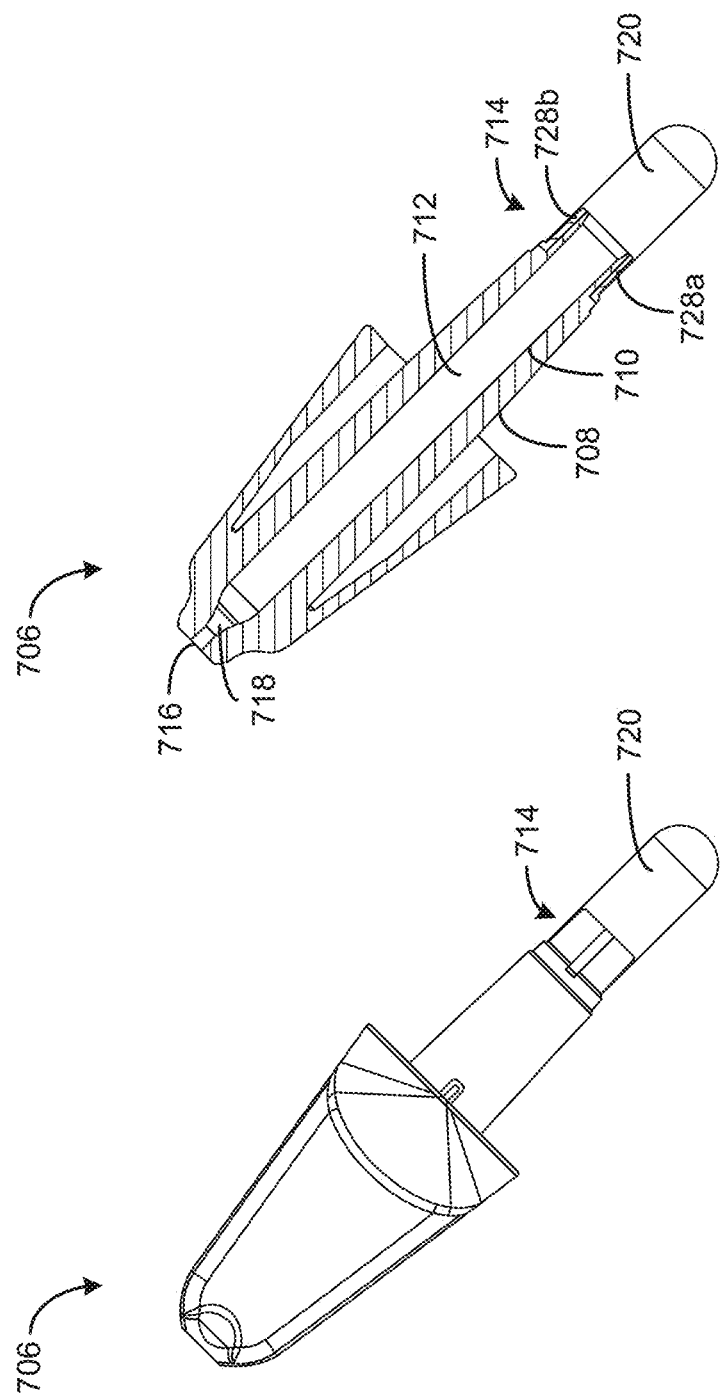
FIG. 7F is a portion of one embodiment of the device.
FIG. 7G is a cross section of the portion of the embodiment of FIG. 7F.
Figure 7H:
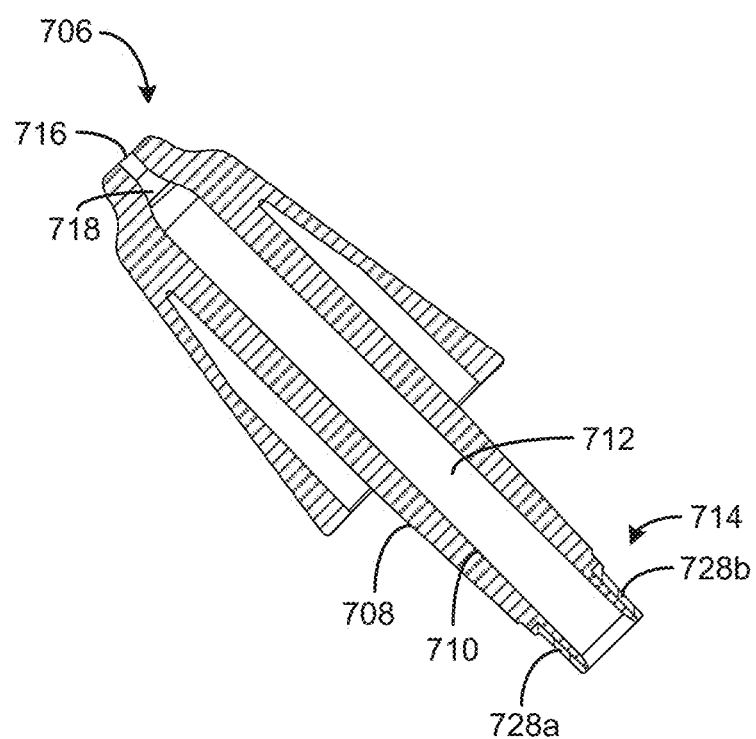
FIG. 7H is a cross section of one embodiment of the device.
Figure 7I:
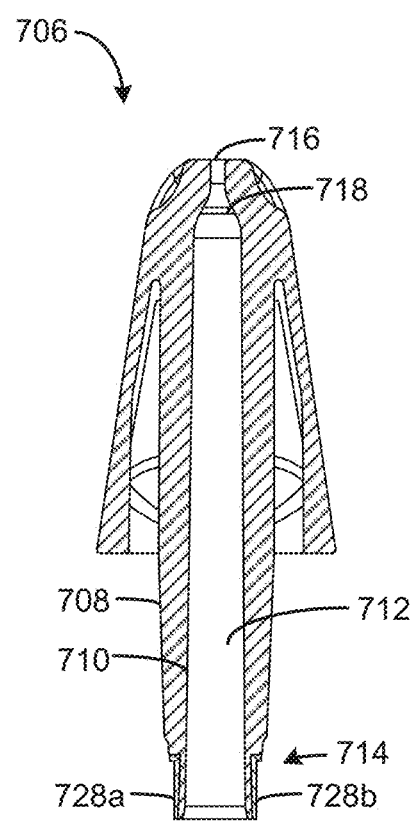
FIG. 7I is a cross section of the tip.
Figure 7J:
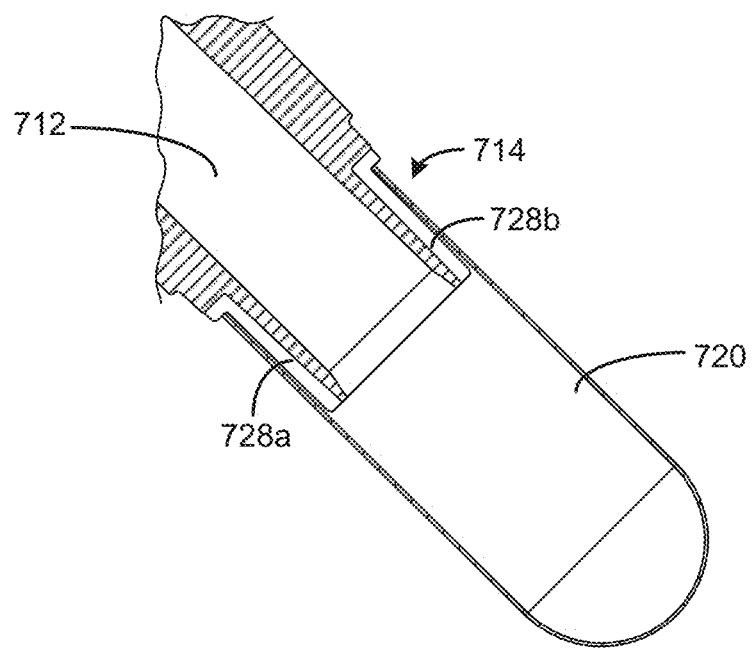
FIG. 7J is cross section of one portion of one embodiment of the device.
Figure 7K:
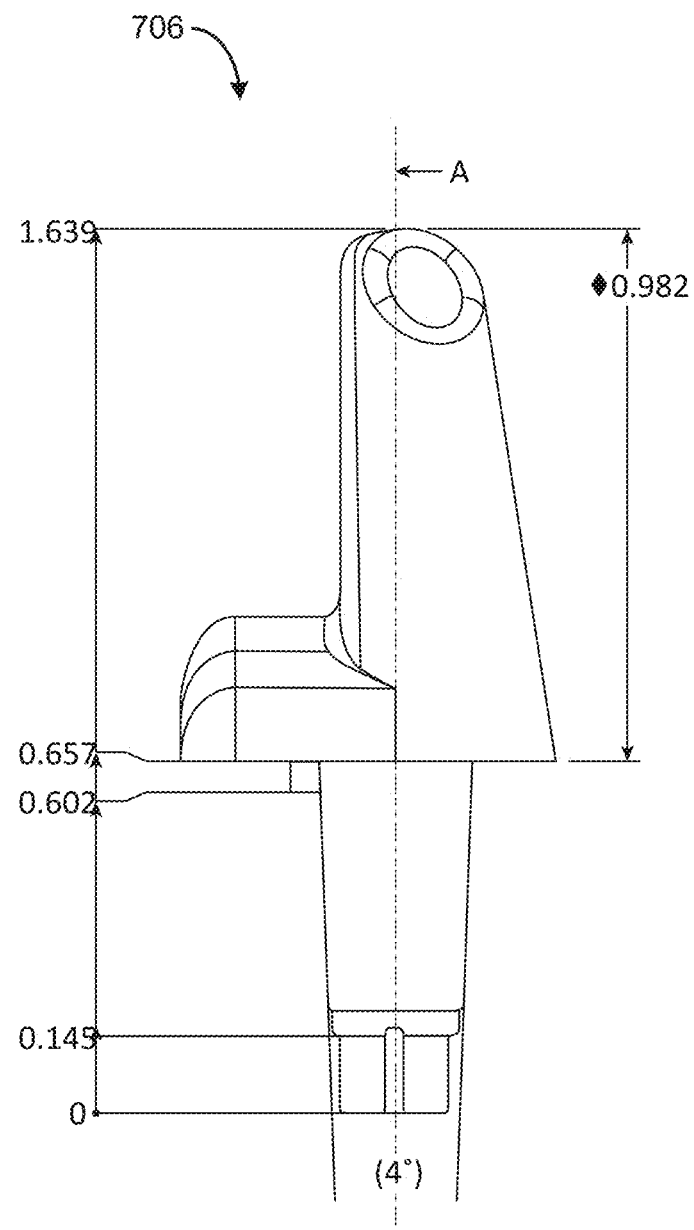
FIGS. 7K-7M are cross sections of the tip of the device and the grooves of one embodiment of the device.
Figure 7L:
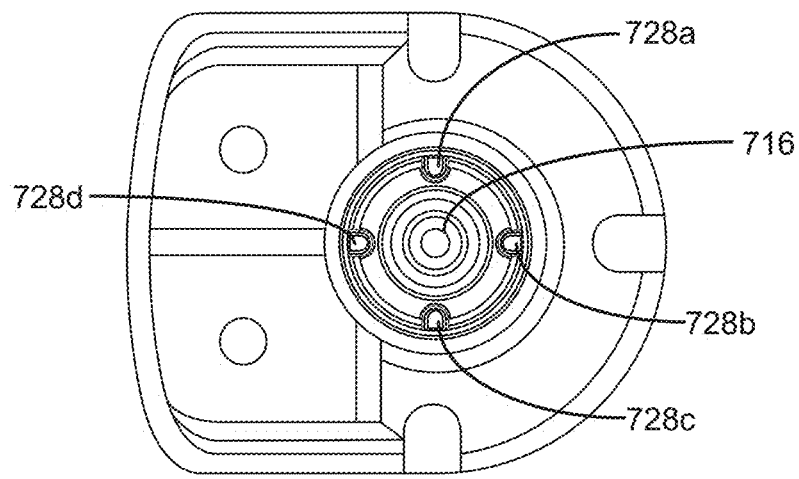
Figure 7M:
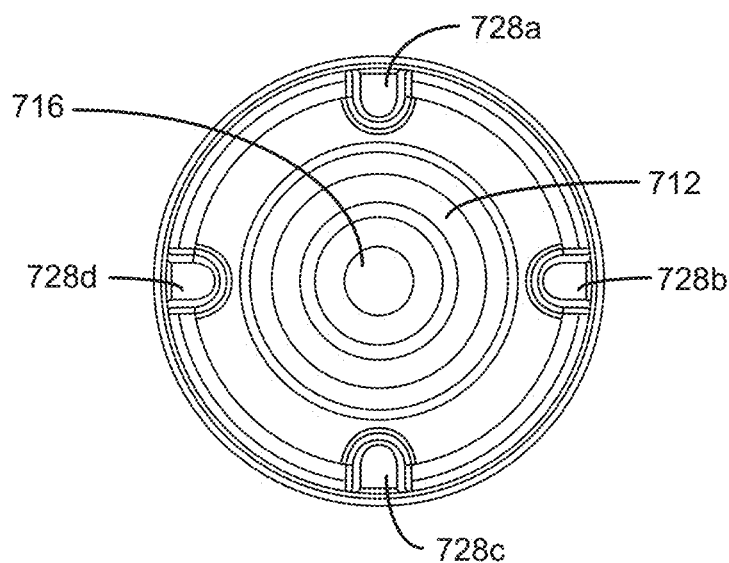
Figure 7N:
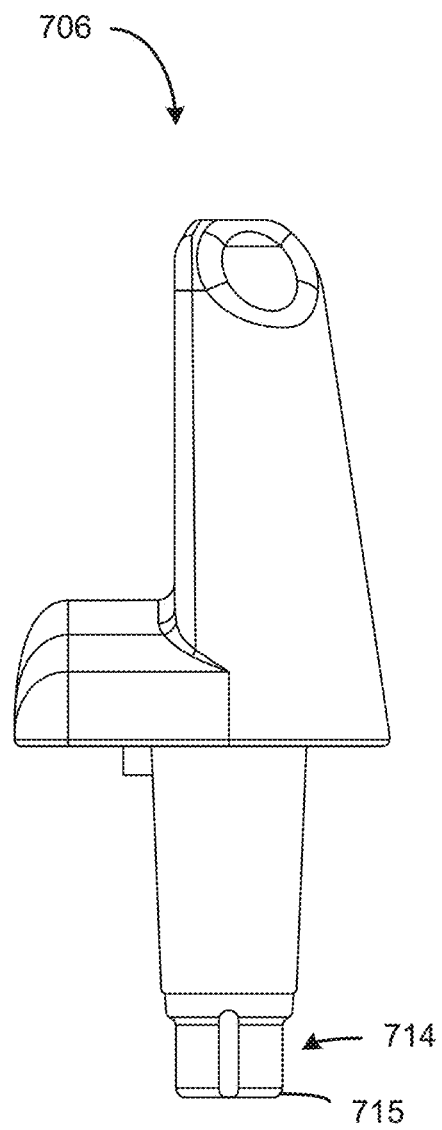
FIG. 7N is the tip of one embodiment of the device.
Figure 7O:
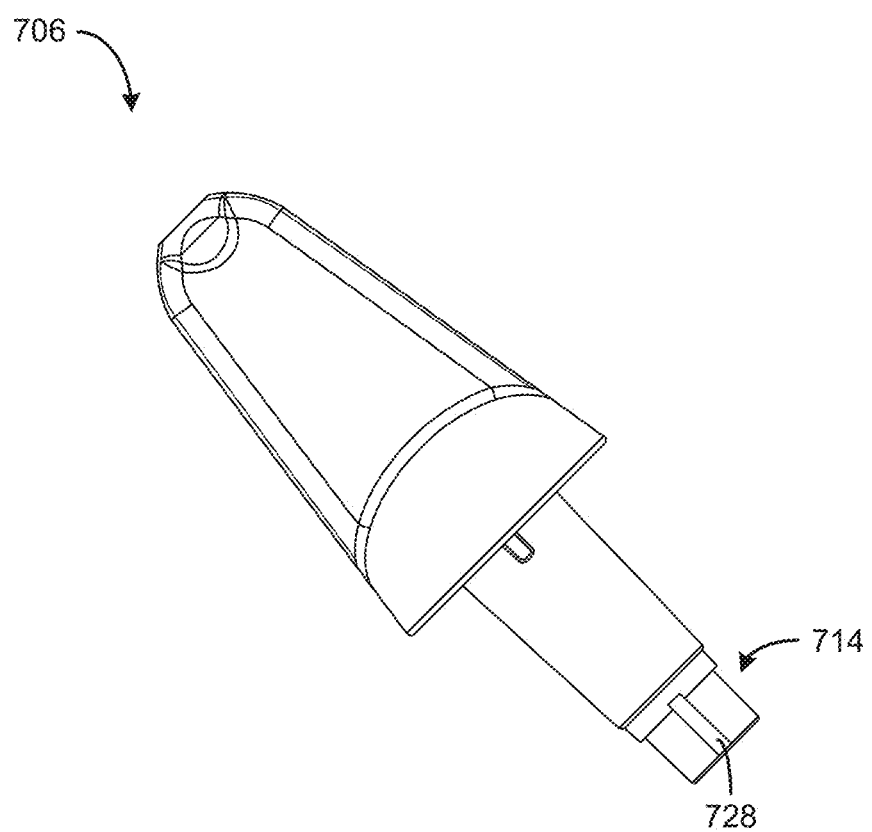
FIG. 7O is an exploded view of one embodiment of the device.

As shown in FIGS. 7F, 7G, and 7J, the inlet interface 714 is, for example, a ring, band, port, collar or strap interfacing with the capsule and the outer wall 708 of the exit channel 712 and in fluid communication with the propellant exiting the propellant canister 704. As shown in FIGS. 7C, 7E, 7F, 7K, 7L, 7M, 7N, 7O, and 7P, grooves 728a-b in the inlet interface 714 allow for access of the propellant from the propellant canister 704 into the compound container 720. An example of the grooves 728a-b includes but is not limited to channels, slots, radial ports, or passageways. The grooves 728a-b provide a pathway via the inlet interface 714 by which the propellant flows into the compound container 720.

In one example, there is a plurality of grooves 728a-b. The grooves 728a-b may be at equal spacing from each other. They may be of equal size to each other, or they may be of differing sizes. The grooves 728a-b run from a point of association of the exit opening 732 of the capsule with the outer wall 708 the exit channel 712.

In use, as shown by the direction of the arrows in FIG. 7D, the propellant flows into the compound container 720 via the grooves 728a-b. The exit channel 712 is aligned with the exit opening 732 of the compound container 720. The propellant flows in the grooves 728a-b of the inlet interface 714, into the compound container 720 to agitate the powder, and the powder and the propellant exit the capsule via the exit opening 732 congruent with the exit channel 712. The propellant and powder mixture are carried through the exit channel 712 through the nozzle 718 and exit the device 700 at the orifice 716 of the nozzle 718. In one example, the nozzle 718 may have one or a plurality of orifice 716. The plume exiting the nozzle 718 has a narrow spray plume.

Figure 7P:
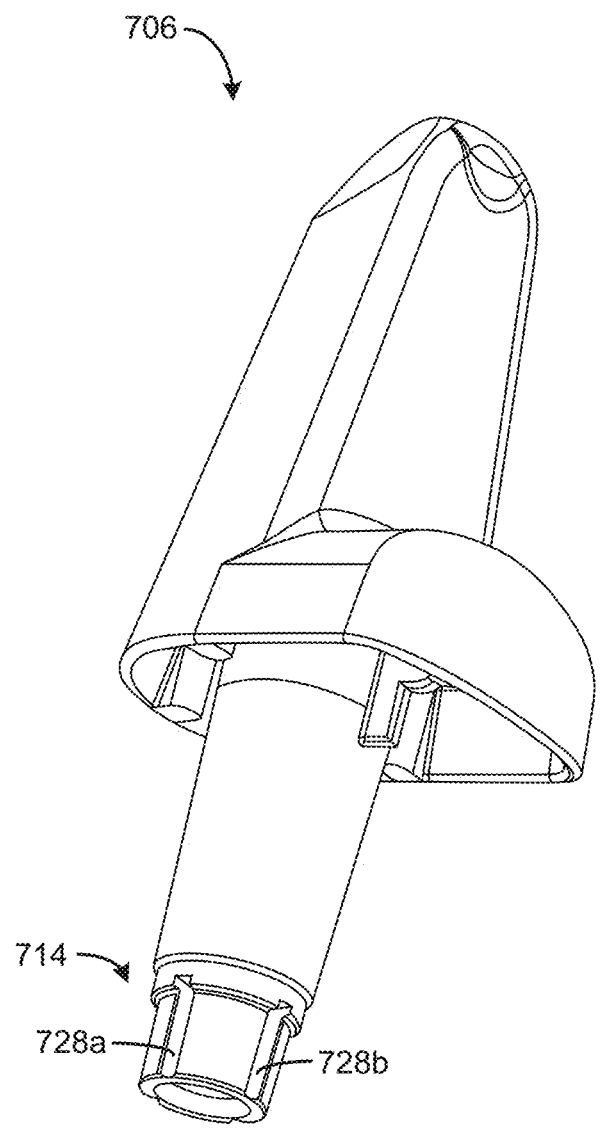
FIG. 7P is an exploded view of one embodiment of the device.
Figure 7Q:
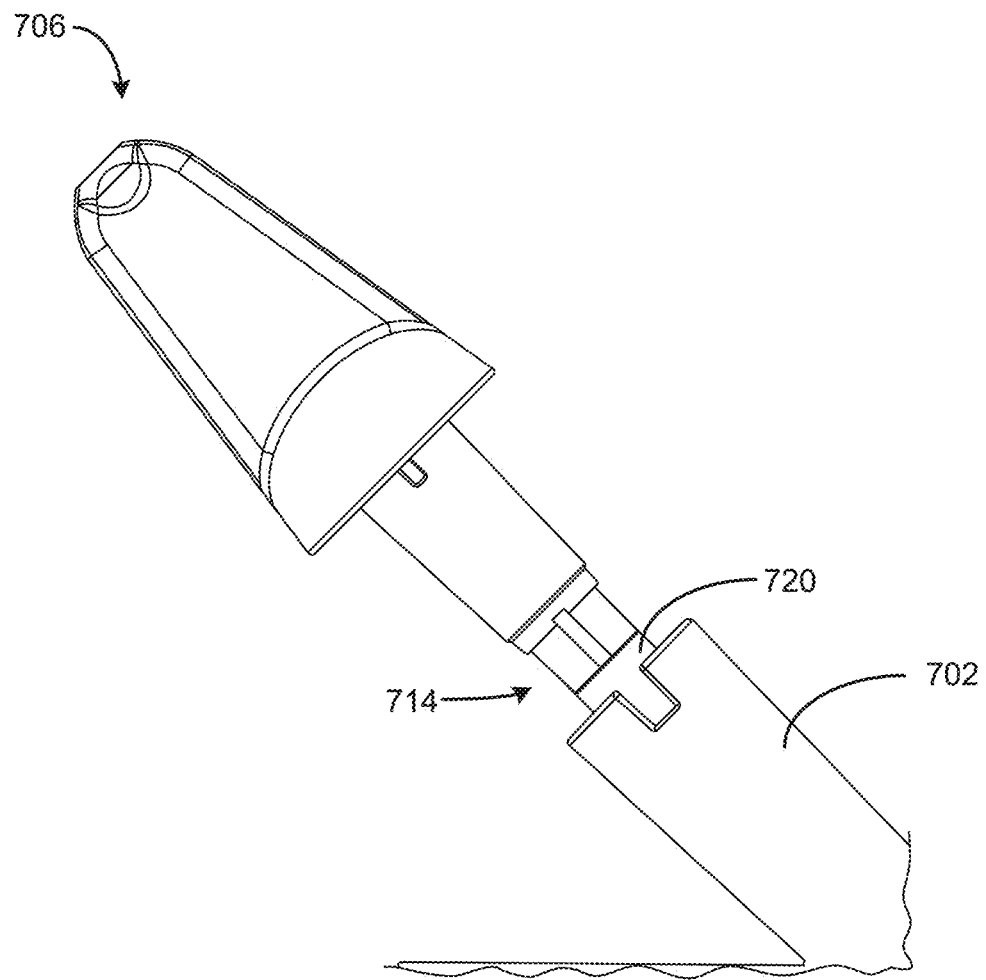
FIG. 7Q is a cross section of one embodiment of the device.
Figure 7R:
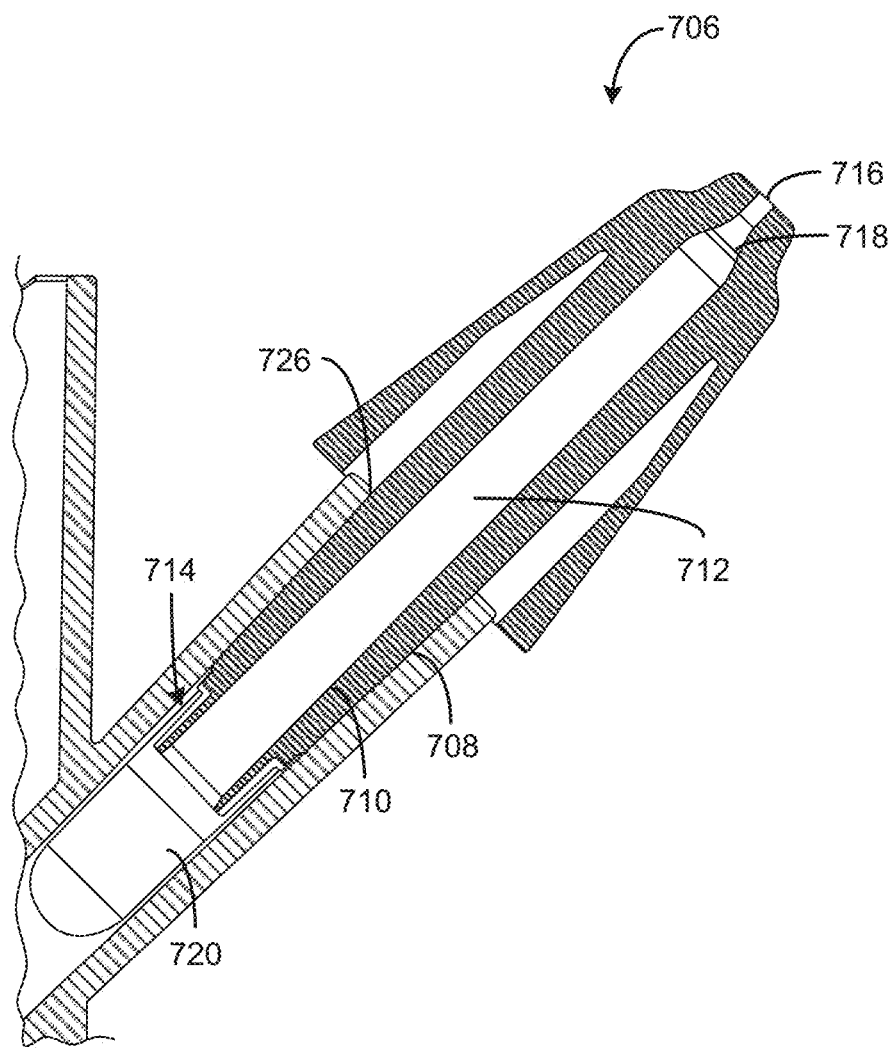
FIG. 7R is an exploded view of one embodiment of the device.
Figure 7S:
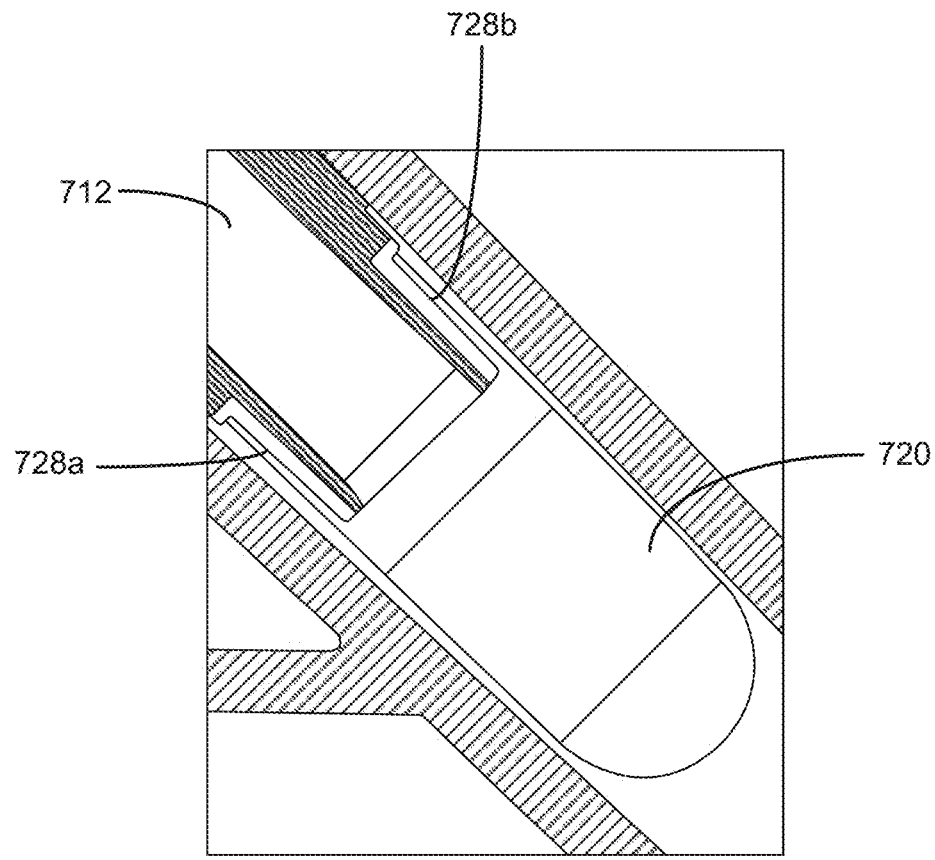
FIG. 7S is a view of a second embodiment of the device.

In one example of use of this embodiment, at time of use, the user separates a pre-filled capsule into its two halves. In one example, the capsule is prefilled with a powder compound. The half-capsule is inserted onto the tip 706. As shown in FIGS. 7P and 7Q, the tip 706 is then placed into the neck of an actuator body 702. A propelling gas, for example from either a refrigerant or compressed gas source, is directed through the actuator body 702, towards the filled powder capsule. Grooves 728a-b around the inlet interface 714 of the tip 706 and capsule introduce high velocity jets of propellant gas which agitate the dry powder into a suspension within the propellant gas (data not shown but confirmed with high speed close up video). Gas channels which introduce gas tangentially to the semispherical-shaped compound container 720 bottom to create jets which enhance stirring and entrainment of powder. Once the powder has been suspended, it is evacuated through the exit opening 732 and the exit channel 712 of the device 700.

Generally, when accelerating a powder formulation through a restricting orifice, any constricting junction will cause the powder to clog. Since the powder in this device 700 is suspended within the propellant gas prior to evacuation, it can be further throttled and directed without device clogging. This means that a much larger mass of powder can be delivered through a much smaller exit orifice and nozzle 718 without the device 700 being prohibitively long. The time from propellant actuation to end of delivery is less than 1 second.

Grooves 728a-b for gas flow in the proximal end of the tip 706 promote gas flow into the capsule which serves as the dose or compound container 720. In one example, the HFA gas is directed (e.g. orthogonally) at the surface of the powder dose residing in the capsule which creates rapid agitation and entrainment of the powder. The semispherical shape of the proximal end of the capsule promotes gas redirection to the exit channel 712 of the tip 706 as shown in FIG. 7D. The arrows of FIGS. 7B and 7D show the direction of propellant flow after the device 700 has been actuated.

The propellant canister 704 provides the propulsion for the device. The propellant canister 704 may be a canister or a container of a compressed gas or a liquefied propellant. Compressed gases include but are not limited to compressed air and compressed hydrocarbons. In one example, the compressed gas is nitrogen or carbon dioxide. Liquefied propellants include but are not limited to chlorofluorocarbons and hydrofluoroalkanes. The canister will generally be provided with a propellant valve 722 (not shown) by which the gas flow can be controlled.

In one example, the propellant canister 704 may be placebo filled, containing only liquid refrigerant propellant. At time of use, the propellant canister 704 is depressed, releasing a metered volume of liquid propellant into the system. The expanding propellant gas drives the dose expulsion and deposition of the device 700. In certain aspects, the propellant canister is a reusable component.

The actuator 702 attaches and seals to the propellant canister 704 and the tip 706, creating a pressurized flow path for the propellant gas. In certain aspects, the actuator body 702 is a reusable component.

In one example, the compound container 720 is a standard Size 3 drug capsule, although one of skill in the art would know how to use other sized drug capsules and modify the device 700 to fit same. Additionally, in another example, the compound container 720 may not be a capsule, but another container capable of containing a compound, such as but not limited to an ampoule. In one example, the ampoule may be made of plastic, and in one example it may be a blow fill sealed ampoule. To load the device 700, the user or clinician will separate a prefilled formulation containing capsule, discard the cap, and install the capsule body over the tip 706. An empty compound container 720 can also be filled by a clinician at time of use before installing the compound container 720 over the tip 706. In certain examples, the capsule is a disposable component.

The tip 706 receives the compound container 720 during loading, and is then pressed into the actuator body 702 prior to use. When the propellant canister 704 is activated, expanding propellant gas is introduced into the compound container 720 from radial grooves 728a-b around the inlet interface 714 of the tip 706. The resulting propellant gas jets agitate and entrain the powder formulation, which then exits through the nozzle 718 end of the tip 706. In one example, the tip 706 is a disposable component.

Figure 7T:
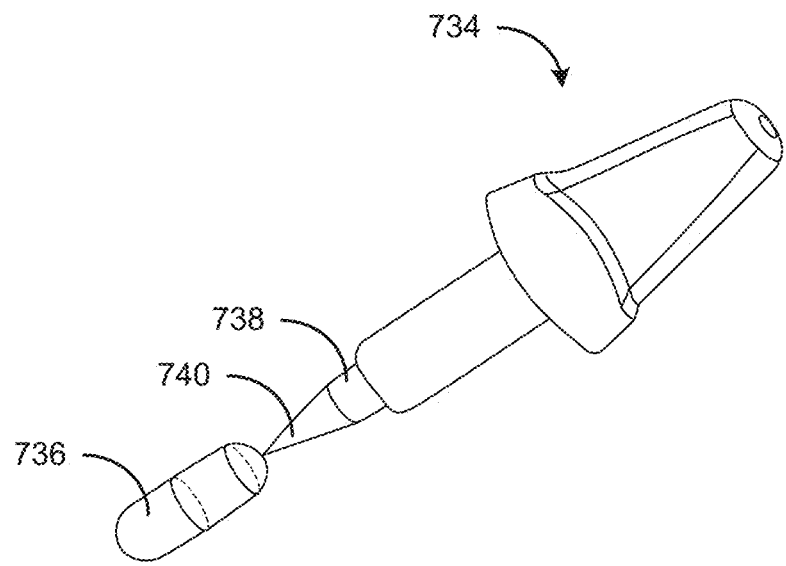
FIG. 7T is a view of a second embodiment of the device.
Figure 7U:
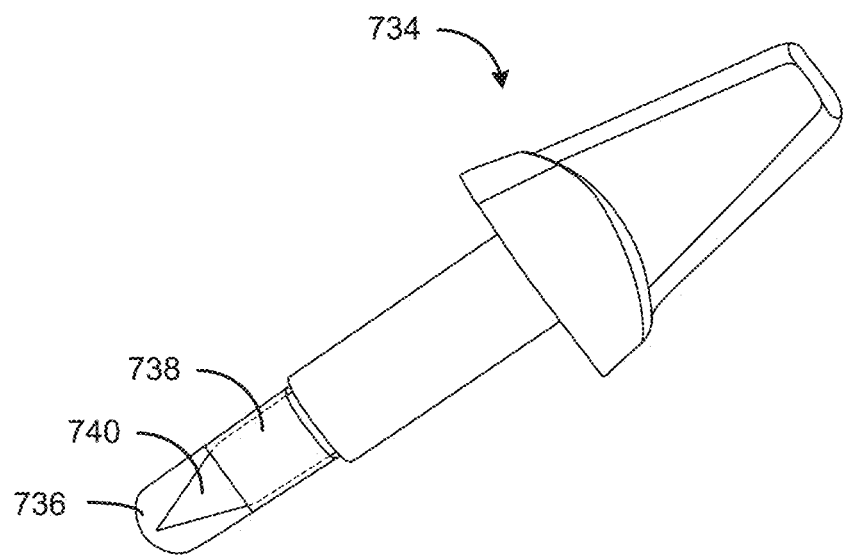
FIG. 7U is a view of the puncture member of the second embodiment.
Figure 7V:
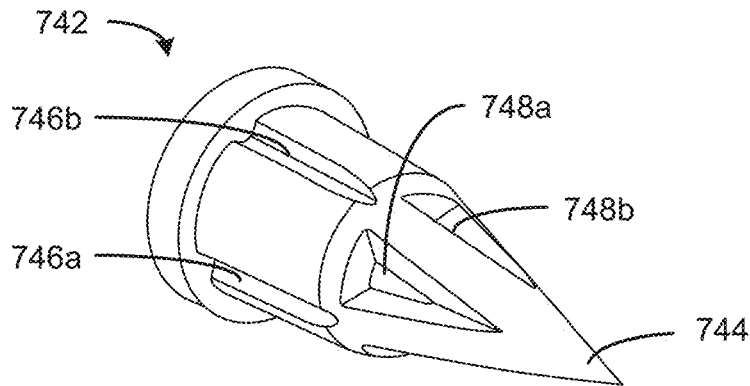
FIG. 7V is a view of the puncture member of the second embodiment.

In a second embodiment, a propellant canister 704 is in fluid communication with the inlet interface 738. As shown in FIGS. 7T and 7U, a capsule 736, in one example for containing a powder, is associated with the tip 734 of the device 700. As the tip 734 of the device 700 is associated with the actuator body 702, the capsule 736 is punctured. This puncture of the capsule 736 forms fits the punctured capsule snuggly around the puncture member 740 shown in FIGS. 7T and 7U. As shown in FIG. 7V, in this embodiment, the puncture member 742 forms the inlet puncture 738, for example but not limited to a collar, ring, band, port or strap, that associates with the exit opening 732 of the punctured capsule 736. The inlet puncture 738 is in fluid communication with the propellant canister 704. The propellant from the propellant canister 704 enters via puncture grooves 746 of the inlet puncture 738, flows along the puncture grooves of the inlet puncture 738 fitting snuggly within the punctured capsule 736. A shown in FIG. 7W, in the puncture point 744 of the inlet puncture there are a plurality of puncture openings 748. In this second embodiment, the inlet interface 714 may be integrally molded as a single piece or may consist of two or more pieces. In one example, the puncture member 740 may be a separately molded piece acting in association with the inlet puncture 738. The propellant from the propellant canister 704 flows into the puncture grooves 746, mixes with the powder in the capsule 736 and flows out of the puncture openings 748 in the puncture member 740. The puncture openings 748 in the puncture member 740 are congruent with the exit channel 712. The arrows of FIG. 7X show the route of the propellant flow. The exit channel 712 provides a route for the propellant and the powder to the nozzle 718. The mixture of propellant and powder exit the device 700 via the nozzle 718. The plume exiting the device 700 via the nozzle 718 is a narrow plume.

Figure 7W:
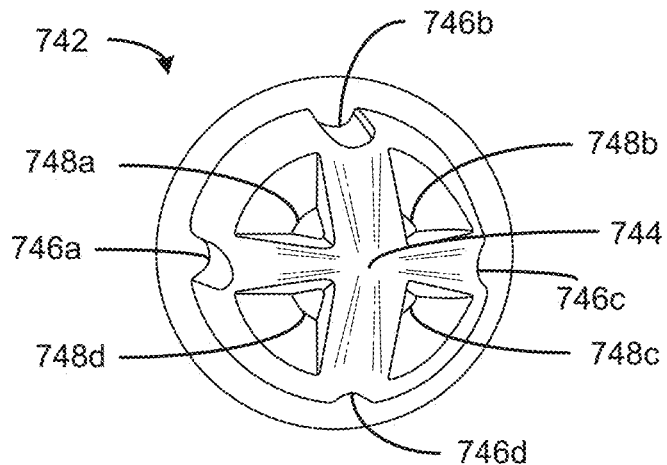
FIG. 7W is a view of the flow path in the second embodiment.
Figure 7X:
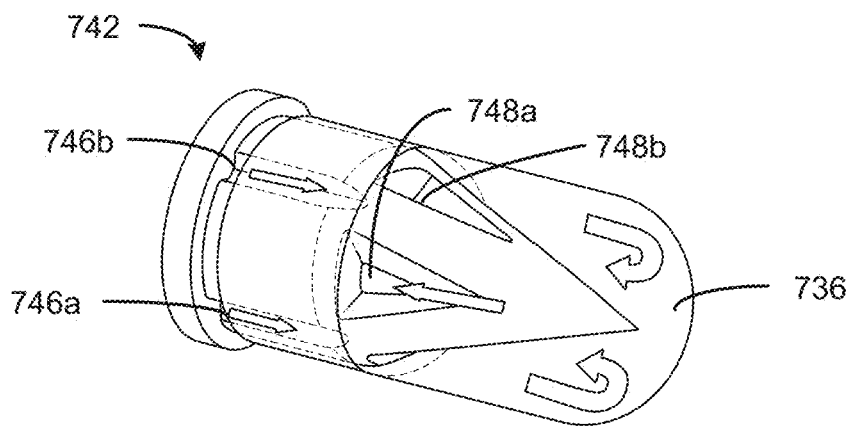
FIG. 7X is a view of the propellant flow path in the second embodiment.

As shown in FIGS. 7V and 7W, as an alternate to the capsule being manually separated prior to placement on the tip 734 includes an integrated capsule puncture 742 and propellant gas introduction component. In order to create a repeatable puncture of the capsule 736, the integrated puncture comes to a single point, puncture point 744. In one example, the puncture point is provided with separate radial expulsion openings 748 for the powder to be evacuated from.

As shown in FIG. 7X, by allowing the propellant flow path to be created with an inline puncture motion, it is easier for a user to load a tip 734, as the capsule 736 does not require manual manipulation and separation. In one example, an inlet puncture 738 would be integral with the tip 734 as part of device 700. In one example, the filled capsule 736 maybe filled and installed into either the actuator body 702 or tip 734 during device 700 manufacture. At time of use, a user applied linear motion would drive the puncture point 744 into the pre-filled capsule 736, creating a complete gas flow path for dosing prior to propellant actuation.

Example A

Powder Capsule

In one embodiment, a device was constructed and tested. Testing was conducted for residual powder in the compound container after actuation. The device has equivalent performance of powder delivery, as determined by residuals after actuation, when 2 or more, but less than 6 grooves for the gas inlet are used. In this example, the grooves and in combination with 63 mg of HFA propellant and a 0.040" orifice of the nozzle. Four grooves (every 90 degrees) were found to provide uniform gas delivery.

Dose Mass

Dose mass reproducibility testing was conducted. The standard deviation on dose delivery shows the device is capable of delivering consistent dose masses. The mean residual of dose left in the device was <5%, showing very little dose is lost in the device

TABLE 0

| n | 49 |
|---|---|
| Mean (mg) | 34.9 |
| Standard Deviation | 1.0 |
| Min | 32 |
| Max | 36.7 |
| Range | 4.7 |
| Mean % Residual | 3.8% |

Table 0: Mass reproducibility of final molded device, Values in milligrams 5.5.3.4. Intranasal Device with Plurality of Frits FIG. 9A illustrates another example non-human primate precision olfactory delivery device 900 used in the study 2037-003, 2037-004, 2037-006, 2037-007, and FIG. 9B illustrates a side view and a cross-sectional view of an actuator body 910 of the intranasal device 900 of FIG. 9A. The device 900 may deliver a compound that is a liquid, a powder, or some combination thereof. The device 900 includes a propellant canister 905, the actuator body 910, an extension tube 915, and a tip 920. Similar to the device 1, the propellant canister 905 is in fluid communication with the actuator body 910 such that propellant released from the propellant canister 905 travels through the actuator body 910, through the extension tube 915, through the tip 920, and out an exit opening 925 of the tip 920. A compound may be loaded into the tip 920 such that as the propellant travels through the tip 920, the propellant contacts the compound and propels the compound to the exit opening 925, where the propellant and compound exit as a plume.

Figure 9C:
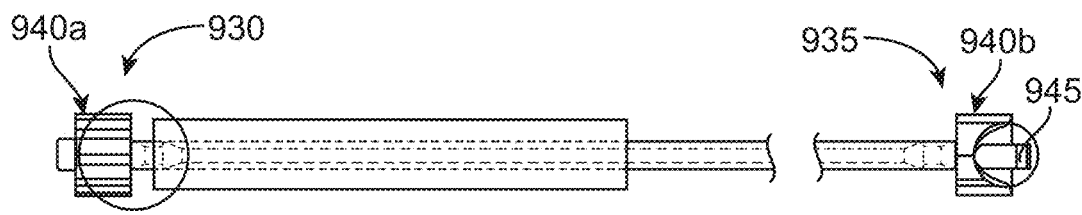
FIG. 9C illustrates a side view of an extension tube of the intranasal device of FIG. 9A.
Figure 9D:
FIG. 9D illustrates a zoomed-in view of a connecting interface at an end of the extension tube of FIG. 9C.
Figure 9E:
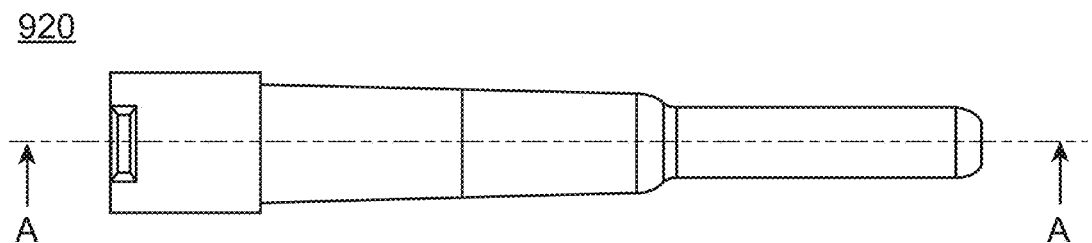
FIG. 9E illustrates a side view and a cross-sectional view of a tip of the intranasal device of FIG. 9A.
Figure 9E:
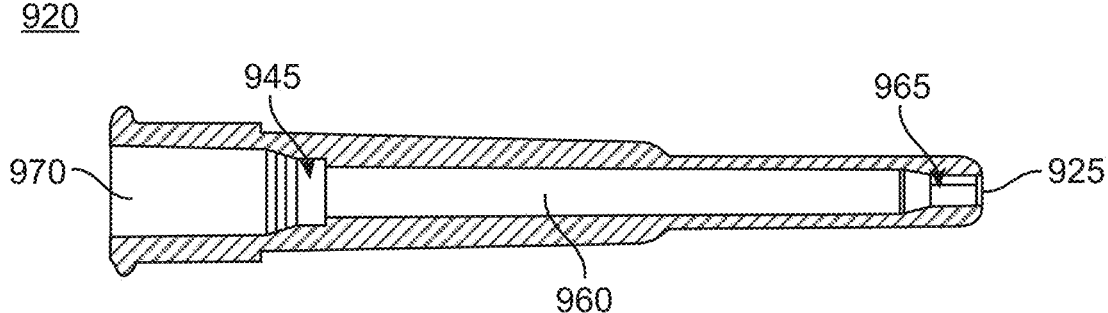

FIG. 9C illustrates a side view of the extension tube 915 of the intranasal device 900 of FIG. 9A. The extension tube 915 is a tube comprising an internal channel that creates fluid communication between the actuator body 910 and the tip 920. In the embodiments of FIGS. 9A to 9D, a first end 930 of the extension tube 915 couples to the actuator body 910 and a second end 935 of the extension tube 915 couples to the tip 920 each via a respective connecting interface 940a, 940b (collectively referred to as "940"). The connecting interface 940 comprises a luer lock having a male or a female end on each side of the luer lock. In the embodiment of FIGS. 9A to 9D, each connecting interface 940 comprises a luer lock having two male ends. Accordingly, the male ends of the connecting interface 840a insert into the actuator body 910 and the first end 930, respectively, and the male ends of the connecting interface 940b insert into the tip 920 and the second end 935, respectively. As illustrated in FIG. 9C, the second end 935 may include a plurality of frits 945 positioned within an internal channel of the luer lock. A frit 945 may be configured to convert a liquid propellant into a gas as the propellant passes through the frit 945. Alternatively, the extension tube 915 in FIG. 9B can be configured to convert liquid propellant into a gas. The frit 945 may be composed of porous material. The number of frits 945 may vary in different embodiments. As the number of frits increases, the strength of the plume may be reduced, for example, in terms of its impact force, velocity, plume width, other similar metrics, or some combination thereof. Similarly, the length of the extension tube 915 may be adjusted such that the propellant has a longer or shorter distance to travel through. Calibrating the strength of the plume may enable the device 900 to accurately deliver the compound to the nasal cavity. FIG. 9D illustrates a zoomed-in view of the connecting interface 940b at the second end 935 of the extension tube 915 of FIG. 9C—a first example embodiment 950 includes a single frit 945, and a second example embodiment 955 includes three frits 945 stacked in succession. The number of frits 945 may be selected based on the type of compound. For example, a single frit 945 may be used for a powder compound, while three frits 945 may be used for a liquid compound, or vice versa.

FIG. 9E illustrates a side view and a cross-sectional view of the tip 920 of the intranasal device of FIG. 9A. The tip 920 is designed to be inserted into a nasal opening. The tip 920 comprises an internal channel 960 and the exit opening 925 for delivering the compound to the nasal cavity. In the embodiment of FIG. 9E, the tip 920 comprises a frit 945 seated within the internal channel 960. The frit 945 may be configured to convert a liquid propellant into a gas as the propellant passes through the frit 945. The frit 945 may be composed of porous material. In the embodiment of FIG. 9E, tip 920 further comprises a nozzle 965 at a distal end of the tip 920 near the exit opening 925. The nozzle 965 may enhance deposition of the compound within the nasal cavity, such as to the upper olfactory region of a user. In some embodiments, the nozzle 965 may include a single orifice, and, in alternate embodiments, the nozzle 965 may include a plurality of orifices (e.g., between 2 to 11 orifices). In some embodiments, the tip 920 may not include a nozzle. Different embodiments of tips may be used based on different types of compounds to be delivered to the nasal cavity of the user. For example, a tip for delivering a powder compound may not include a nozzle, while a tip for delivering a liquid compound may include a nozzle, or vice versa. In addition, the number of orifices in the nozzle may similarly vary based on the type of compound. A compound may be loaded into the tip 920 such that the compound is contained within the internal channel 960. In the embodiment of FIG. 9E, the compound is loaded into the tip 920 through an opening 970 at a proximal end of the tip 920 before the frit 945 is seated within the internal channel 960. The frit 945 is then inserted to contain the compound inside the tip 920. In an alternate embodiment, for example an embodiment in which the tip 920 does not include a nozzle 965, the compound may be loaded into the tip through the exit opening 925. In the configuration of FIG. 9E, the propellant travels from the propellant canister 905, through the actuator body 910 and extension tube 915, through the tip 920 and contacts the frit 945, and then contacts the compound within the internal channel 960, propelling the compound through the exit opening 925, where the propellant and compound exit as a plume that is delivered within the nasal cavity of the user.

5.5.3.5. Exhalation Delivery System

In various embodiments, the delivery device is for intranasal administration. In some embodiments, the nasal delivery device is a device, and is used, as described in U.S. Pat. Nos. 9,468,727; 9,205,208; 9,119,932; 9,072,857; 8,596,278; 8,555,878; 8,327,844; 7,975,690; 7,740,014, 9,132,249; 8,047,202; 7,481,218; 7,934,503; 8,800,555; 9,108,015; 8,590,530; 9,144,652; 8,899,229; 8,171,929, 8,550,073; 9,272,104; 9,038,630; 9,010,325; 8,978,647; 9,067,034; and 8,522,778, the disclosures of which are incorporated herein by reference in their entireties. In particular embodiments, the device is an exhalation breath-actuated nasal delivery device described in U.S. Pat. Nos. 8,511,303; 7,841,337; 7,543,581; 7,347,201; 9,452,272; and 7,784,460, incorporated herein by reference in their entireties.

5.5.3.6. Breath-Actuated Inhaler

In various embodiments, the delivery device is for administration by oral inhalation. In particular embodiments, the device is passive and breath-actuated inhaler described in U.S. Pat. Nos. 7,032,593; 9,717,866; and 9,468,728, the disclosures of which are incorporated herein by reference in their entireties. The breath-actuated inhaler can be a dose-controlled, self-administered inhaler. In one embodiment, the device is a dry powder inhaler, similar to the Inbrija inhaler. The inhaler may not need to coordinate inhalation with a pump or other actuation.

5.6. Experimental Examples

The invention is further described through reference to the following experimental examples. These examples are provided for purposes of illustration only, and are not intended to be limiting.

5.6.1. Example 1: Non-Human Primate PK Studies

A series of powder formulations of L-DOPA (levodopa) with or without DDI (carbidopa or benserazide) were developed and manufactured to assess the pharmacokinetics of intranasal administration of levodopa in non-human primates ("NHP"). The goal of the powder formulation development was to obtain a formulation that, following intranasal delivery using a non-human primate Precision Olfactory Delivery ("nhpPOD") Device, would result in a rapid plasma concentration increase to >200-400 ng/mL, such that the formulation would be expected to positively impact "OFF" episodes in Parkinson's disease.

Six single dose PK studies in the cynomolgus monkey were performed to examine the PK following administration of a variety of powder L-DOPA formulations delivered by the intranasal route using the nhpPOD Device. The formulations examined included an unmodified crystalline powder (median particle size of about 50 µm), a sifted formulation containing crystalline L-DOPA particles with a defined size range of 20-40 µm, and spray dried formulations. Some of the tested formulations additionally included a dopamine decarboxylase inhibitor, either benserazide or carbidopa. The spray dried formulations further contained NaCl with and without HPMC, 1,2-distearoyl-sn-glycero-3-phosphocholine ("DSPC"), or maltoside. The placebo control, also delivered intranasally by the nhpPOD Device, was mannitol or microcrystalline cellulose ("MCC"). The formulations were delivered in the presence or in the absence of oral benserazide, a dopamine decarboxylase inhibitor.

Specifically, in the first single dose PK study ("2037-003"), a micronized crystalline levodopa powder (median particle size of about 50 µm) was administered without oral pretreatment of the animal with the DOPA decarboxylase inhibitor (DDI), benserazide. In the second single dose PK study ("2037-004"), spray dried formulations of L-DOPA were administered with the animal having received oral benserazide prior to L-DOPA administration. In the third single dose PK study ("2037-006"), spray dried L-DOPA formulations including L-DOPA, NaCl, HPMC, maltoside and/or DSPC were administered in the presence of oral benserazide. In addition, a comparable spray dried L-DOPA formulation that additionally included benserazide was administered. In this last group, animals were pretreated with oral benserazide, but the oral dose most closely preceding intranasal administration was omitted. In the fourth single dose PK study ("2037-007"), spray dried levodopa formulations from a second contract research organization that included maltoside at different concentrations (0.1, 0.5, 1%) were administered in the presence of oral benserazide. In the fifth single dose PK study ("2037-017"), a spray dried L-DOPA formulations that additionally included carbidopa (1:10 carbidopa:L-DOPA) were administered in the absence of oral benserazide. Some of the dried L-DOPA formulations further included a permeation enhancer, either maltoside, EDTA or propylene glycol. In the sixth single dose PK study ("2037-019"), spray dried L-DOPA formulations that additionally included carbidopa at different ratios (1:10, 1:20, 1:4 carbidopa:L-DOPA) were administered in the absence of pretreatment with oral benserazide. Some of these formulations included an amorphous form of carbidopa while some contained a crystalline form of carbidopa. In both the fifth and the sixth studies, animals in one group were treated with a comparable spray dried L-DOPA formulation without carbidopa after pretreatment with oral benserazide.

In each study, $C_{max}$ and $T_{max}$ were measured and compared to the value measured in other studies. Table 1 summarizes specific experimental conditions for each study.

TABLE 1

Non-human primate PK study designs

| | Study 2037-003 | Study 2037-004 | Study 2037-006 | Study 2037-007 | Study 2037-017 | Study 2037-019 |
|---|---|---|---|---|---|---|
| Drug | Micronized crystalline levodopa ($D_{50}$ = 54 µm) | Spray dried levodopa, amorphous and crystalline polymorphs | Optimized spray dried levodopa (CRO = Bend Research), amorphous and crystalline polymorphs with combinations of HPMC, DSPC and maltoside | Optimized spray dried levodopa from (CRO = Hovione), amorphous and crystalline characteristics, 0.1%, 0.5% and 1% maltoside tested along with formulations from different manufacturing processes | Optimized spray dried formulation including both levodopa and DDI carbidopa at 1:10 ratio (carbidopa:L-dopa), tested | Optimized spray dried formulation including both amorphous levodopa and DDI carbidopa in both amorphous and crystalline polymorphs at different ratios, 1:10, 1:20 or 1:4 carbidopa:L-dopa, tested |
| Dose | 10, 20, 40 mg | 20 mg (all groups) | 20 mg (all groups) | 20 mg (all groups) | 20 mg (all groups) | 20 mg (all groups) |
| Device | nhpPOD Device #1, higher impact force | nhpPOD Device #2, lower impact force | nhpPOD Device #2, lower impact force | nhpPOD Device #2, lower impact force | nhpPOD Device #2, lower impact force | nhpPOD Device #2, lower impact force |
| Administration | Single dose, Awake | Single dose, Awake | Single dose, Awake | Single dose, Awake | Single dose, Awake | Single dose, Awake |
| DDI[a] | None used | All groups: 5 mg oral benserazide ("BZ") at −24, −16, −8, −0.75 hr | Groups 1 to 4: 5 mg oral benserazide ("BZ") at 24, −16, −8, −0.75 hr Group 5: 5 mg oral BZ at −24, −16, −8 hr (no oral | All groups: 5 mg oral benserazide ("BZ") at −24, −16, −8, −0.75 hr | Group 1: received oral benserazide ("BZ") at −0.75 hr; L-DOPA formulation without carbidopa administered | Group 1: received oral benserazide ("BZ") at −0.75 hr; L-DOPA formulation without carbidopa administered |

TABLE 1-continued

| | Study 2037-003 | Study 2037-004 | Study 2037-006 | Study 2037-007 | Study 2037-017 | Study 2037-019 |
|---|---|---|---|---|---|---|
| | | | BZ at −0.75 hr); benserazide administered in combination with levodopa by nhpPOD | | Groups 2-5: no oral BZ at −0.75 hr; carbidopa administered in combination with levodopa by nhpPOD | Group 2-5: no oral BZ at −0.75 hr; carbidopa administered in combination with levodopa by nhpPOD |
| Plasma PK Time Points | 3, 7, 15, 30, 45, 60, 90, 120, 180, 240, 360 | 3, 7, 15, 30, 45, 60, 90, 120, 240, 360, 600 | 3, 7, 15, 30, 45, 60, 90, 120, 240, 360, 600 | 3, 7, 15, 30, 45, 60, 90, 120, 240, 360, 600 | 3, 7, 15, 30, 45, 60, 90, 120, 240, 360, 600 | 3, 7, 15, 30, 45, 60, 90, 120, 240, 360, 600 |
| Analysis | LC/MS/MS | Same LC/MS/MS assay, also assessed benserazide interference | Same LC/MS/MS assay as study #2 (2037-004) | Same LC/MS/MS assay as study #2 | Same LC/MS/MS assay as study #2 | Same LC/MS/MS assay as study #2 | notes:
[a] DDI refers to a peripherally-acting dopa decarboxylase inhibitor.
[b] n-Dodecyl β-D-maltoside ("DDN") was used as maltoside.

5.6.1.1. Single Dose Intranasal Pharmacokinetic Study in the Cynomolgus Monkey (Non-GLP, Research Study Number 2037-003)

A single dose PK study was performed in the cynomolgus monkey, where crystalline levodopa (L-DOPA) dry powder, manufactured by Teva, was administered intranasally using an nhpPOD Device (non-human primate Precision Olfactory Delivery Device). Two male and two female monkeys each were assigned to 5 groups according to the design outlined in Table 2. Control animals were dosed with mannitol (particle size <210 μm) dry powder, Groups 2-4 were dosed with unmodified crystalline L-DOPA (median diameter of the particle size distribution (D50) about 50 μm) and Group 5 was dosed with particle size sifted crystalline L-DOPA such that the particle size range was 20-40 μm. Blood samples (1.6 mL per time point with sodium metabisulfite stabilizer) were collected from fasted animals pre-dose, 3, 7, 15, 30, 45, 60, 90, 120, 180, 240 and 360 minutes after dosing in all groups. Plasma was isolated from whole blood and samples were frozen prior to analysis. PK non-compartmental analysis was performed on an individual animal basis using Phoenix WinNonlin (v6.3).

Study design is summarized in Table 2.

TABLE 2

Study Design (Study 2037-003)

| Group | Test Article | Number of animals (male/female) | Target Total Dose (mg) | Dose regimen |
|---|---|---|---|---|
| 1 | Placebo control (mannitol) | 2/2 | 10 | 10 mg dose to 1 naris |
| 2 | L-DOPA (crystalline, $D_{50}$ = 50 μm) | 2/2 | 10 | 10 mg dose to 1 naris |
| 3 | L-DOPA (crystalline, $D_{50}$ = 50 μm) | 2/2 | 20 | 10 mg dose to each naris |
| 4 | L-DOPA (crystalline, $D_{50}$ = 50 μm) | 2/2 | 40 | 20 mg to each naris |
| 5 | L-DOPA (crystalline, range 20-40 μm) | 2/2 | 10 | 10 mg dose to 1 naris |

The total doses achieved as well as the dose per cm² of calculated nasal surface area in each group are displayed in Table 3.

TABLE 3

Achieved L-DOPA doses in the monkey (Study 2037-003)

| Group | Target dose (mg) | Average body weight (kg) | Estimated Average dose (mg/kg) | Nasal Surface Area (cm²)[a] | Average Dose (mg/cm²) |
|---|---|---|---|---|---|
| 2 | 10 | 3.4 | 3.0 | 16.1 (one nostril) | 0.62 |
| 3[b] | 20 | 4.1 | 4.8 | 36.2 (both nostrils) | 0.55 |
| 4[c] | 40 | 3.4 | 11.8 | 32.4 (both nostrils) | 1.2 |
| 5 | 10 | 3.4 | 3.0 | 16.2 (one nostril) | 0.62 | notes:
[a]nasal surface area (NSA) was calculated using the equation, NSA = 15.1 + 5.1 (Body Weight$_{kg}$) (Harris, *J Aerosol Med.* 2003 Summer; 16(2): 99-105) ("Harris 2003"), and the group average body weight
[b]n = 5; male from Group 4 added to Group 3 for dose and PK analysis, as it only received one dose per nostril due to a visible nose bleed after the second spray.
[c]n = 3, one male was removed from Group 4 and added to Group 3 for dose and PK analysis, as it only received half the intended dose.

In a few animals, struggling during dose administration led to partial delivery of the intended dose. These animals included one female in Group 2, and one male and one female in Group 3. One male in Group 4 was not administered the 2$^{nd}$ dose (sprays 3 and 4) in either nostril due to red discharge from the nose/muzzle. As this animal only received 1 dose to both nostrils, he was subsequently allocated to Group 3 for dose and PK analysis.

Figure 1:
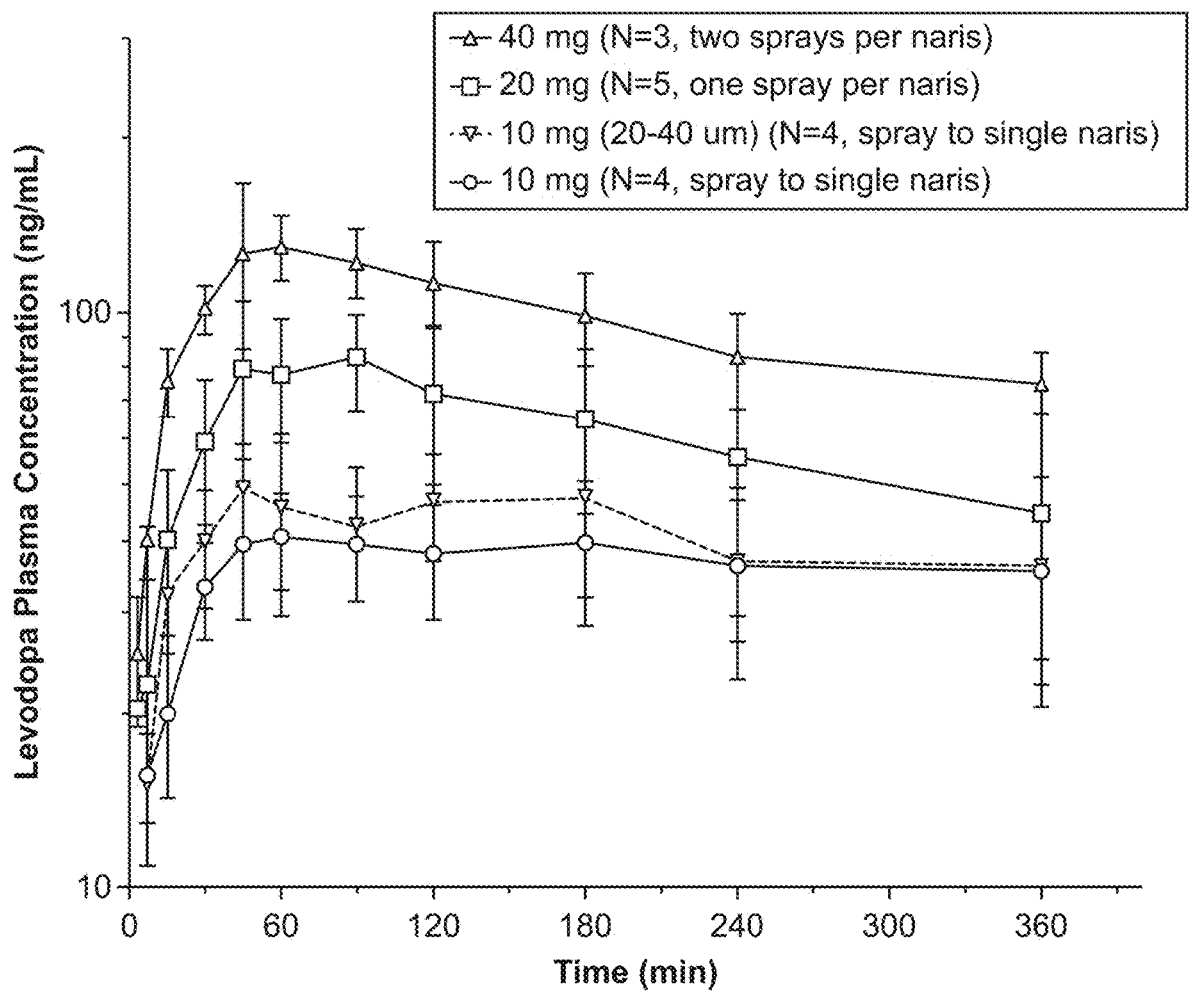

The calculated mean PK parameters are tabulated in Table 4, and the average plasma concentration-time curves are shown in FIG. 1. Following administration by the nhpPOD Device, unmodified L-DOPA delivered intranasally has dose-dependent pharmacokinetics. Further, it was observed that the small particle size may have a positive impact on the rate and extent of nasal uptake, as shown in the slight increase in AUC and C$_{max}$ (Table 4 and FIG. 1) for Group 5 (10 mg, 20-40 μm sifted) versus Group 2 (10 mg, D$_{50}$ 50 μm).

Following intranasal administration of unmodified crystalline L-DOPA, dose-dependent PK was observed. The earliest time point drug was measured was 3 minutes, and the median T$_{max}$ was delayed at approximately 60-90 minutes or greater. The results shown for Group 5, where a smaller particle size L-DOPA was administered (20-40 μm), suggests that a smaller particle size may increase the rate and extent of nasal uptake and subsequent systemic exposure, as a slightly higher AUC and C$_{max}$ was demonstrated compared to the unmodified bulk crystalline levodopa (D$_{50}$=50 μm) 10 mg group.

The maximum C$_{max}$ achieved following the 40 mg dosing was 150 ng/mL. Literature indicates plasma L-DOPA levels of 200-400 ng/mL are necessary for patients to switch from 'off' to 'on' during an OFF episode (*Sci Transl Med.* 2016 Oct. 12; 8(360):360ra136). Multiple factors may contribute to this lower than expected C$_{max}$ and longer than expected T$_{max}$, including, e.g., chemical and physical properties of the levodopa powder, such as crystalline polymorphic state and particle size, as well as the lack of a DOPA decarboxylase inhibitor (DDC inhibitor; DDI) pre-treatment.

5.6.1.2. Single Dose Intranasal Pharmacokinetic Study in the Cynomolgus Monkey (Non-GLP, Study 2037-004)

A single dose PK study was performed in the cynomolgus monkey, where L-DOPA dry powder (sifted or spray dried formulation) was administered intranasally using an optimized nhpPOD Device to reduce the impact of the propellant compared with the drug delivery device used in Study 2037-003.

Two male and two female monkeys each were assigned to four L-DOPA-dosed groups and one male and female were assigned to the control group according to the design outlined in Table 5. Each animal was pretreated with benserazide orally (size 3 capsule), receiving a 5 mg oral dose at 24, 16, 8 and 0.75 hours prior to being dosed intranasally with control material or L-DOPA. Control animals were dosed with MCC powder, Group 2 was dosed with particle size sifted crystalline L-DOPA (particle size range 20-40 μm), and Groups 3 to 5 were dosed with various excipient/spray dried formulations of L-DOPA. Blood samples (1.6 mL with sodium metabisulfite stabilizer) were collected from fasted animals pre-dose, 3, 7, 15, 30, 45, 60, 90, 120, 240, 360 and 600 minutes after dosing. Plasma was harvested from whole blood and samples were frozen prior to analysis by AIT Bioscience, Indiana, USA. Non-compartmental PK analysis was performed on an individual animal basis using Phoenix WinNonlin (v6.3).

TABLE 4

Mean (±SD) PK Data Following Intranasal Administration of L-DOPA to the Monkey (n = 3-5/group) (Study 2037-003)

| Group/No. of animals | Dose/Formulation | AUC$_{last}$ (ng*min/mL) | C$_{max}$ (ng/mL) | Median T$_{max}$ (minute) | t$_{1/2}$ (minute) |
|---|---|---|---|---|---|
| 2, n = 4 | 10 mg, Crystalline test article, D$_{50}$ 50 μm | 12943 ± 2707 | 51 ± 5 | 90 | 611 ± 74 |
| 3, n = 5 | 20 mg, Crystalline test article, D$_{50}$ 50 μm | 21820 ± 6716 | 95 ± 17 | 90 | 350 ± 170 |
| 4, n = 3 | 40 mg, Crystalline test article, D$_{50}$ 50 μm | 34185 ± 3441 | 150 ± 18 | 60 | 367 ± 102 |
| 5, n = 4 | 10 mg, Crystalline test article, particle size sifted 20-40 μm | 14523 ± 3733 | 56 ± 12 | 90 | 710 ± 745 | notes:
All control samples and pre-dose samples were below the level of quantitation ("LOQ") of 10 ng/mL.

TABLE 5

Study Design (study 2037-004)

Figure 2:
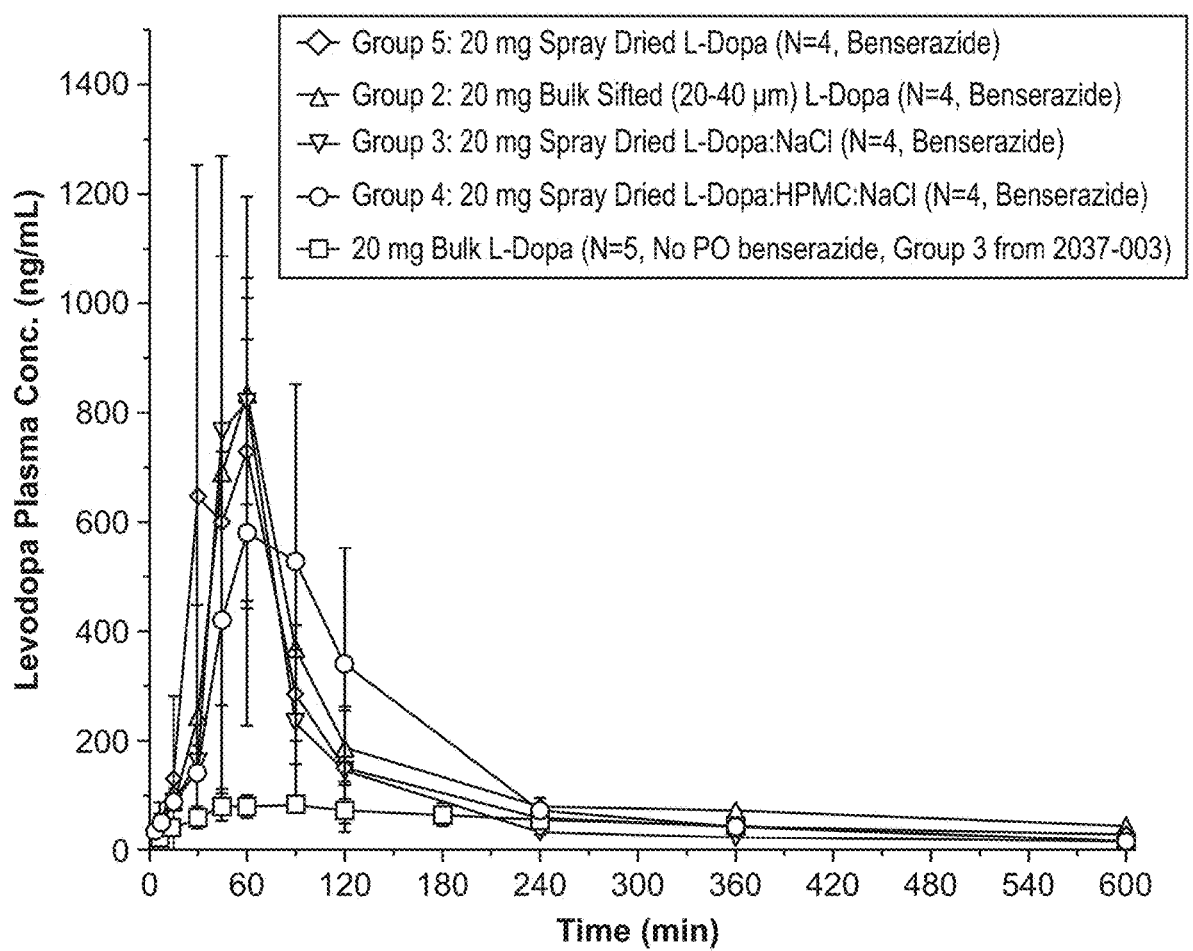

| Group | Test Article | Number of animals (male/female) | Target Total Dose (mg) | Dose Regimen |
|---|---|---|---|---|
| 1 | Control (microcrystalline cellulose) | 1/1 | 20 | 10 mg once to both nostrils |
| 2 | L-DOPA (sifted, 20-40 μm)[a] | 2/2 | 20 | 10 mg once to both nostrils |
| 3 | L-DOPA (Spray dried 1)[b] | 2/2 | 20 | 10 mg once to both nostrils |
| 4 | L-DOPA (Spray dried 2)[c] | 2/2 | 20 | 10 mg once to both nostrils |
| 5 | L-DOPA (Spray dried 3)[d] | 2/2 | 20 | 10 mg once to both nostrils | notes:
[a] particle size sifted, 20-40 μm, manufactured by Teva
[b] L-DOPA:NaCl, ratio of 98:2, manufactured by Bend Research, Oregon, USA
[c] L-DOPA:HPMC:NaCl, ratio of 70:28:2, manufactured by Bend Research, Oregon, USA
[d] spray dried L-DOPA manufactured by Bend Research, Oregon, USA Abbreviations HPMC, hydroxypropylmethyl cellulose
NaCl, sodium chloride The achieved total doses and dose per $cm^2$ of calculated nasal surface area are detailed in Table 6 and the average plasma concentration-time curves are shown in FIG. 2.

TABLE 6

Achieved L-DOPA Doses in the Monkey (n = 4/group) (study 2037-004)

| Group | Target dose (mg) | Average body weight (kg) | Estimated Average dose (mg/kg) | Nasal Surface Area $(cm^2)$[a] | Average Dose $(mg/cm^2)$ |
|---|---|---|---|---|---|
| 2 | 20 | 4.4 | 4.5 | 37.7 (both nostrils) | 0.53 |
| 3 | 20 | 4.0 | 5.0 | 35.4 (both nostrils) | 0.57 |
| 4 | 20 | 4.6 | 4.4 | 38.5 (both nostrils) | 0.52 |
| 5 | 20 | 4.2 | 4.7 | 36.7 (both nostrils) | 0.54 | notes:
[a] Nasal surface area (NSA) was calculated using the equation, NSA = 15.1 + 5.1($BW_{kg}$) (Harris 2003), and the group average body weight.

Animals tolerated dosing intranasally with placebo and L-DOPA. Two L-DOPA males jerked their heads after actuation of the intranasal dose, but a complete dose was delivered. A puff of powder left the nostril of one male in Group 3 directly after administration.

The calculated mean PK parameters for all animals are shown in Table 7, and the mean plasma concentration-time curves are shown in FIG. 2. Similar pharmacokinetics were observed across the formulations containing crystalline particle size sifted L-DOPA (20-40 μm) (Group 2), spray dried L-DOPA:NaCl (Group 3), and spray dried L-DOPA (Group 5), which showed $C_{max}$ concentrations of >900 ng/mL, well above the threshold necessary for efficacy of 'off' episode treatment. These $C_{max}$ levels were significantly higher, approximately 10-fold, compared to $C_{max}$ levels measured in the absence of the DDC inhibitor, benserazide (compare Table 4). The median $T_{max}$ observed with these formulations was 45-60 minutes, an improvement over the $T_{max}$ observed in the absence of a dopa decarboxylase inhibitor. The spray dried L-DOPA:HPMC:NaCl formulation resulted in a slightly lower $C_{max}$ (785 ng/mL) and longer $T_{max}$ than the other formulations. HPMC is a commonly used excipient that increases residence time on the nasal epithelium, though these results suggest that HPMC may slow the rate of uptake of L-DOPA across the epithelium.

TABLE 7

Mean (±SD) PK Parameters for L-DOPA Following Intranasal Administration in the Monkey (n = 4/group) with Oral Benserazide pretreatment (4 × 5 mg over 24 hours)

| Group | Dose/Formulation | $AUC_{last}$ (ng*min/mL) | $C_{max}$ (ng/mL) | Median $T_{max}$ (minute) | $t_{1/2}$ (minute) |
|---|---|---|---|---|---|
| 2 | 20 mg, 20-40 μm bulk sifted | 87813 ± 26577 | 1030 ± 297 | 53 | 344 ± 85 |
| 3 | 20 mg, spray dried L-DOPA:NaCl (98:2) | 61760 ± 14987 | 962 ± 460 | 53 | 272 ± 132 |
| 4 | 20 mg, spray dried L-DOPA:HPMC:NaCl (70:28:2) | 81446 ± 31220 | 785 ± 234 | 60 | 153 ± 47 |
| 5 | 20 mg, spray dried L-DOPA | 76171 ± 21566 | 917 ± 358 | 45 | 230 ± 68 |

Abbreviations:
HPMC, hydroxypropylmethyl cellulose;
NaCl, sodium chloride

In summary, the maximum mean plasma level achieved was 1,030 ng/mL following delivery of 20 mg crystalline particle size sifted L-DOPA (Teva), although two of the spray dried formulations, L-DOPA:NaCl and L-DOPA (Bend) achieved similar $C_{max}$ levels (>900 ng/mL). Improved (faster) $T_{max}$ values (45-60 min) were observed in this study for all L-DOPA formulations tested compared to L-DOPA administered in the absence of benserazide (>90 min; study 2037-003).

Exposure levels (AUC) increased 3- to 4-fold when L-DOPA was administered by an optimized nhpPOD Device with oral benserazide pretreatments (5 mg×4 doses over 24 hours), and overall the large AUC and long half-life for all groups suggest reasonable absorption of L-DOPA across the nasal epithelium regardless of formulation tested in this study.

The control group male had no measurable L-DOPA LOQ of 10 ng/mL) in plasma samples collected at any time point. The control group female, however, did have low levels of L-DOPA in plasma samples collected from 3 to 120 minutes (12.7-20.3 ng/mL). This was considered likely to be due to low endogenous levels of L-DOPA.

5.6.1.3. Single Dose Intranasal Pharmacokinetic Study in the Cynomolgus Monkey (Non-GLP, Study 2037-006)

A third single dose PK study was performed in the cynomolgus monkey, where L-DOPA dry powder (spray dried) formulations were administered intranasally using an nhpPOD Device. Two male and two female monkeys each were assigned to five groups. Each group was administered a different spray dried formulation of L-DOPA, according to the design outlined in Table 8.

Each animal in Groups 1-4 was pretreated with oral benserazide (size 3 capsule) such that each animal received a 5 mg oral dose of DDI at 24, 16, 8 and 0.75 hr prior to being dosed intranasally with L-DOPA. Animals in Group 5 were pretreated with a 5 mg capsule of oral benserazide at 24, 16, and 8 hours prior to dosing intranasally with a formulation containing both L-DOPA and benserazide, but were not pretreated with oral benserazide at 0.75 hr prior to being dosing intranasally. Group 5 animals received intranasal benserazide as part of the nhpPOD Device treatment.

Blood samples (1.6 mL stabilized with sodium metabisulfite) were collected from fasted animals pre-dose, 3, 7, 15, 30, 45, 60, 90, 120, 240, 360 and 600 minutes after dosing from animals in all groups. Plasma was isolated from whole blood and samples were frozen prior to analysis by AIT Bioscience, Indiana, USA. Non-compartmental PK analysis was performed on an individual animal basis using Phoenix WinNonlin (v6.3).

TABLE 8

Study Design (study 2037-006)

| Group | Test Article | Number of animals (M/F) | Target Total Dose (mg) | Dose Regimen |
|---|---|---|---|---|
| 1 | L-DOPA:NaCl:HPMC:DSPC (68:2:16:14) | 2/2 | 20 | 10 mg once to both nostrils |
| 2 | L-DOPA:NaCl:HPMC:DSPC (68:2:23:7) | 2/2 | 20 | 10 mg once to both nostrils |
| 3 | L-DOPA:NaCl:HPMC:DSPC (68:2:23:7) | 2/2 | 20 | 10 mg once to both nostrils |
| 4 | L-DOPA:NaCl:HPMC:maltoside (68:2:23:7) | 2/2 | 20 | 10 mg once to both nostrils |
| 5 | L-DOPA:NaCl:Benserazide:HPMC:DSPC (68:2:7:16:7) | 2/2 | 20 | 10 mg once to both nostrils |

Abbreviations:

DSPC, 1,2-distearoyl-sn-glycero-3-phosphocholine;

F, female;

HPMC, hydroxypropyl methyl cellulose;

M, male;

NaCl, sodium chloride;

maltoside, n-dodecyl-β-D-maltopyranoside

Figure 3A:
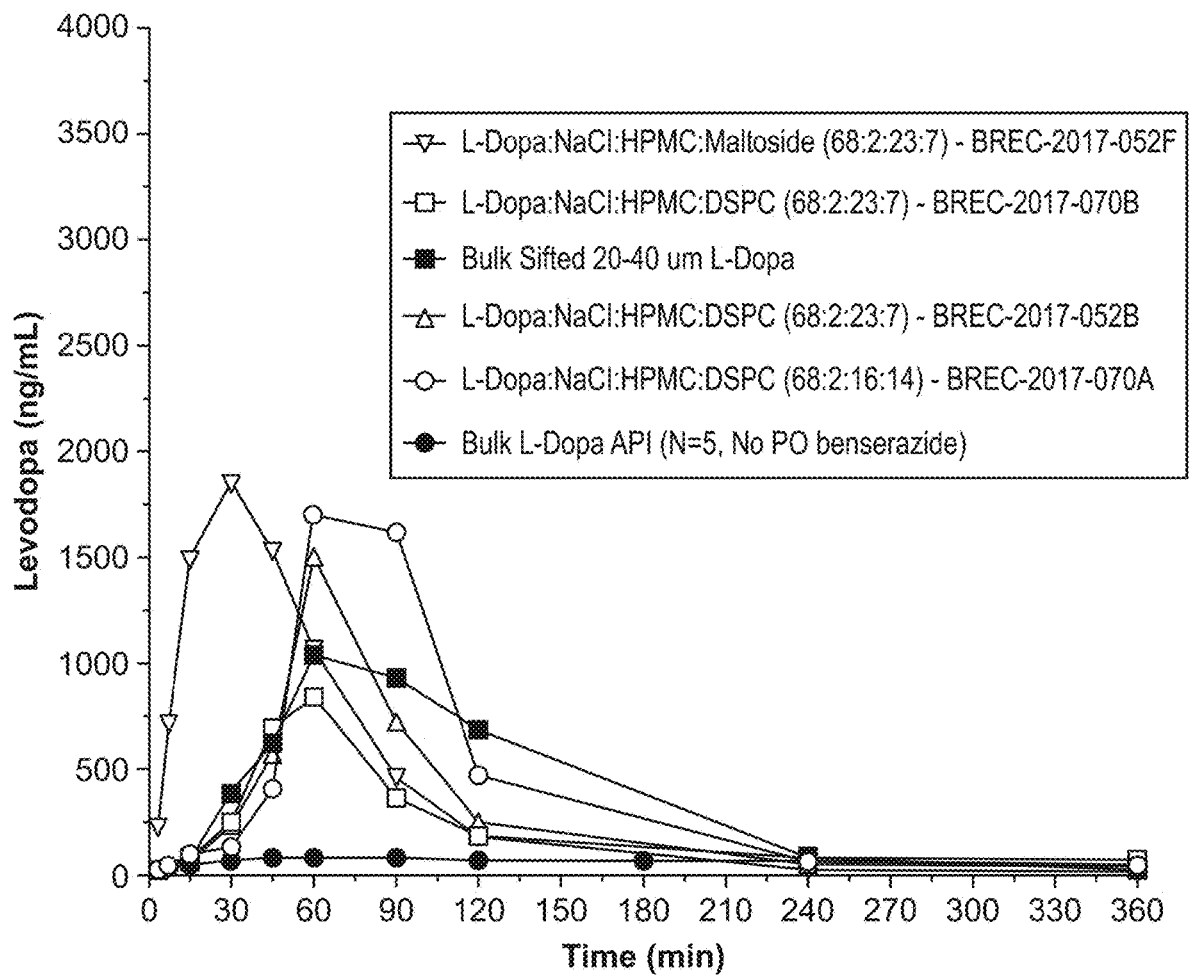
Figure 3B:
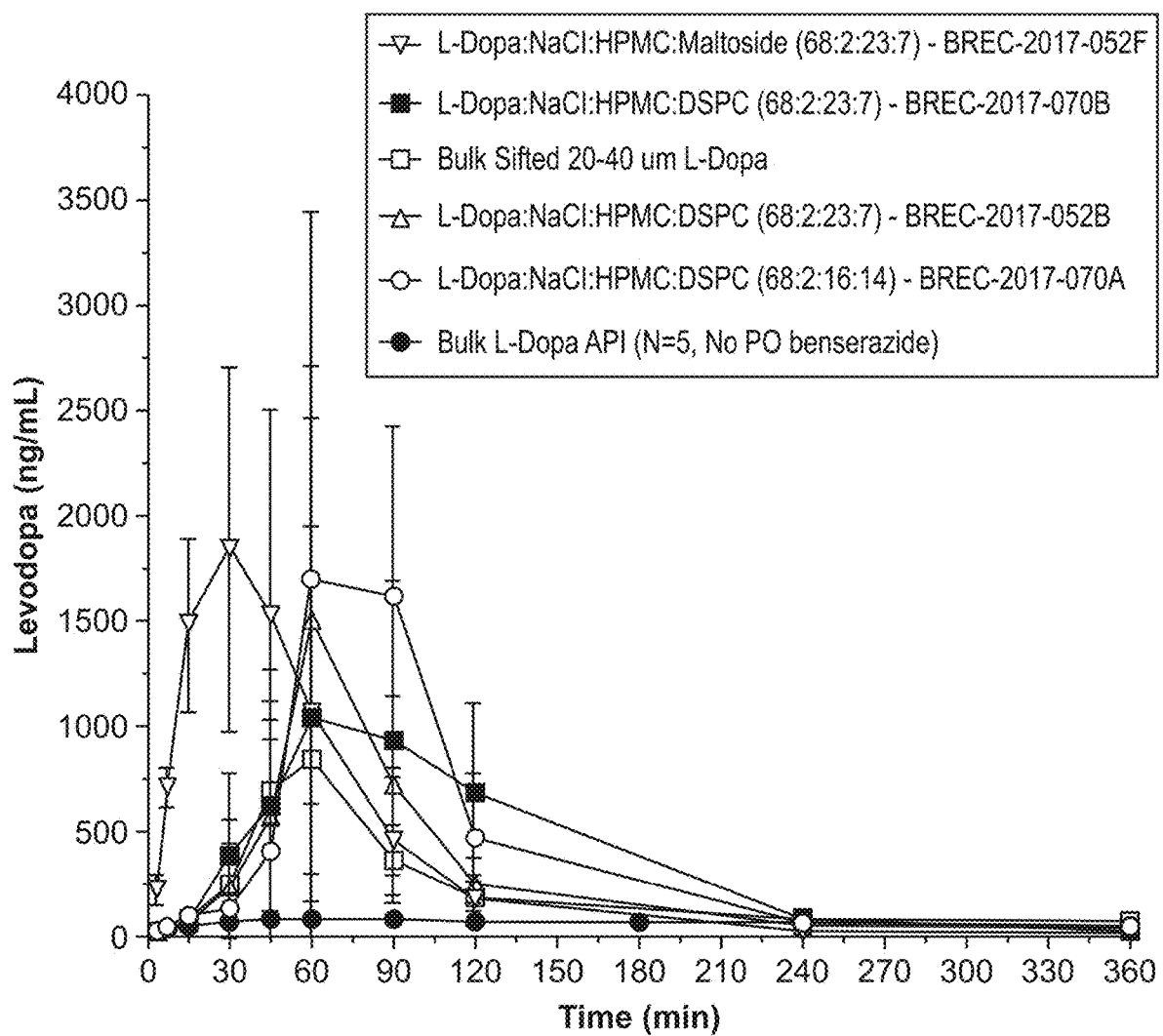
Figure 3C:
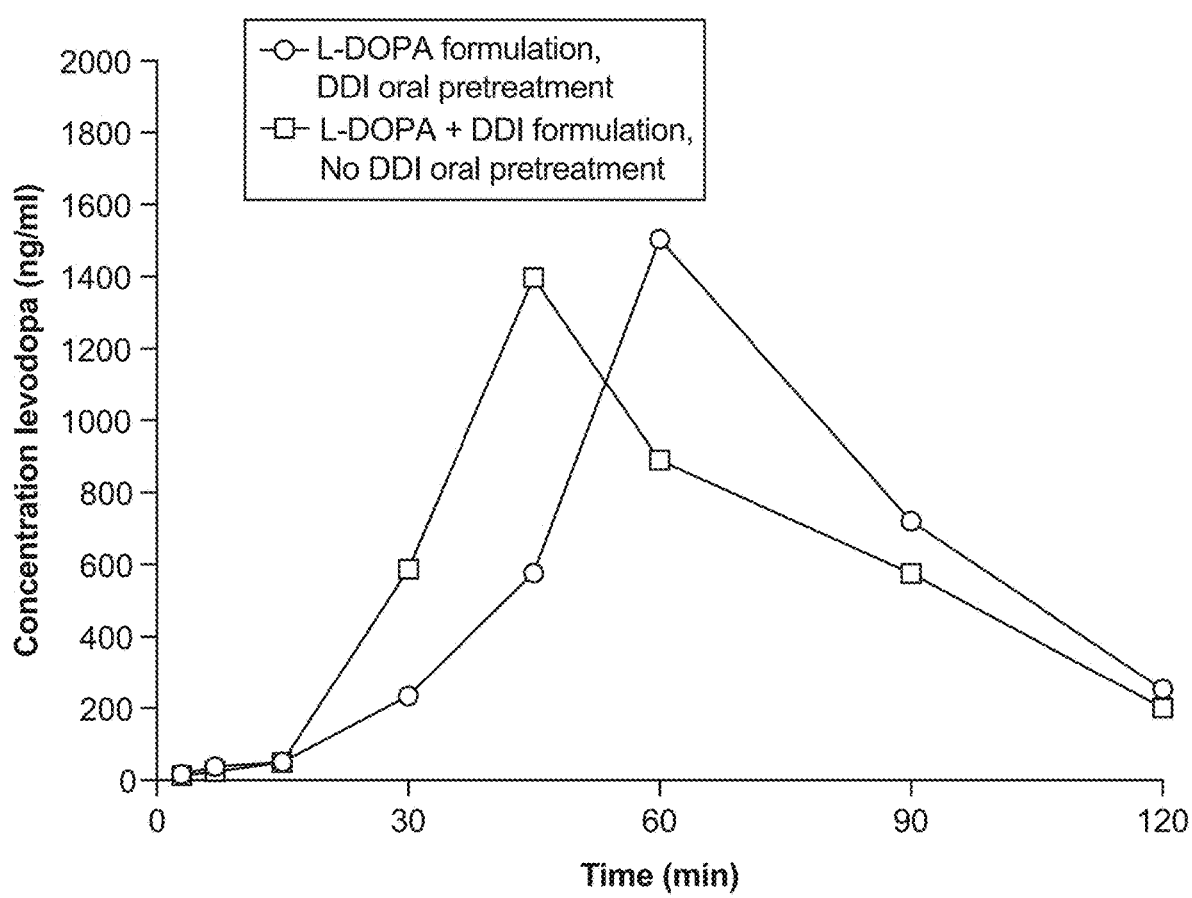
Figure 4A:
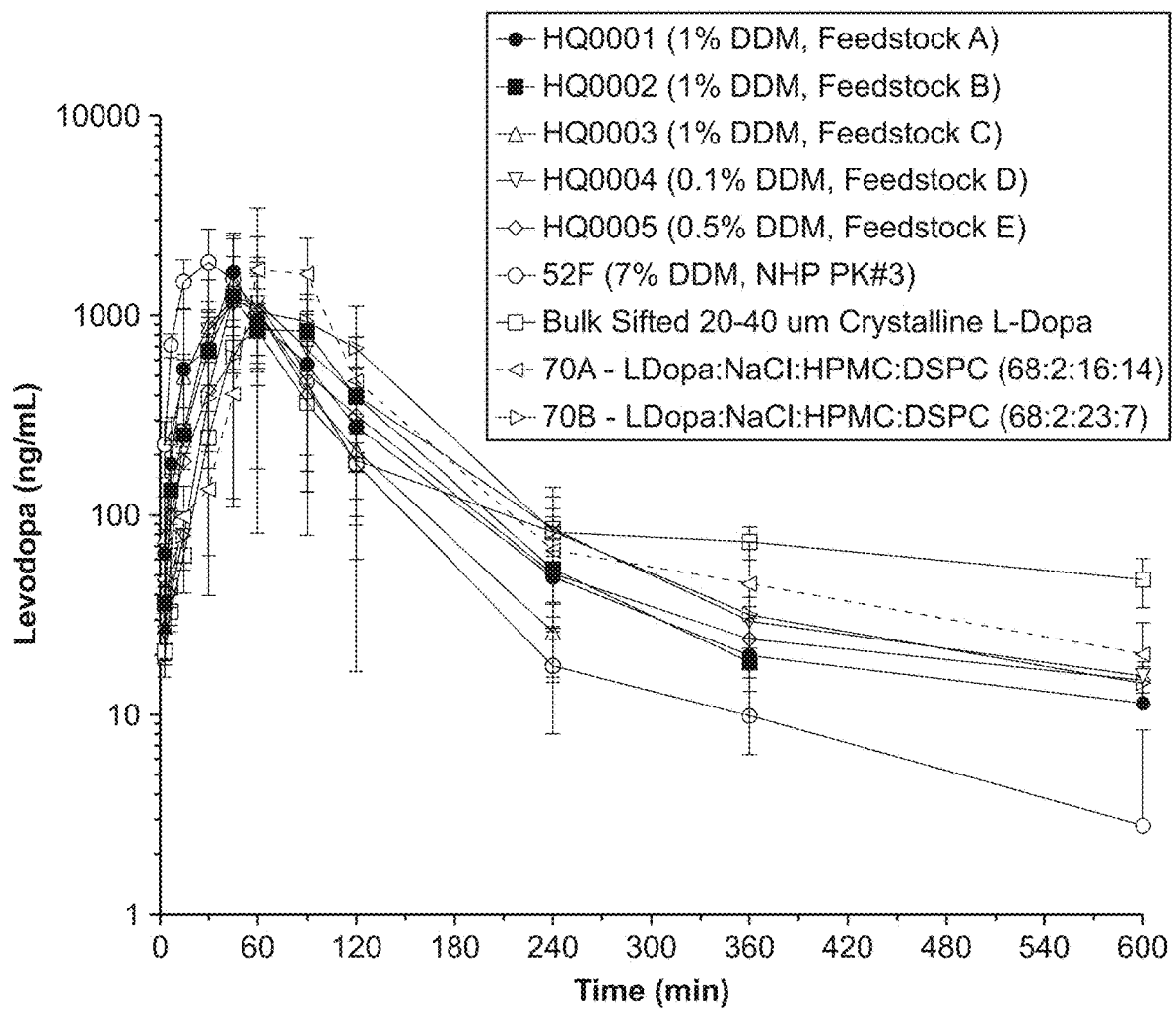
Figure 4B:
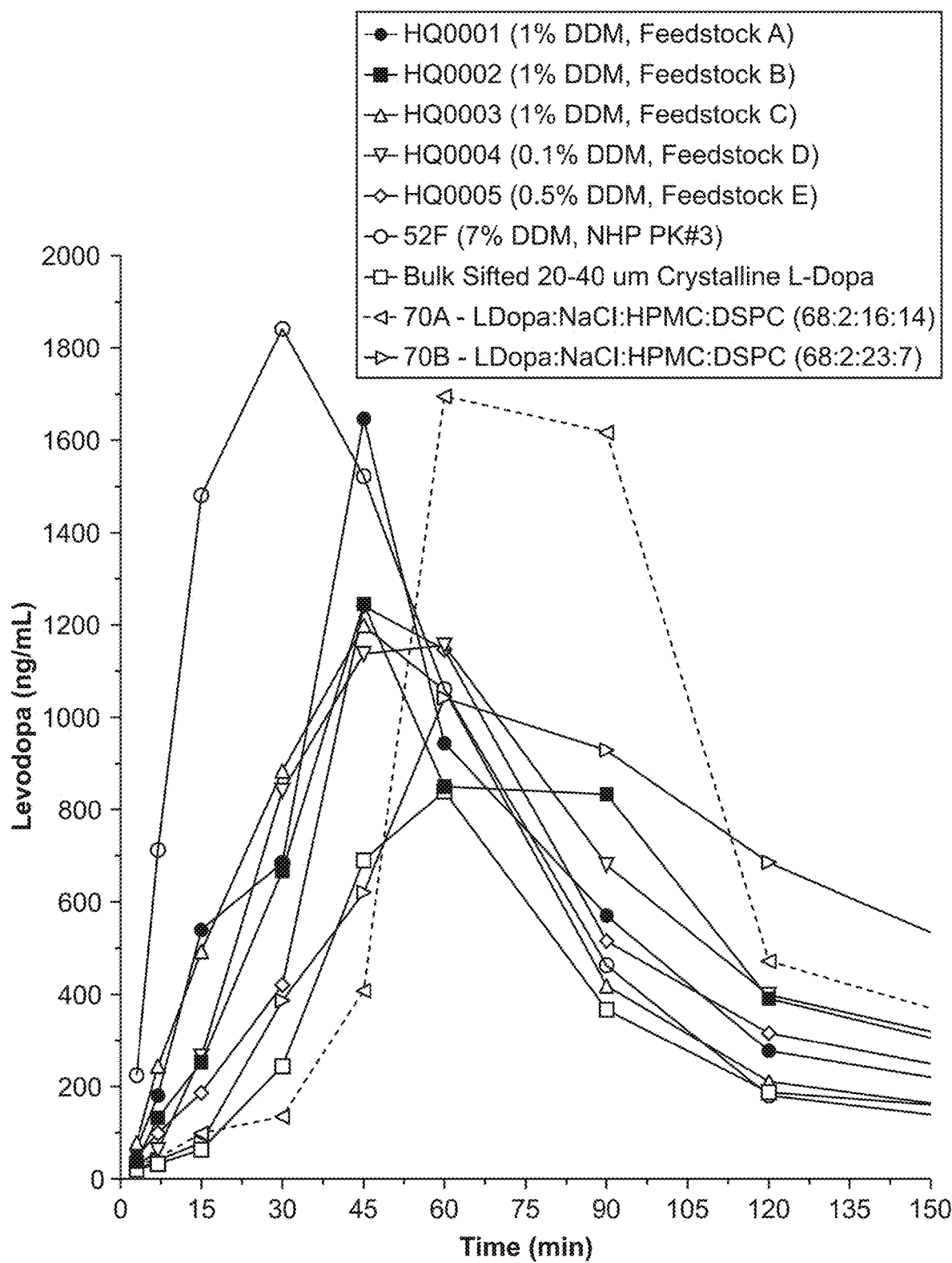
Figure 4C:
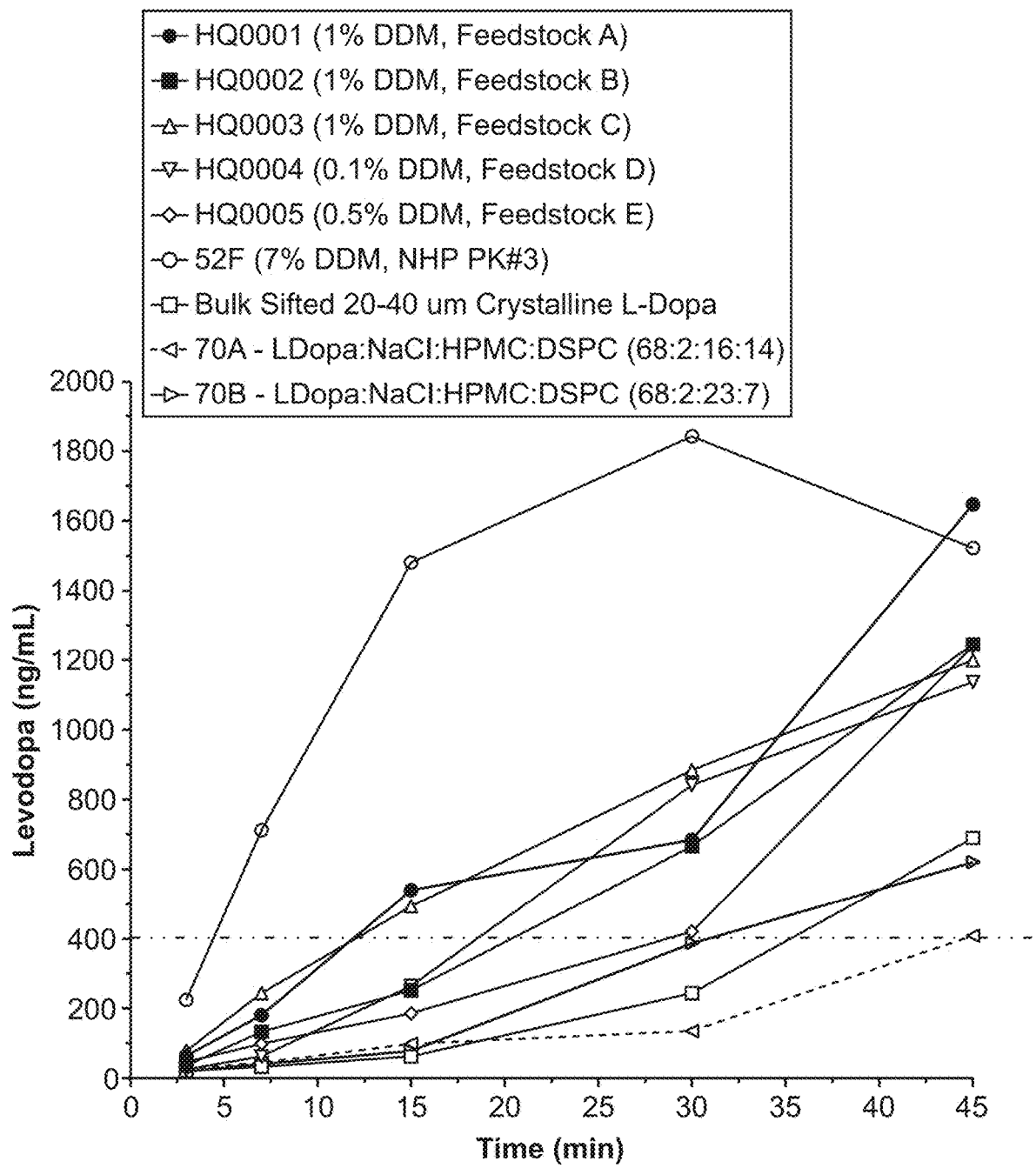
Figure 5A:
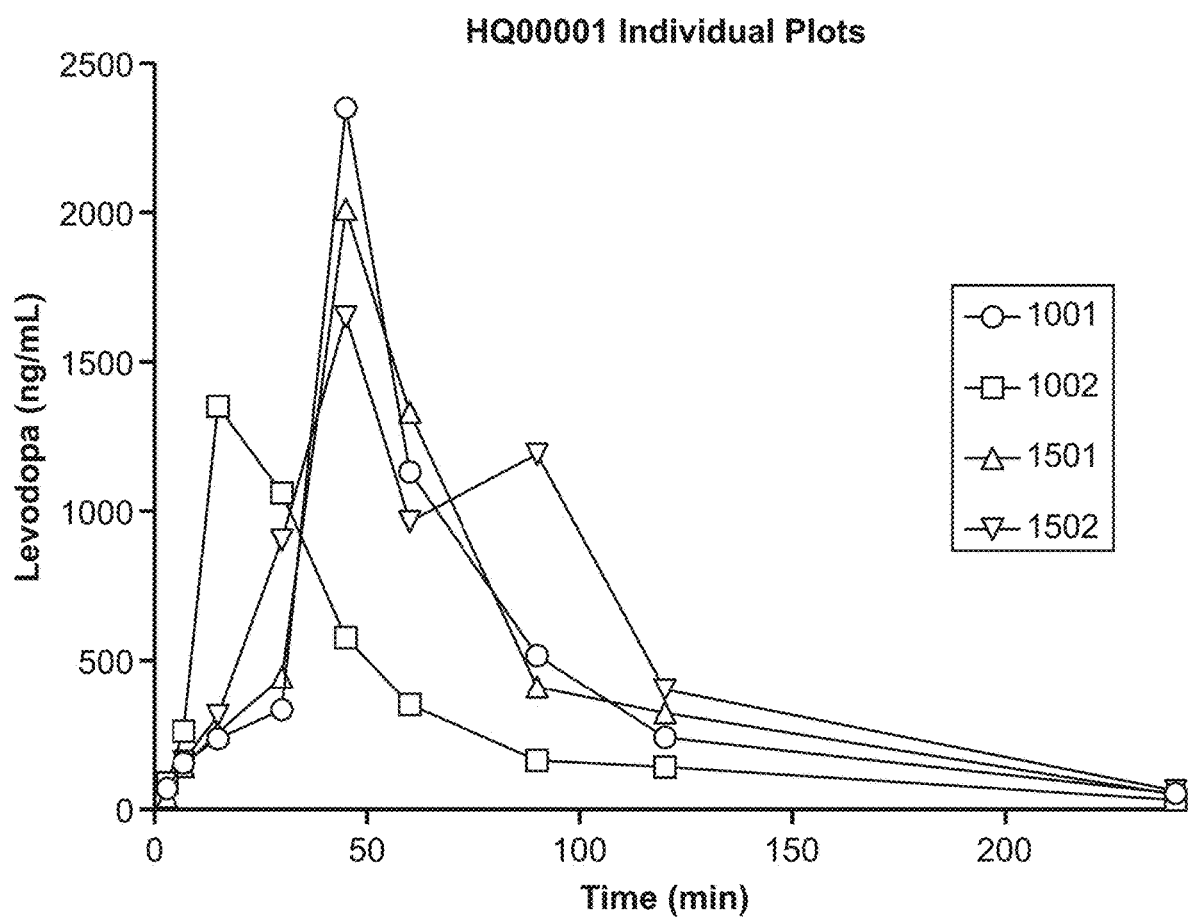
Figure 5B:
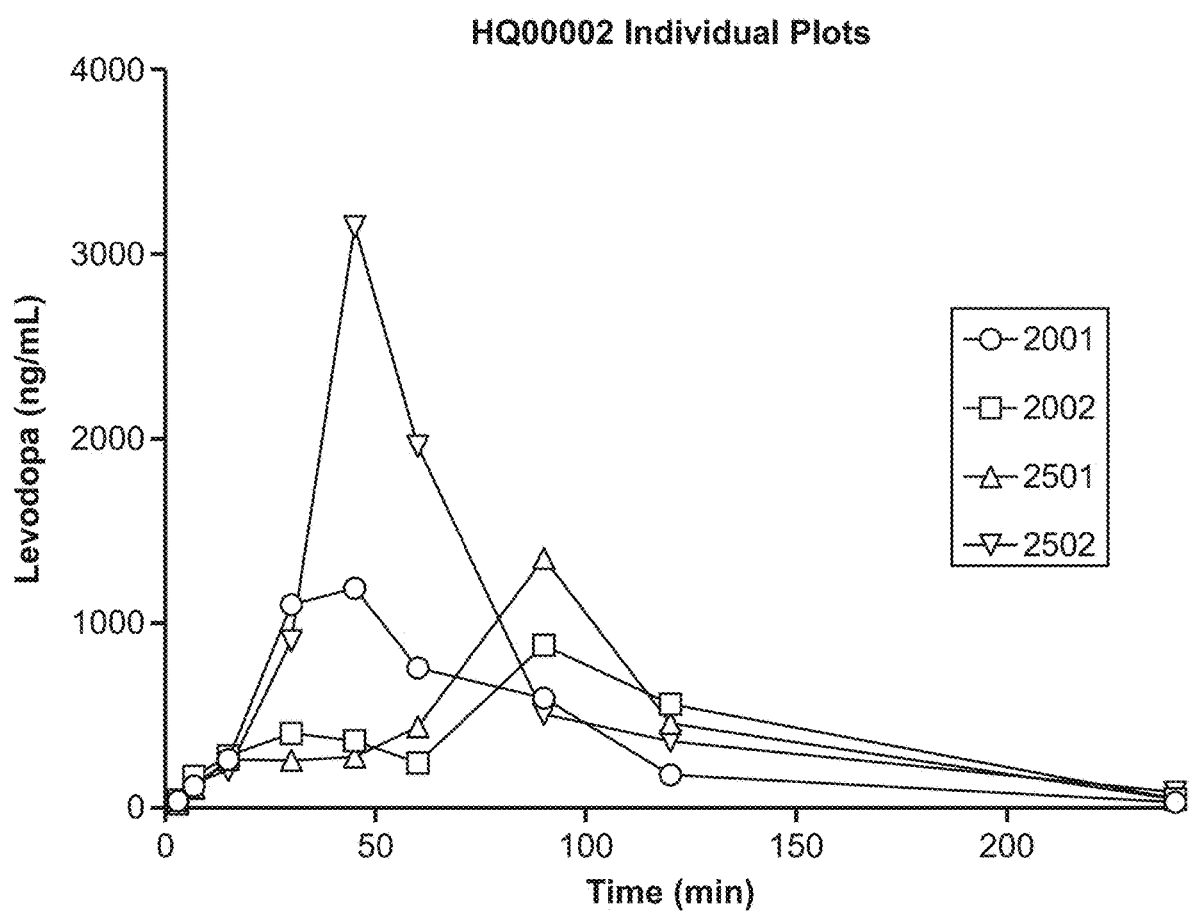
Figure 5C:
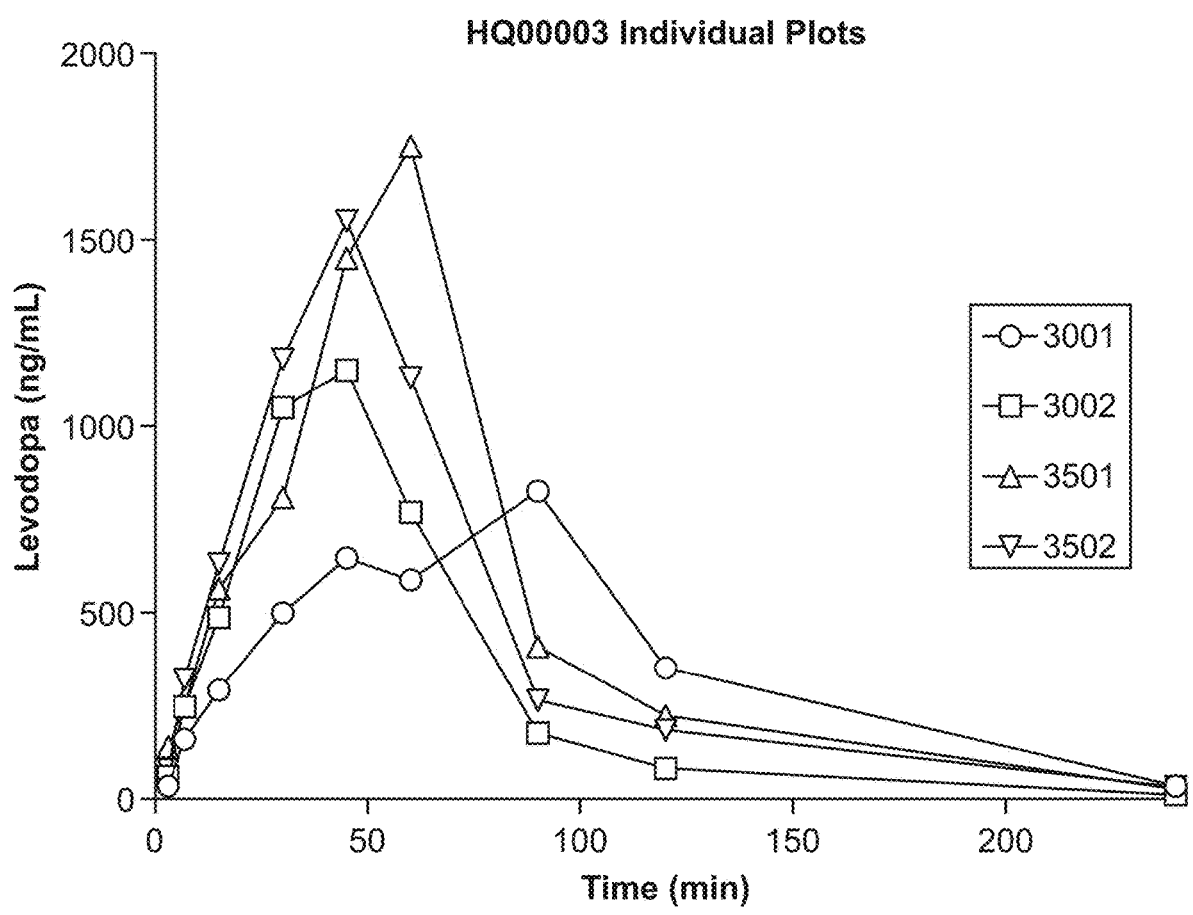
Figure 5D:
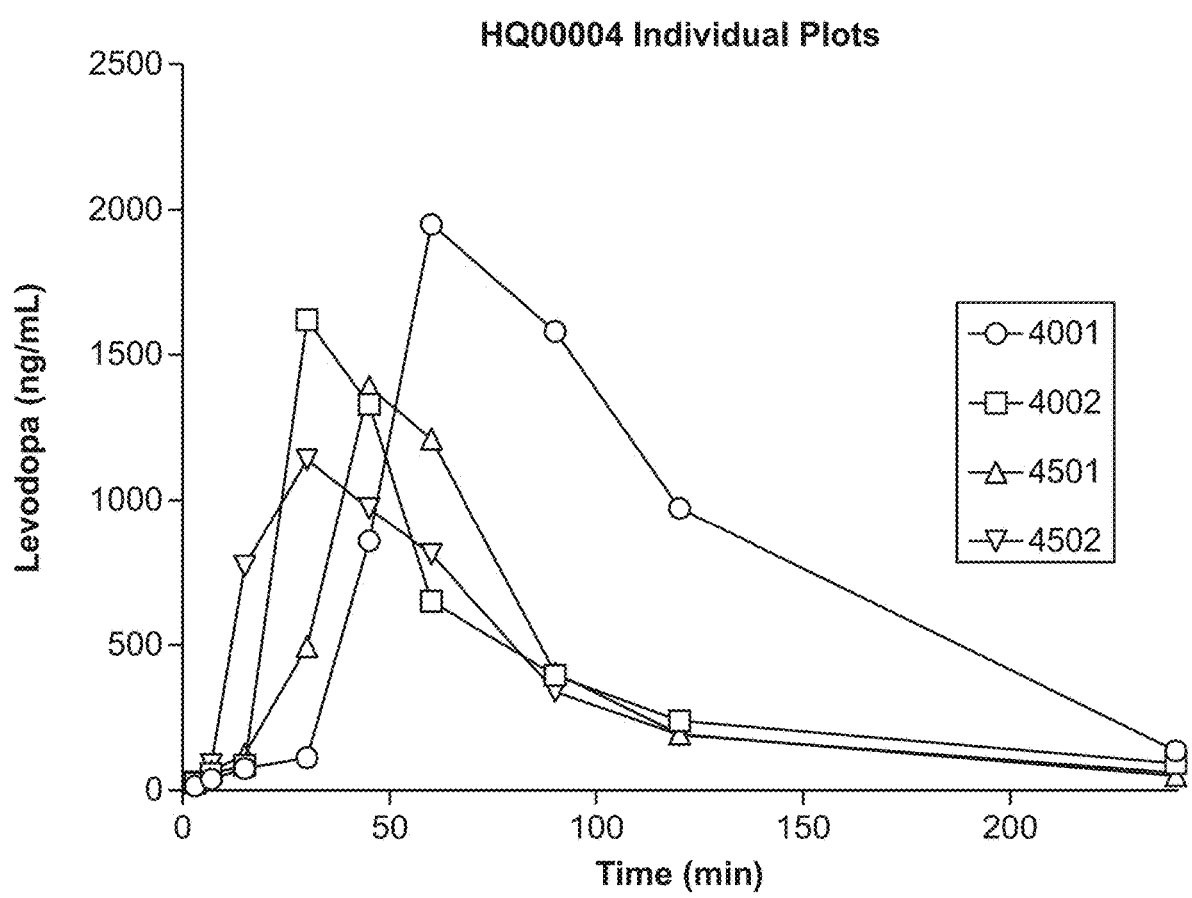
Figure 5E:
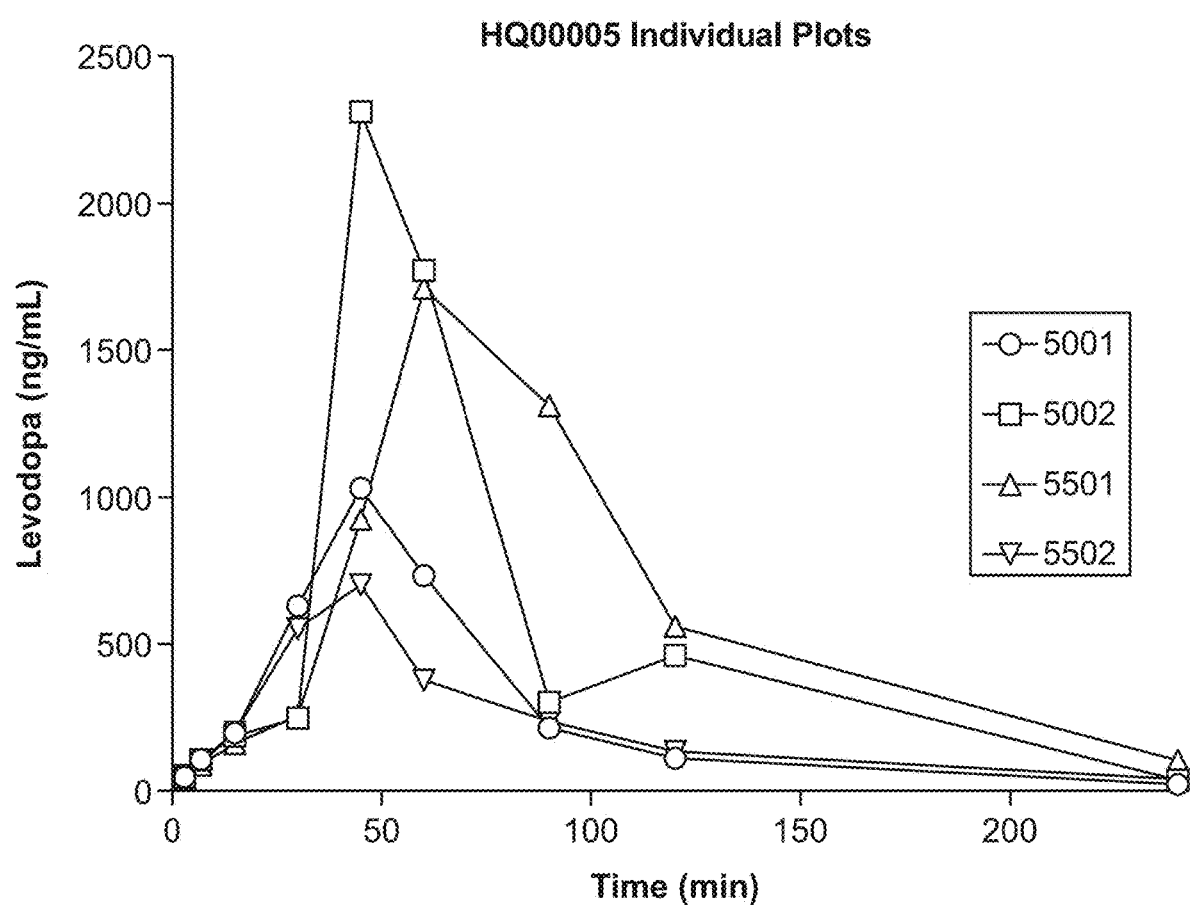

Results are displayed in Table 9 and FIGS. 3A-3C. All formulations tested achieved similar or up to 1.7-fold greater total exposure (AUC) and increased $C_{max}$, up to 2.3-fold, compared to the spray dried formulations tested in the second PK study (study 2037-004, described above). The measured $T_{max}$ values for the groups containing L-DOPA and HPMC/DSPC all had similar or greater values compared to the formulations tested in the previous study.

Surprisingly, however, the $T_{max}$ for the maltoside formulation (Group 4) was significantly shorter, with the median $T_{max}$ observed at 30 min, and all 4 monkeys in this group achieved plasma L-DOPA concentrations >400 ng/mL within 7 minutes following L-DOPA administration by the nhpPOD Device. As one of the goals of this product is to achieve plasma concentrations of L-DOPA>200-400 ng/mL very quickly to switch a patient from 'off' to 'on', the formulation containing maltoside was selected for testing in the human clinical trial described in Example 3 below.

Furthermore, the combination formulation with L-DOPA and benserazide (Group 5) performed as well or better than the comparable L-DOPA alone formulation with oral benserazide pretreatment (Group 3). As provided in FIG. 3C and Table 9, the combination formulation achieved similar total exposure (AUC) and $C_{max}$, and shorter median $T_{max}$ in the absence of oral benserazide, compared to the comparable L-DOPA alone formulations with oral benserazide. The data suggest that the combination formulation can treat Parkinson's disease, including OFF episodes, independent of oral administration of DDI.

TABLE 9

Mean (±SD) PK Parameters for L-DOPA Following Intranasal Administration in the Monkey (n = 4/group) with Pre-treatment with Oral Benserazide (4 × 5 mg capsule over 24 hours for Groups 1-4)

| Group | Dose/Formulation | $AUC_{last}$ (ng · min/mL) | $C_{max}$ (ng/mL) | Median $T_{max}$ (minute) | $t_{1/2}$ (minute) |
|---|---|---|---|---|---|
| 1 | L-DOPA:NaCl:HPMC:DSPC (68:2:16:14) | 150440 ± 80177 | 2395 ± 1129 | 75 | 231 ± 48 |
| 2 | L-DOPA:NaCl:HPMC:DSPC (68:2:23:7) | 136449 ± 11181 | 1810 ± 1031 | 105 | 139 ± 39 |
| 3 | L-DOPA:NaCl:HPMC:DSPC (68:2:23:7) | 98999 ± 35043 | 1817 ± 863 | 60 | 165 ± 51 |
| 4 | L-DOPA:NaCl:HPMC:maltoside (68:2:23:7) | 127059 ± 67663 | 1880 ± 844 | 30 | 49 ± 23 |
| 5 | L-DOPA:NaCl:Benserazide:HPMC:DSPC (68:2:7:16:7) | 95692 ± 19543 | 1727 ± 912 | 53 | 162 ± 77 |

Abbreviations:
DSPC, 1,2-distearoyl-sn-glycero-3-phosphocholine;
HPMC, hydroxypropyl methyl cellulose;
NaCl, sodium chloride;
maltoside, n-dodecyl-β-D-maltopyranoside 5.6.1.4. Single Dose Intranasal Pharmacokinetic Study in the Cynomolgus Monkey (Non-GLP, Research Study Number 2037-007)

A fourth single dose PK study was performed in the cynomolgus monkey, where L-DOPA dry powder (spray dried) formulations were administered intranasally using an nhpPOD Device. Ten male and ten female monkeys were assigned to five groups. Each group was administered a different spray dried formulation of L-DOPA, according to the design outlined in Table 10. Each animal was pretreated with oral benserazide (size 3 capsule) such that each animal in Groups 1-5 received a 5 mg oral dose at 24, 16, 8 and 0.75 hr prior to being dosed intranasally with L-DOPA.

Blood samples (1.6 mL stabilized with sodium metabisulfite) were collected from fasted animals pre-dose, 3, 7, 15, 30, 45, 60, 90, 120, 240, 360 and 600 minutes after dosing from animals in all groups. Plasma was isolated from whole blood and samples were frozen prior to analysis by AIT Bioscience, Indiana, USA. Non-compartmental PK analysis was performed on an individual animal basis.

TABLE 10

Study Design (study 2037-007)

| Group | Test Article | | Number of animals (M/F) | Target Total Dose (mg) | Dose Regimen |
|---|---|---|---|---|---|
| 1 (FS-A-HQ00001) | L-DOPA:NaCl:HPMC:maltoside (68:2:29:1) | | 2/2 | 20 | 10 mg once to both nostrils |
| 2 (FS-B-HQ00002) | L-DOPA:NaCl:HPMC:maltoside (68:2:29:1) | | 2/2 | 20 | 10 mg once to both nostrils |

TABLE 10-continued

Study Design (study 2037-007)

| Group | Test Article | Number of animals (M/F) | Target Total Dose (mg) | Dose Regimen |
|---|---|---|---|---|
| 3 (FS-C-HQ00003) | L-DOPA:NaCl:HPMC:maltoside (68:2:29:1) | 2/2 | 20 | 10 mg once to both nostrils |
| 4 (FS-D-HQ00004) | L-DOPA:NaCl:HPMC:maltoside (68:2:29.9:0.1) | 2/2 | 20 | 10 mg once to both nostrils |
| 5 (FS-E-HQ00005) | L-DOPA:NaCl:HPMC:maltoside (68:2:29.5:0.5) | 2/2 | 20 | 10 mg once to both nostrils |

Abbreviations:
F, female;
HPMC, hydroxypropyl methyl cellulose;
M, male;
NaCl, sodium chloride;
maltoside, n-dodecyl-β-D-maltopyranoside (DDM)

Results are displayed in Table 11 and FIGS. 4A-C and FIGS. 5A-E. All the tested formulations achieved total exposure (AUC), $C_{max}$ and $T_{max}$ values similar to the spray dried formulations tested in the third PK study (study 2037-006, described above) as provided in FIGS. 4A-4C. These formulations have similar or up to 1.7-fold greater total exposure (AUC) and increased $C_{max}$, up to 2.3-fold, compared to the spray dried formulations tested in the second PK study (study 2037-004, described above). Although the third PK study demonstrated that the $T_{max}$ for the formulation including 7% maltoside is significantly shorter than the $T_{max}$ for the formulation including DSPC instead of maltoside, $T_{max}$ values for the formulations including different concentrations (0.1, 0.5, 1%) of maltoside were not significantly different from each other.

TABLE 11

Mean (±SD) PK Parameters for L-DOPA Following Intranasal Administration in the Monkey (n = 4/group) and Pre-treatment with Oral Benserazide (4 × 5 mg capsule over 24 hours for Groups 1-5)

| Group (formulation batch) | Dose/Formulation | $AUC_{last}$ (ng · min/mL) | $C_{max}$ (ng/mL) | Median $T_{max}$ (minute) [min, max] | $t_{1/2}$ (minute) |
|---|---|---|---|---|---|
| 1 (FS-A-HQ00001) | L-DOPA:NaCl:HPMC:maltoside (68:2:29:1) | 110,786 ± 30,681 | 1840 ± 434 | 45 [15, 45] | 98 ± 42 |
| 2 (FS-B-HQ00002) | L-DOPA:NaCl:HPMC:maltoside (68:2:29:1) | 113,551 ± 33,367 | 1643 ± 1024 | 68 [45, 90] | 55 ± 12 |
| 3 (FS-C-HQ00003) | L-DOPA:NaCl:HPMC:maltoside (68:2:29:1) | 92,404 ± 18,094 | 1310 ± 413 | 53 [45, 90] | 42 ± 6 |
| 4 (FS-D-HQ00004) | L-DOPA:NaCl:HPMC:maltoside (68:2:29.9:0.1) | 125,947 ± 53,361 | 1525 ± 345 | 37.5 [30, 60] | 106 ± 50 |
| 5 (FS-E-HQ00005) | L-DOPA:NaCl:HPMC:maltoside (68:2:29.5:0.5) | 101,243 ± 52,699 | 1438 ± 717 | 45 [45, 60] | 80 ± 39 |

Abbreviations:
F, female;
HPMC, hydroxypropyl methyl cellulose;
M, male;
NaCl, sodium chloride;
maltoside, n-dodecyl-β-D-maltopyranoside 5.6.1.5. Single Dose Intranasal Pharmacokinetic Study in the Cynomolgus Monkey (Non-GLP, Research Study Number 2037-017)

A fifth single dose PK study was performed in the cynomolgus monkey, where L-DOPA dry powder (spray dried) formulations were administered intranasally using an nhpPOD Device. Ten male and ten female monkeys were assigned to five groups. Each group was administered a different spray dried formulation of L-DOPA, according to the design outlined in Table 12. Animals in Group 1 were pretreated with oral benserazide (size 3 capsule) such that each animal in this group received a 5 mg dose 0.75 hr prior to being dosed intranasally with L-dopa. The L-DOPA drug formulations for Groups 2, 3, 4 and 5 had carbidopa co-administered nasally. The formulations for Groups 2-5 had either no permeation enhancer or a permeation enhancer (maltoside, EDTA or propylene glycol); however, all formulations had similar compositions.

Blood samples (1.6 mL stabilized with sodium metabisulfite) were collected from fasted animals pre-dose, 3, 7, 15, 30, 45, 60, 90, 120, 240, 360 and 600 minutes after dosing from animals in all groups. Plasma was isolated from whole blood and samples were frozen prior to analysis by AIT Bioscience, Indiana, USA. Non-compartmental PK analysis was performed on an individual animal basis.

TABLE 12

Study Design (study 2037-017)

| Group | Test Article | Number of animals (M/F) | Target Total Dose (mg) | Dose Regimen |
|---|---|---|---|---|
| 1 | Oral benserazide (5 mg) 0.75 hr prior to L-DOPA:NaCl:HPMC:maltoside (68:2:29:1) | 2/2 | 20 | 10 mg once to both nostrils |
| 2 | L-DOPA:Carbidopa:NaCl:HPMC:maltoside (68:6.8:2:22.2:1) | 2/2 | 20 | 10 mg once to both nostrils |
| 3 | L-DOPA:Carbidopa:NaCl:HPMC (68:6.8:2:23.2:1) | 2/2 | 20 | 10 mg once to both nostrils |
| 4 | L-DOPA:Carbidopa:NaCl:HPMC:EDTA (68:6.8:2:22.7:0.5) | 2/2 | 20 | 10 mg once to both nostrils |
| 5 | L-DOPA:Carbidopa:NaCl:HPMC:propylene glycol (68:6.8:2:22.2:1) | 2/2 | 20 | 10 mg once to both nostrils |

Abbreviations:
F, female;
HPMC, hydroxypropyl methyl cellulose;
M, male;
NaCl, sodium chloride;
maltoside, n-dodecyl-β-D-maltopyranoside (DDM);
EDTA, ethylenediaminetetraacetic acid Results are displayed in Table 13 and FIG. 10. All formulations tested achieved similar total exposure (AUC$_{last}$), C$_{max}$ and T$_{max}$ compared to the spray dried formulations tested in the previously described PK studies. The formulations with the greatest exposure (AUC$_{last}$) and highest plasma concentration (C$_{max}$) were the spray dried L-DOPA formulation paired with oral benserazide delivered 0.75 hr before intranasal L-DOPA and the spray dried L-DOPA with carbidopa formulation, supporting the hypothesis that nasally delivered carbidopa may provide adequate AADC inhibition, similar to orally delivered benserazide administered before nasally delivered L-DOPA. In addition to the comparison of orally and nasally delivered DDI, the permeation enhancers maltoside, EDTA, and propylene glycol were compared in formulations containing L-DOPA with carbidopa. The formulation resulting in the fastest T$_{max}$ (38 min) was the formulation containing propylene glycol as the permeation enhancer. An important aspect to consider when selecting formulation for the indication of reversal of OFF episode in PD is the time to achieve plasma levels of >200-400 ng/mL, at which level it has been reported that PD patients experience a pharmacodynamic response and switch to ON. Considering this parameter, the formulation to achieve >200-400 ng/mL in the shortest amount of time (on average) was the spray dried L-DOPA with carbidopa formulation with maltoside as the permeation enhancer (FIG. 10; green line with rectangles). As such, the results from this study led to the sixth NHP PK study (Study 2037-019) to examine the effect of co-administration of L-DOPA with carbidopa assessed at different ratios of L-DOPA to carbidopa with maltoside as the permeation enhancer.

TABLE 13

Mean (±SD) PK Parameters for L-DOPA Following Intranasal Administration in the Monkey (n = 4/group) with either Pre-treatment with Oral Benserazide (5 mg 0.75 hr prior to intranasal L-DOPA for Group 1) or Co-Administration of Carbidopa by Intranasal Administration (study 2037-017)

| Group (formulation batch) | Dose/Formulation | AUC$_{last}$ (ng · min/mL) | C$_{max}$ (ng/mL) | Median T$_{max}$ (minute) | t$_{1/2}$ (minute) |
|---|---|---|---|---|---|
| 1 | Oral benserazide (5 mg) 0.75 hr prior to L-DOPA:NaCl:HPMC:maltoside (68:2:29:1) | 161,681 ± 40,269 | 1,582 ± 905 | 53 | 146 ± 36 |
| 2 | L-DOPA:Carbidopa:NaCl:HPMC:maltoside (68:6.8:2:22.2:1) | 149,941 ± 22,112 | 1,608 ± 198 | 53 | 129 ± 74 |
| 3 | L-DOPA:Carbidopa:NaCl:HPMC (68:6.8:2:23.2:1) | 75,838 ± 19,589 | 560 ± 385 | 68 | 313 ± 136 |
| 4 | L-DOPA:Carbidopa:NaCl:HPMC:EDTA (68:6.8:2:22.7:0.5) | 115,917 ± 40,681 | 1,469 ± 587 | 60 | 165 ± 80 |

TABLE 13-continued

Mean (±SD) PK Parameters for L-DOPA Following Intranasal Administration in the Monkey (n = 4/group) with either Pre-treatment with Oral Benserazide (5 mg 0.75 hr prior to intranasal L-DOPA for Group 1) or Co-Administration of Carbidopa by Intranasal Administration (study 2037-017)

| Group (formulation batch) | Dose/Formulation | $AUC_{last}$ (ng · min/mL) | $C_{max}$ (ng/mL) | Median $T_{max}$ (minute) | $t_{1/2}$ (minute) |
|---|---|---|---|---|---|
| 5 | L-DOPA:Carbidopa:NaCl:HPMC:propylene glycol (68:6.8:2:22.2:1) | 97,402 ± 32,065 | 960 ± 500 | 38 | 92 ± 47 |

Abbreviations:
F, female;
HPMC, hydroxypropyl methyl cellulose;
M, male;
NaCl, sodium chloride;
maltoside, n-dodecyl-β-D-maltopyranoside;
EDTA, ethylenediaminetetraacetic acid 5.6.1.6. Single Dose Intranasal Pharmacokinetic Study in the Cynomolgus Monkey (Non-GLP, Research Study Number 2037-019)

A sixth single dose PK study was performed in the cynomolgus monkey, where L-DOPA dry powder formulations (spray dried formulations with carbidopa) were administered intranasally using a nhpPOD device. Two male and two female monkeys were each assigned to five groups. Each group was administered a spray dried formulation of L-DOPA (Group 1) or L-DOPA with carbidopa (Groups 2-5) according to the design outlined in Table 14. In Group 1, each animal was pretreated with oral benserazide (size 3 capsule) such that each animal received a 5 mg dose at 0.75 hr prior to being dosed intranasally with L-DOPA. L-DOPA drug formulations for Group 2 had carbidopa spray dried in the formulation and both the L-DOPA and the carbidopa were substantially amorphous, and Groups 3, 4 and 5 were manufactured by blending the spray dried L-DOPA formulation with GMP carbidopa monohydrate (Teva) at 10:1 and approximate, 20:1 and 4:1 ratio of L-DOPA:carbidopa. In Groups 3, 4, and 5 the L-DOPA was substantially amorphous and the carbidopa was crystalline. The formulation used in Group 3 was the representative formulation for proposed clinical trial Cohort 4. For Group 1, the DDI benserazide was delivered orally. For Groups 2-5, the DDI carbidopa was delivered intranasally with L-DOPA.

Blood samples (1.6 mL stabilized with sodium metabisulfite) were collected from fasted animals pre-dose, 3, 7, 15, 30, 45, 60, 90, 120, 240, 360 and 600 minutes after dosing from animals in all groups. Plasma was isolated from whole blood and samples were frozen prior to analysis by AIT Bioscience, Indiana, USA. Non-compartmental PK analysis was performed on an individual animal basis.

TABLE 14

Study Design (study 2037-019)

| Group | Test Article | Number of animals (M/F) | Target Total Dose (mg) | Dose Regimen |
|---|---|---|---|---|
| 1 (BG58-154) | Oral benserazide (5 mg) 0.75 hr prior to L-DOPA:NaCl:HPMC:maltoside (68:2:29:1) | 2/2 | 20 | 10 mg once to both nostrils |
| 2 (BG58-152) | L-DOPA:Carbidopa:NaCl:HPMC:maltoside (68:6.8:2:22.2:1) | 2/2 | 20 | 10 mg once to both nostrils |
| 3 (BG58-156) | L-DOPA:Carbidopa:NaCl:HPMC:maltoside (63.4:6.8:1.9:27:0.9) | 2/2 | 20 | 10 mg once to both nostrils |
| 4 (BG58-157) | L-DOPA:Carbidopa:NaCl:HPMC:maltoside (65.6:3.5:1.9:28:1) | 2/2 | 20 | 10 mg once to both nostrils |
| 5 (BG58-158) | L-DOPA:Carbidopa:NaCl:HPMC:maltoside (57.5:15.5:1.7:24.5:0.8) | 2/2 | 20 | 10 mg once to both nostrils |

Abbreviations:
F, female;
HPMC, hydroxypropyl methyl cellulose;
M, male;
NaCl, sodium chloride;
maltoside, n-dodecyl-β-D-maltopyranoside (DDM)

Results are displayed in Table 15 and FIG. 11. All formulations tested achieved similar total exposure (AUC$_{last}$), C$_{max}$ and T$_{max}$ compared to the spray dried formulations tested in the previously described PK studies. Delivery of four of the five formulations tested in this study resulted in similar exposure (AUC$_{last}$), including L-DOPA with oral benserazide (Group 1), a spray dried formulation of L-DOPA with carbidopa at a 10:1 ratio (Group 2), and a spray dried L-DOPA formulation blended with GMP carbidopa at a ratio of approximately 10:1 (Group 3) or a ratio of approximately 4:1 (Group 5). Similarly, the measured C$_{max}$ values were highest for Group 1 (spray dried L-DOPA delivered intranasally with oral benserazide) and similar for Group 3 (spray dried L-DOPA:carbidopa at 10:1 delivered intranasally) and Group 5 (spray dried L-DOPA:carbidopa at 4:1 delivered intranasally). These results support the hypothesis that nasally delivered carbidopa may provide adequate dopa decarboxylase inhibition, similar to oral benserazide administered 0.75 hr before nasally delivered L-DOPA. Additionally, due to the similarities in pharmacokinetic uptake, this study supports that amorphous L-DOPA can be co-formulated with either amorphous carbidopa or crystalline carbidopa and similar results can be expected.

An important aspect to consider when selecting a formulation for the treatment of OFF episodes in PD is the time to achieve plasma levels of >200-400 ng/mL, where it has been reported that PD patients experience a pharmacodynamic response and switch to ON. Considering this parameter, the formulation to achieve >200-400 ng/mL in the shortest amount of time (on average) was the formulation tested in Group 3, a spray dried L-DOPA formulation blended with carbidopa (~10:1 ratio of L-dopa:carbidopa) and with the same excipients as are currently being used in the L-DOPA only formulation being used in the clinical trial INP103-201 for dosing in cohorts 1, 2 and 3. As such, the results from this study guided the selection of a clinical formulation of spray dried L-DOPA (with excipients) blended with carbidopa at a ratio of 10:1 L-dopa:carbidopa for dosing in clinical Cohort 4 (see Example 3).

TABLE 15

Mean (±SD) PK Parameters for L-DOPA Following Intranasal Administration in the Monkey (n = 4/group) with either Pre-treatment with Oral Benserazide (5 mg 0.75 hr prior to intranasal L-DOPA for Group 1) or Co-Administration of Carbidopa by Intranasal Administration (study 2037-019)

| Group (formulation batch) | Dose/Formulation | AUC$_{last}$ (ng · min/mL) | C$_{max}$ (ng/mL) | Median T$_{max}$ (minute) | t$_{1/2}$ (hr) |
|---|---|---|---|---|---|
| 1 (BG58-154) | Oral benserazide (5 mg) 0.75 hr prior to L-DOPA:NaCl:HPMC:maltoside (68:2:29:1) | 1760 ± 499 | 1659 ± 827 | 53 | 1.3 ± 0.7 |
| 2 (BG58-152) | L-DOPA:Carbidopa:NaCl:HPMC:maltoside (68:6.8:2:22.2:1) | 1932 ± 406 | 959 ± 296 | 90 | 0.9 ± 0.2 |
| 3 (BG58-156) | L-DOPA:Carbidopa:NaCl:HPMC:maltoside (63.4:6.8:1.9:27:0.9) | 1896 ± 805 | 1259 ± 392 | 45 | 0.8 ± 0.2 |
| 4 (BG58-157) | L-DOPA:Carbidopa:NaCl:HPMC:maltoside (65.6:3.5:1.9:28:1) | 1392 ± 493 | 838 ± 256 | 60 | 1.7 ± 0.8 |
| 5 (BG58-158) | L-DOPA:Carbidopa:NaCl:HPMC:maltoside (57.5:15.5:1.7:24.5:0.8) | 2071 ± 209 | 1395 ± 325 | 53 | 0.8 ± 0.2 |

Abbreviations:

F, female;

HPMC, hydroxypropyl methyl cellulose;

M, male;

NaCl, sodium chloride;

maltoside, n-dodecyl-β-D-maltopyranoside

5.6.1.7. Materials and Methods

Materials and methods for the studies described above are described here.

5.6.1.7.1. Summary

TABLE 16

| | |
|---|---|
| Nasal Administration Device: | Part Name: nhpPOD Device (POD Device, NHP, Powder, study 2037-003, 2037-004, 2037-006, 2037-007) Study #2037-003: Part Number: 00308-01 Description: powder delivery using the nhpPOD with reducer and extension tube Study #2037-004: Part Number: 00308-02 Description: powder delivery using the nhpPOD with optimized reducer and extension tube Study #2037-006: Part Number: 00308-02 Description: powder delivery using the nhpPOD with optimized reducer and extension tube Study #2037-007: Part Number: 00308-02 Description: powder delivery using the nhpPOD with optimized reducer and extension tube Study #2037-017: Part Number: 00308-02 Description: powder delivery using the nhpPOD with optimized reducer and extension tube Study #2037-019: Part Number: 00308-02 Description: powder delivery using the nhpPOD with optimized reducer and extension tube |
| Preparation Details: | The control and test articles were received from the Sponsor, and loaded into the powder nhpPOD (powder non-human primate Precision Olfactory Delivery) Device tip on the day of dosing. The nhpPOD Device tip was tapped on the powder, Levodopa formulation test article or control, to load 10 mg of powder into each device tip and excess powder was wiped from the tip using a Kimwipe. Standard laboratory procedures were used and no problems were encountered. |
| Dose Administration Details: | Animals were dosed awake while being held in the prone position with the head in a neutral position and sight line parallel to the ground (horizontal plane). |

5.6.1.7.2. nhpPOD Devices

The nhpPOD device described in section 5.5.3.4 and FIGS. 9A-9E was used to conduct the studies in Table 16 above.

5.6.1.7.3. Methods

Bioanalysis of NHP Plasma Samples for Levodopa

A non-GLP bioanalytical method was developed for analysis of levodopa in NHP plasma at AIT Bioscience (Indianapolis, Ind., USA). This method was based on a validated method for the quantitation of levodopa in rat plasma, previously developed and validated at AIT Bioscience for Impel.

Preparation of Plasma Samples for Analysis of Levodopa

Sodium metabisulfite (4% by volume of a 100 mg/mL solution in sterile water) was added as stabilizer (e.g. 10.4 µL of the 100 mg/mL sodium metabisulfite solution was added to 250 µL of blood) within a few minutes after each blood collection followed by thorough, gentle mixing by inversion prior to being placed on wet ice. The tubes were kept protected from light (i.e. in a closed cooler and/or covered with aluminum foil) and generally centrifuged within 15 minutes of collection. Samples were centrifuged under refrigeration (set to +4° C. and 1500 g RCF) for targeted 10 minutes. Plasma was recovered, transferred using a micropipette into separate tubes and placed on dry ice, pending storage in a freezer set to maintain −70° C. until shipment.

Preparation of Calibration Standards and Quality Control Samples

Stock solutions of levodopa were prepared to 2.00 mg/mL in 0.1N perchloric acid and stored in amber glass at 2-8° C.

$K_2$EDTA fortified NHP plasma was prepared by mixing 100 mg/mL aqueous sodium metabisulfite with NHP plasma in a 4:96 ratio.

Calibration Standard (CS) spiking solutions (100,000 ng/mL to 200 ng/mL) were prepared by dilution of a stock solution with 100 mg/mL sodium metabisulfite solution. CS were then prepared by diluting these spiking solutions with $K_2$EDTA fortified NHP plasma in a 5:95 ratio to achieve nominal concentrations of 5,000 to 10.0 ng/mL, in 8 levels.

QC spiking solutions were similarly prepared by dilution of a separate stock solution with 100 mg/mL sodium metabisulfite solution. QC were then prepared by diluting these spiking solutions with $K_2$EDTA fortified NHP plasma in a 5:95 ratio to achieve nominal concentrations of 3,750, 300, 30, and 10.0 ng/mL.

CS and QC pools were prepared and sub-divided into single-use aliquots stored in polypropylene vials at −80° C. Aliquots of the CS and QC pools were thawed for one-time use on wet ice.

A sample volume of 50.0 µL was aliquoted into a 1.2 mL 96-well plate and mixed with 25.0 µL internal standard solution (2000 ng/mL L-DOPA-2,5,6-D3 in 2N perchloric acid). Then, 125 µL of water was added to each well. The plates were covered and the mixtures were vigorously shaken, vortexed to mix, and centrifuged. Using a Tomtec Quadra96 liquid handler, a 100 µL aliquot of the supernatant was transferred to a clean 96-well plate for LC-MS/MS injection.

Samples were analyzed on a Waters Acquity liquid chromatograph interfaced with a Thermo Scientific TSQ Vantage triple quadrupole mass spectrometer with ESI ionization. Each extracted sample was injected (10.0 µL) onto an Acquity HSS C18 column (2.1×50.0 mm; 1.8 µm) equilibrated at 30° C. Mobile Phase A was 100-0.1 water-formic acid. Mobile Phase B was 100-0.1 acetonitrile-formic acid. The LC gradient is tabulated in Table 17 below.

TABLE 17

| Time (min) | Flow Rate (mL/min) | Mobile Phase A (%) | Mobile Phase B (%) |
|---|---|---|---|
| 0.00 | 0.500 | 100.0 | 0.0 |
| 1.00 | 0.500 | 95.0 | 5.0 |
| 1.70 | 0.500 | 88.0 | 12.0 |
| 2.00 | 0.500 | 88.0 | 12.0 |
| 2.25 | 0.500 | 30.0 | 70.0 |
| 3.25 | 0.500 | 30.0 | 70.0 |
| 3.50 | 0.500 | 100.0 | 0.0 |
| 6.00 | 0.500 | 100.0 | 0.0 |

The retention time, mass transition and precursor charge state for each compound are as follows:

TABLE 18

| Compound | Expected Retention Time (min) | Precursor Mass/Charge (m/z) | Product Observed Mass/Charge (m/z) | Charge State of Precursor Ion |
|---|---|---|---|---|
| Levodopa | 0.68 | 198.127 | 152.071 | +1 |
| Levodopa-2,5,6-D3 | 0.68 | 201.141 | 154.096 | +1 |

Peak area ratios from the calibration standard responses were regressed using a (1/concentration$^2$) linear fit for levodopa. The regression model was chosen based upon the behavior of the analyte across the concentration range used during method development.

Pharmacokinetic Parameter Calculations and Data Analysis

Plasma concentration-time data for levodopa was used to determine pharmacokinetic (PK) parameters. Non-compartmental analysis (NCA) was performed on the individual subject plasma concentration data using the software Phoenix WinNonlin (v6.3 or 8).

The following pharmacokinetic parameters were determined: $C_{max}$, $T_{max}$, $T_{last}$, $AUC_{last}$, and $t_{1/2}$ where possible. Various additional pharmacokinetic parameters were automatically generated by Phoenix WinNonlin software but were not presented. The following configuration was used for the analysis:

Model type selection (Plasma 200-202) was based on the biological matrix (plasma) and the dose type was based on the route of administration (extravascular). Observed parameters were used for the analysis. The acceptance criteria for Kei determination were regression of at least three time points in the apparent terminal elimination phase, excluding $C_{max}$, otherwise $t_{1/2}$ was not determined or reported. Nominal blood sampling times and nominal dose levels were used. Concentrations reported as below the lower limit of quantification were treated as zero (0).

5.6.2. Example 2: Rodent PK Study 5.6.2.1. Single Dose Intranasal Pharmacokinetic Study in the Rat (Research Study Number PBI-18-057)

A single dose PK study was performed with Sprague-Dawley Rats (with 226-250 g body weight), where L-DOPA dry powder (spray dried) formulations were administered intranasally using an Impel rat Precision Olfactory Delivery Device ("rPOD") with or without benserazide pre-treatment. The rPOD used in this experiment is an intranasal delivery device for a rat described in U.S. Pat. Pub. No. 2015/0100042, incorporated herein by reference in its entirety. Twenty male rats were assigned to five groups. Each group was administered a different spray dried formulation of L-DOPA, according to the design outlined in Table 19.

Each animal in Groups 1-4 was pretreated with 3 mg/kg of oral benserazide 0.5 hr prior to dosing intranasally with a formulation containing L-DOPA (t=-0.5 hr). Animals in Group 5 were not pretreated with oral benserazide; instead, the intranasal formulation included both levodopa and the DDI, carbidopa.

Approximately 5 minutes prior to intranasal administration, animals were anesthetized with isoflurane anesthesia on a nosecone and the rPOD Device was prepared with relevant test article. After intranasal administration (t=0), the animals were allowed to recover from anesthesia under normal conditions, and housed by treatment group in bedded, static micro-isolator cages.

Blood samples (350 µL) were collected from the tail vein 5, 15, 30, 60, 120, and 240 minutes after intranasal administration from animals in all groups. Whole blood was collected into $K_2EDTA$ tubes (BD #365974) preloaded with 14 µL of 100 mg/ml Sodium Metabisulfite solution (Fisher #S244, prepared in Di $H_2O$). Blood samples were maintained on ice and centrifuged at 4° C. within one hour of collection for the production of plasma (yielding about 140 µL plasma/timepoint), snap frozen in 96-well plates and stored at -80° C. until shipped to Pxyant Labs on dry ice for subsequent bioanalysis.

TABLE 19

Study Design (study PBI-18-057)

| Group | Number of animals | Pretreatment | Test Article | Target Total Dose (mg) | Dose Regimen |
|---|---|---|---|---|---|
| 1 | 4 | 3 mg/kg Benserazide (at t = -0.5 h) | BG54-54 L-DOPA:Hydroxy B-Cyclodextrin:maltoside:NaCl (68:29:1:2) | 2.5 | 2.5 mg once to right nostril (at t = 0 h) |
| 2 | 4 | 3 mg/kg Benserazide (at t = -0.5 h) | BG54-89 L-DOPA:Soluplus ®:maltoside:NaCl (68:29:1:2) | 2.5 | 2.5 mg once to right nostril (at t = 0 h) |
| 3 | 4 | 3 mg/kg Benserazide (at t = -0.5 h) | BG54-91 L-DOPA:Kollidon ® VA64:maltoside:NaCl (68:29:1:2) | 2.5 | 2.5 mg once to right nostril (at t = 0 h) |
| 4 | 4 | 3 mg/kg Benserazide (at t = -0.5 h) | HQ00001 L-DOPA:HPMC:maltoside:NaCl (68:29:1:2) | 2.5 | 2.5 mg once to right nostril (at t = 0 h) |
| 5 | 4 | Vehicle (at t = -0.5 h) | BG54-126 L-DOPA:Carbidopa:HPMC E5:maltoside:NaCl (68:6.8:22.2:1:2) | 2.5 | 2.5 mg once to right nostril (at t = 0 h) |

Figure 6:
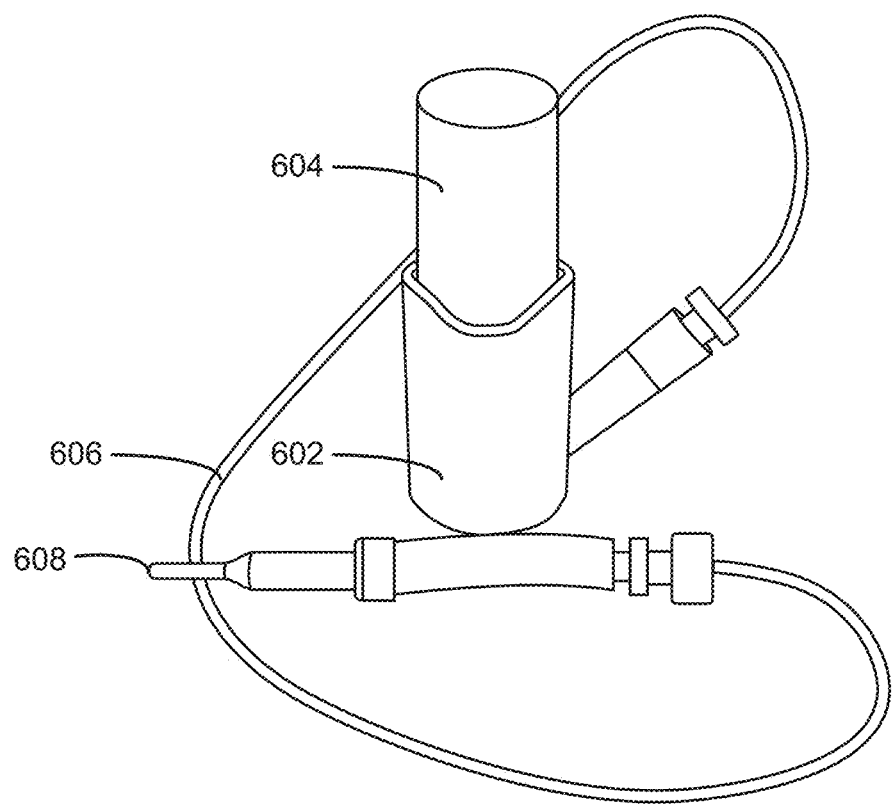

Abbreviations:
Soluplus ®, polyvinyl caprolactam-polyvinyl acetate-polyethylene glycol graft copolymer (PCL-PVAc-PEG));
HPMC, hydroxypropyl methyl cellulose;
Kollidon ® VA64, a vinylpyrrolidone-vinyl acetate copolymer;
NaCl, sodium chloride;
maltoside, n-dodecyl-β-D-maltopyranoside The average plasma concentration-time curves are displayed in FIG. 6. It shows that Group 5 treated with BG54-126 formulation in the absence of oral benserazide showed total exposure (AUC), $C_{max}$ and $T_{max}$ values similar or better than Group 4 treated with the HQ00001 formulation in the presence of oral benserazide. BG54-126 and HQ00001 contain similar compositions except that BG54-126 has carbidopa integrated into the nasal formulation whereas HQ00001 does not. Thus, these results demonstrate that the formulation containing both L-DOPA and DDI (e.g., BG54-126) can result in comparable if not superior plasma uptake and absorption compared to intranasal levodopa-alone treatment combined with oral DDI. These data further suggest that DDIs delivered via the respiratory tract can inhibit degradation of L-DOPA quickly enough to enable rapid update and absorption of L-DOPA into the plasma.

5.6.2.2. Single Dose Intranasal Pharmacokinetic Study in the Rat (Research Study Number PBI-19-056)

A single dose PK study was performed with male Sprague-Dawley Rats (with 226-250 g body weight), where L-DOPA dry powder (spray dried) formulations were administered via one of three routes: intranasally (i.n.) using an Impel rat Precision Olfactory Delivery Device ("rPOD"), intratracheally (i.t.) using an Impel IT Device to deliver the formulations to the lung, or via oral gavage (p.o.). The rPOD used in this experiment is an intranasal delivery device for a rat described in U.S. Pat. Pub. No. 2015/0100042, incorporated herein by reference in its entirety. Each group was administered a spray dried formulation of L-DOPA, according to the design outlined in Table 20.

For intranasal administration to animals in Group 1 and 2, rats were anesthetized with isoflurane anesthesia on a nosecone approximately 5 minutes prior to dosing, and the Impel rPOD Device was prepared. At t=0, test articles were administered via the Impel rPOD Device and the rats were allowed to recover from anesthesia under normal conditions and housed by treatment group in bedded, static micro-isolator cages. Each animal in Group 1 was administered with 5 mg of BG59-140, a formulation containing both L-DOPA and carbidopa intranasally (R. naris) once (t=0). Each animal in Group 2 were administered with 5 mg of GB59-141, a formulation containing L-DOPA intranasally (R. naris) once (t=0).

For intratracheal administration (IT) to animals in Groups 3 and 4, animals were induced to a surgical plane of anesthesia with isoflurane in an inducing chamber carried with 100% $O_2$ approximately 5 minutes prior to dosing. Rats then had a 16G orotracheal tube placed and interfaced with a positive pressure ventilator. Proper orotracheal tube placement was verified by observing chest wall movement in concert with the ventilator. At t=0, test articles were administered via an Impel IT Device and the orotracheal tube removed. Each animal in Group 3 were administered with 5 mg of BG59-140, a formulation containing both L-DOPA and carbidopa intratracheally (R. naris) once (t=0). Each animal in Group 4 were administered with 5 mg of GB59-141, a formulation containing L-DOPA intratracheally (R. naris) once (t=0). The rats were then allowed to recover from anesthesia under normal conditions and housed by treatment group in bedded, static micro-isolator cages.

For Group 5, test article was administered via oral gavage (PO) at a volume of 2 ml per rat. Specifically, each animal was administered with 5 mg of BG59-140, a formulation containing both L-DOPA and carbidopa once (t=0). After dosing, rats will be housed by treatment group in bedded, static micro-isolator cages.

Blood samples (350 µL) were collected from the tail vein 5, 15, 30, 60, 120, and 240 minutes after administration from animals in all groups. Whole blood was collected into $K_2EDTA$ tubes (BD #365974) preloaded with 14 µL of 100 mg/ml Sodium Metabisulfite solution (Fisher #S244, prepared in Di $H_2O$). Blood samples were maintained on ice and centrifuged at 4° C. within one hour of collection for the production of plasma (yielding about 140 µL plasma/timepoint), snap frozen in 96-well plates and stored at −80° C. until shipped to AIT BioScience on dry ice for subsequent bioanalysis.

TABLE 20

Study Design (study PBI-19-056)

| Group | Number of animals | Test Article | Target Total Dose (mg) | Dose Regimen | Sample Time |
|---|---|---|---|---|---|
| 1 | 4 | BG54-140 L-DOPA:Carbidopa | 3.3 | 5 mg once i.n. to right nostril (at t = 0 h) | 0 h, 0.083 h, 0.25 h, 0.5 h, 1 h, 2 h, 4 h |
| 2 | 4 | BG54-141 L-DOPA | 3.3 | 5 mg** once i.n. to right nostril (at t = 0 h) | 0 h, 0.083 h, 0.25 h, 0.5 h, 1 h, 2 h, 4 h |
| 3 | 4 | BG54-140 L-DOPA:Carbidopa | 3.3 | 5 mg** once i.t. (at t = 0 h) | 0 h, 0.083 h, 0.25 h, 0.5 h, 1 h, 2 h, 4 h |
| 4 | 4 | BG54-141 L-DOPA | 3.3 | 5 mg** once i.t. (at t = 0 h) | 0 h, 0.083 h, 0.25 h, 0.5 h, 1 h, 2 h, 4 h |

TABLE 20-continued

Study Design (study PBI-19-056)

| Group | Number of animals | Test Article | Target Total Dose (mg) | Dose Regimen | Sample Time |
|---|---|---|---|---|---|
| 5 | 4 | BG54-140* L-DOPA:Carbidopa | 3.3 | 5 mg** once p.o. (at t = 0 h) | 0 h, 0.083 h, 0.25 h, 0.5 h, 1 h, 2 h, 4 h |

Abbreviations:
Soluplus ®, polyvinyl caprolactam-polyvinyl acetate-polyethylene glycol graft copolymer (PCL-PVAc-PEG));
HPMC, hydroxypropyl methyl cellulose;
Kollidon ® VA64, a vinylpyrrolidone-vinyl acetate copolymer;
NaCl, sodium chloride;
maltoside, n-dodecyl-β-D-maltopyranoside;
*For oral administration, BG59-140 was delivered in the oral formulation vehicle (2% Heweten 102 Microcrystalline Cellulose in Di H2O). 1.67 mg/ml suspension was dosed at 2 ml per rat.
**Target dose of compound is 3.3 mg. Dose indicated above includes correction factor for formulation excipients and assay values.

The average plasma concentration-time curves are displayed in FIG. 12. The figure shows that Groups 1 and 3 treated with BG54-140 formulation containing both L-DOPA and carbidopa showed total exposure (AUC), $C_{max}$ and $T_{max}$ values similar or better than Groups 2 and 4 treated with BG54-141 without carbidopa, respectively. Thus, these results demonstrate that the formulation containing both L-DOPA and carbidopa (e.g., BG54-140) can result in comparable if not superior plasma uptake and absorption compared to L-DOPA-alone treatment when the formulations were delivered intranasally (i.n.) or intratracheally (i.t.). These further suggest that carbidopa delivered via the respiratory tract can inhibit degradation of L-DOPA quickly enough to enable rapid update and absorption of L-DOPA into the plasma.

5.6.3. Example 3: Phase IIa, Randomized, Double Blind, Placebo Controlled, Single Ascending Dose, Safety and Pharmacokinetic/Pharmacodynamic Study of INP103 (POD L-DOPA) Administered in the Presence of Oral Benserazide And INP107 (PD L-DOPA/DDI Combination Formulation) Administered without Oral Benserazide to L-DOPA Responsive Parkinson's Disease Patients

5.6.3.1. Study Design

A powder formulation of L-DOPA (levodopa) was tested in a randomized, double-blind, placebo controlled, single ascending dose study to demonstrate safety, tolerability and PK/pharmacodynamic of L-DOPA delivered by 1231 Precision Olfactory Delivery ("POD") device to human subjects. The 1231 POD device is a handheld, manually actuated, metered-dose administration device intended to deliver a powder drug formulation to the nasal cavity (i.e. L-DOPA).

L-DOPA responsive Parkinson's disease patients were enrolled in the study. The subjects were males or females between 40 and 80 years of age diagnosed with idiopathic Parkinson's disease and prone to and able to recognize OFF episodes when their usual medication has worn off. They were shown to be responsive to L-DOPA medication, showing more than 30% improvement in MDS-UPDRS Part III Motor Examination score upon administration of L-DOPA.

Subjects were enrolled into one of four dose treatment cohorts with at least 8 subjects per cohort. All subjects in Cohorts 1, 2 and 3 received oral DDI, benserazide hydrochloride, 25 mg at 60±5 minutes before dosing with INP103 or placebo. Subjects in Cohort 4 received the DDI as carbidopa at 1/10$^{th}$ the dose of L-DOPA ("INP107") in the same formulation ("INP107") via the POD device, but no oral DDI treatment. On Day 0 (Visit 3), subjects in each cohort are randomized to receive treatments as follows:

TABLE 21

Study Design (Phase IIa Study)

| Cohort | Number of subjects | Pretreatment (oral administration) | Test Article (intranasal administration) | Dose Regimen |
|---|---|---|---|---|
| 1 | 6 | 25 mg oral Benserazide (at t = −1 h) | 35 mg L-DOPA | one puff to one nostril (at t = 0 h) |
|  | 2 | 25 mg oral Benserazide (at t = −1 h) | Placebo (microcrystalline cellulose) | one puff to one nostril (at t = 0 h) |
| 2 | 6 | 25 mg oral Benserazide (at t = −1 h) | 70 mg L-DOPA | two puffs, one to each nostril (at t = 0 h) |
|  | 2 | 25 mg oral Benserazide (at t = −1 h) | Placebo (microcrystalline cellulose) | two puffs, one to each nostril (at t = 0 h) |
| 3 | 6 | 25 mg oral Benserazide (at t = −1 h) | 140 mg L-DOPA | four puffs, two to each nostril (at t = 0 h) |
|  | 2 | 25 mg oral Benserazide (at t = −1 h) | Placebo (microcrystalline cellulose) | four puffs, two to each nostril (at t = 0 h) |
| 4 | 6 (Max 9) | Vehicle (at t = −1 h) | 70 mg L-DOPA:7.0 mg carbidopa | two puffs, one to each nostril (at t = 0 h) |
|  | 2 (Max3) | Vehicle (at t = −1 h) | Placebo (microcrystalline cellulose) | two puffs, one to each nostril (at t = 0 h) |

In Cohorts 1, 2, and 3, L-DOPA was administered intranasally in single doses of one (35 mg), two (70 mg) or four (140 mg) puffs of INP103, 60 minutes after oral benserazide hydrochloride 25 mg. In Cohort 4, the L-DOPA was intranasally administered in single doses of two puffs of INP107, a formulation that contains carbidopa in a 10:1 L-DOPA:carbidopa ratio (70 mg L-DOPA and 7.0 mg carbidopa (2 capsules)). Dosing took place once an OFF episode was confirmed and did not include pre-dosing with oral benserazide. Placebo was an inert visually similar product without L-DOPA or carbidopa (microcrystalline cellulose).

Subjects were monitored for 7 days after administration of INP103, INP107 or placebo. All subjects were observed as in-patients for at least 240 minutes post-dosing. Follow-up evaluations occurred 7 days after dosing. The Safety Measuring Committee (SMC) had 7-14 days between dosing of Cohorts 1 and 2 and again between 2 and 3 to review safety data compiled by the site and contract research organization (CRO).

Safety and tolerability, pharmacokinetics and pharmacodynamics of intranasally delivered L-DOPA were assessed in the subjects as described below.

Safety and Tolerability Assessments: Specific assessments to evaluate treatment safety included the following: overall dyskinesia assessment, nasal inspection (as part of physical examinations), the frequency and type of adverse events (AEs), concomitant medications (including any short acting anti-OFF medication, permissible only at/after 120 minutes post dosing on dosing days alongside the subject's delayed usual anti-PD morning dose), clinical laboratory testing, 12-lead ECGs and vital signs (to include supine and standing blood pressure, all other vital signs supine only). All treated subjects were observed for 240 minutes post dose and underwent follow-up evaluations (by appropriately trained/qualified staff) at Day 7.

Pharmacokinetic Assessments: In Cohorts 1-3, PK blood samples were collected 15 minutes prior to dosing and at 30, 60, 90, and 120 minutes post dose. In Cohort 4, PK blood samples were collected within 15 minutes prior to dosing and at 4, 9, 14, 29, 44, 59, 89 and 119 minutes after dosing (with INP103 or placebo), typically via indwelling catheter.

Pharmacodynamics Assessments: Measurement of a full MDS-UPDRS score was conducted at the start of all visits. Changes from baseline in MDS-UPDRS Part III scores were estimated using a Mixed Model for Repeated Measures (MMRM) with treatment group (INP103 35 mg L-DOPA, INP103 70 mg L-DOPA, INP103 140 mg L-DOPA, INP107 70 mg/7.0 mg L-DOPA:carbidopa, or placebo), time point (15, 30, 45, 60, 90 or 120 minutes in Cohort 1, Cohort 2, Cohort 3, and at 30, 60, 90, or 120 minutes in Cohort 4) and the interaction between treatment group and time point as fixed factors.

5.6.3.2. Study Formulation

The study drugs were a spray-dried formulation containing L-DOPA:NaCl:HPMC:Maltoside in the ratio 68:2:29:1 (L-DOPA-only formulation; INP103) and a spray-dried formulation containing L-DOPA:NaCl:HPMC:Maltoside in the ratio 63.35:1.86:27.02:0.93 which was blended with a crystalline form of carbidopa at a 10:1 ratio of levodopa: carbidopa (a combination formulation containing both L-DOPA and carbidopa; INP107).

5.6.3.3. Study Results

Dyskinesia assessment, nasal inspection, laboratory evaluations, vital signs assessments (including supine and standing blood pressure, all other vital signs supine only) and ECG parameters showed there was no significant difference between the subjects treated with L-DOPA and placebo. The results demonstrate that L-DOPA delivered by the POD is safe and tolerable.

L-DOPA concentrations in the PK blood samples are summarized in the average plasma concentration-time curves by treatment group and time point in FIGS. 13-14. Both L-DOPA administered by the POD device with oral carbidopa or L-DOPA delivered with carbidopa by the POD device had a trend of dose-dependent pharmacokinetics.

In Cohorts 1-3 (FIG. 13), L-DOPA concentration reached therapeutic blood levels to treat daytime OFF episode at the first blood draw of 30 mins. In many individuals in Cohorts 1-3, peak plasma concentrations were achieved at or before 30 mins. Less than dose proportional PK was observed in Cohorts 1-3, which may be partially due to the total amount of powder delivered to the nasal surface area.

In Cohort 4 (FIG. 14), L-DOPA concentration reached therapeutic blood levels to treat day time OFF episode at 45-90 minutes, and stayed high until 120 mins after administration. This concentration time curve shape of L-DOPA was different from the curve shape of Cohorts 1-3 (FIG. 13), which may be due to local and systemic carbidopa effect. Lower variability of L-DOPA concentrations was observed in Cohort 4, possibly due to the nasal co-administration of carbidopa. $C_{max}$ after intranasal administration of 7 mg carbidopa by the POD was similar to $C_{max}$ measured after oral administration of 50 mg carbidopa, and $T_{max}$ was approximately 4-fold faster than oral administration of carbidopa.

These data from the clinical studies predict that intranasal administration of L-DOPA with oral carbidopa or L-DOPA together with carbidopa by the POD device can be a safe and effective method of treating OFF periods in patients with Parkinson's disease and/or Parkinson syndrome. Additionally, administration of the L-DOPA and carbidopa combination formulation obviated the need for an oral carbidopa to be administered 60 minutes before dosing to attain therapeutic plasma levels of levodopa.

6. INCORPORATION BY REFERENCE

The disclosures of each and every patent, patent application, and publication cited herein are hereby incorporated herein by reference in their entirety.

7. EQUIVALENTS

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a patient with Parkinson's disease (PD) or a Parkinson syndrome, the method comprising the step of:
   delivering an effective amount of a dry pharmaceutical composition directly to the patient's nasal surface area, wherein the dry pharmaceutical composition comprises:
   L-DOPA (levodopa),
   a dopa decarboxylase inhibitor (DDI), and
   at least one excipient.

2. The method of claim 1, wherein the dry pharmaceutical composition is administered by intranasal administration.

3. The method of claim 1, wherein the patient has PD.

4. The method of claim 1, wherein the patient has a Parkinson syndrome selected from post-encephalitic parkinsonism, symptomatic parkinsonism following carbon monoxide intoxication, or symptomatic parkinsonism following manganese intoxication.

5. The method of claim 1, wherein the patient is also being treated with an oral DDI.

6. The method of claim 1, wherein the patient is also being treated with an oral DDI and oral levodopa.

7. The method of claim 1, wherein the patient is not being treated with an oral DDI and oral levodopa.

8. The method of claim 1, wherein the step of delivering is performed when the patient is experiencing an OFF episode.

9. The method of claim 1, wherein the effective amount comprises a dose of levodopa effective to reverse an OFF episode within 60 minutes.

10. The method of claim 1, wherein the effective amount comprises a dose of levodopa sufficient to provide, following administration,
    (a) a mean peak plasma levodopa concentration ($C_{max}$) of at least 400 ng/mL, with
    (b) a mean time to $C_{max}$ ($T_{max}$) of levodopa of less than 60 minutes.

11. The method of claim 1, wherein the effective amount comprises an effective amount of levodopa, where in the effective amount of levodopa is 25-150 mg.

12. The method of claim 11, wherein the effective amount comprises an effective amount of levodopa, wherein the effective amount of levodopa is 35-140 mg.

13. The method of claim 11, wherein the effective amount comprises an effective amount of levodopa, wherein the effective amount of levodopa is 35 mg, 50 mg, 70 mg, 100 mg, or 140 mg.

14. The method of claim 1, wherein the effective amount is administered as a single undivided dose.

15. The method of claim 1, wherein the effective amount is administered as a plurality of equally divided sub-doses.

16. The method of claim 1, wherein the step of delivering is performed using a delivery device, wherein the delivery device is an intranasal administration device.

17. The method of claim 16, wherein the delivery device is a handheld, manually actuated, metered-dose administration device.

18. The method of claim 16, wherein the delivery device is a manually actuated, propellant-driven, metered-dose administration device.

* * * * *